(12) United States Patent
Yoshimura et al.

(10) Patent No.: US 10,689,355 B2
(45) Date of Patent: Jun. 23, 2020

(54) ANTICANCER AGENT

(71) Applicants: Kyoto Pharmaceuticals Industries, Ltd., Kyoto (JP); Sumitomo Dainippon Pharma Co., Ltd., Osaka (JP)

(72) Inventors: Yoshinobu Yoshimura, Kyoto (JP); Masayasu Kasai, Kyoto (JP); Yoshimichi Shoji, Kyoto (JP); Shigemitsu Takeda, Kyoto (JP)

(73) Assignees: Kyoto Pharmaceuticals Industries, Ltd., Kyoto (JP); Sumitomo Dainippon Pharma Co., Ltd., Osaka (JP)

( * ) Notice: Subject to any disclaimer, the term of this patent is extended or adjusted under 35 U.S.C. 154(b) by 0 days.

(21) Appl. No.: 16/455,707

(22) Filed: Jun. 27, 2019

(65) Prior Publication Data
US 2019/0322636 A1     Oct. 24, 2019

Related U.S. Application Data

(63) Continuation of application No. 15/987,525, filed on May 23, 2018, now Pat. No. 10,377,730, which is a continuation of application No. 15/317,471, filed as application No. PCT/JP2015/066625 on Jun. 9, 2015, now Pat. No. 10,005,752.

(30) Foreign Application Priority Data

Jun. 9, 2014  (JP) .................... 2014-119113
Feb. 5, 2015  (JP) .................... 2015-021492

(51) Int. Cl.
| C07D 307/92 | (2006.01) |
| C07H 15/26  | (2006.01) |
| A61P 35/00  | (2006.01) |
| C07D 405/12 | (2006.01) |
| C07D 407/12 | (2006.01) |
| C07F 9/655  | (2006.01) |
| C07H 7/06   | (2006.01) |

(52) U.S. Cl.
CPC ............ *C07D 307/92* (2013.01); *A61P 35/00* (2018.01); *C07D 405/12* (2013.01); *C07D 407/12* (2013.01); *C07F 9/65517* (2013.01); *C07H 7/06* (2013.01); *C07H 15/26* (2013.01)

(58) Field of Classification Search
None
See application file for complete search history.

(56) References Cited

U.S. PATENT DOCUMENTS

| 9,150,530 B2 | 10/2015 | Jiang et al. |
| 2010/0310503 A1 | 12/2010 | Li et al. |
| 2011/0112180 A1 | 5/2011 | Jiang et al. |
| 2012/0065179 A1 | 3/2012 | Andersson |
| 2012/0252763 A1 | 10/2012 | Li et al. |
| 2013/0028944 A1 | 1/2013 | Li et al. |
| 2013/0034591 A1 | 2/2013 | Li et al. |
| 2013/0345176 A1 | 12/2013 | Jiang et al. |
| 2015/0018410 A1 | 1/2015 | Jiang et al. |
| 2015/0164794 A1 | 6/2015 | Jianh et al. |

FOREIGN PATENT DOCUMENTS

| JP | 2010-539095 A | 12/2010 |
| JP | 2010-539097 A | 12/2010 |
| JP | 2010-539098 A | 12/2010 |
| JP | 2013-522325 A | 6/2013 |
| JP | 2013-522326 A | 6/2013 |
| WO | WO 2010/120232 A1 | 10/2010 |
| WO | WO 2012/119265 A1 | 9/2012 |
| WO | WO 2013/120229 A1 | 8/2013 |
| WO | WO 2013/166618 A1 | 11/2013 |

OTHER PUBLICATIONS

Hitron et al., "A phase 1b study of the cancer stem cell inhibitor BBI608 administered with paclitaxel in patients with advanced malignancies," *J. Clin. Oncol.*, 32: 5s (suppl.), 2014 ASCO Annual Meeting, abstract 2530 (May 30, 2014).

Jonker et al., "A phase I extension study of BBI608, a first-in-class cancer stem cell (CSC) inhibitor, in patients with advanced solid tumors," *J. Clin. Oncol.*, 32: 5s (suppl.), 2014 ASCO Annual Meeting, abstract 2546 (Jun. 1, 2014).

Jonker et al., "The NCIC CTG and AGITG CO.23 trial: A phase III randomized study of BBI608 plus best supportive care (BSC) versus placebo (PBO) plus BSC in patients (Pts) with pretreated advanced colorectal carcinoma (CRC)," *J. Clin. Oncol.*, 32: 5s (suppl.), 2014 ASCO Annual Meeting, abstract TPS3660 (May 31, 2014).

Kuckländer, "Mechanism of the Nenitzescu Reaction, V. Synthesis of Naphthofuran Derivatives," *Justus Liebigs Annalen der Chemie*, 1: 140-149 (1978).

(Continued)

*Primary Examiner* — Heidi Reese
(74) *Attorney, Agent, or Firm* — Leydig, Voit & Mayer, Ltd.

(57) ABSTRACT

The problem of the present invention is to provide a useful prodrug compound of a naphthofuran compound. The present invention relates to a compound represented by the formula (IA):

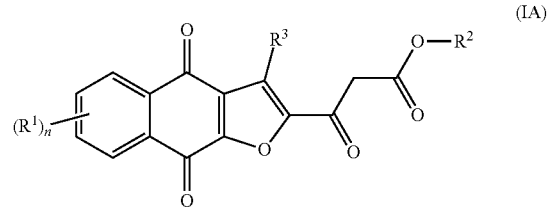

[wherein each symbol is as described in the DESCRIPTION] or a pharmaceutically acceptable salt thereof.

9 Claims, No Drawings

(56) References Cited

OTHER PUBLICATIONS

Li et al., "Suppression of cancer relapse and metastasis by inhibiting cancer stemness," *Proc. Natl. Acad. Sci. USA*, 112(6): 1839-1844 (Feb. 10, 2015).

Reichstein et al., "Synthesis and Structure-Activity Relationships of Lapacho Analogues. 1. Suppression of Human Keratinocyte Hyperproliferation by 2-Substituted Naphtho[2,3-b]furan-4,9-diones, Activation by Enzymatic One- and Two-Electron Reduction, and Intracellular Generation of Superoxide," *Journal of Medicinal Chemistry*, 55(16): 7273-7284 (2012).

Japanese Patent Office, International Search Report in International Patent Application No. PCT/JP2015/066625 (dated Jul. 7, 2015).

ANTICANCER AGENT

CROSS-REFERENCE TO RELATED APPLICATIONS

This patent application is a continuation of co-pending U.S. patent application Ser. No. 15/987,525, filed May 23, 2018, which is a continuation of U.S. patent application Ser. No. 15/317,471, filed Dec. 9, 2016, which issued Jun. 26, 2018 as U.S. Pat. No. 10,005,752, which is the U.S. national phase of International Patent Application PCT/JP2015/066625, filed Jun. 9, 2015, which claims the benefit of Japanese Patent Application 2015-021492, filed Feb. 5, 2015, and Japanese Patent Application 2014-119113, filed Jun. 9, 2014, the disclosures of which are incorporated herein by reference in their entireties for all purposes

TECHNICAL FIELD

The present invention relates to a prodrug of a naphthofuran compound or a pharmaceutically acceptable salt thereof. Also, the present invention relates to a pharmaceutical composition containing the above-mentioned prodrug or a pharmaceutically acceptable salt thereof. Furthermore, the present invention relates to an anticancer agent containing the above-mentioned prodrug or a pharmaceutically acceptable salt thereof, and an agent for the prophylaxis or treatment of cancer metastasis and/or cancer recurrence.

BACKGROUND ART

A prodrug is a compound which scarcely shows expected efficacy by itself but, after administration into the body, is converted to a drug as an active compound by undergoing metabolism by hydrolysis, oxidation, reduction, and the like under physiological conditions to show efficacy. It aims at persistence of pharmacological actions, increase in water-solubility, reduction of side effects and toxicity, improvement of stability in vivo, improvement of taste and odor, and improvement of bioavailability by oral administration (particularly, easy absorption from gastrointestinal tract) and the like, as compared to administration of the drug itself as an active compound.

When a prodrug is designed, consideration is necessary to achieve conversion to an active compound by undergoing metabolism by hydrolysis, oxidation, reduction and the like under physiological conditions. As a typical example thereof, a method including modifying a functional group that the active compound itself has such as amino group, hydroxy group, carboxy group and the like with a particular group is known. For example, it is known that a modifying group is removed by hydrolysis and the like under physiological conditions to restore an amino group, a hydroxy group or a carboxy group in a compound wherein an amino group thereof is eicosanoylated, alanylated, pentylaminocarbonylated, (5-methyl-2-oxo-1,3-dioxolen-4-yl)methoxycarbonylated, tetrahydrofuranylated, pyrrolidylmethylated, pivaloyloxymethylated or tert-butylated when the active compound has an amino group; a compound wherein a hydroxy group thereof is acetylated, palmitoylated, propanoylated, pivaloylated, succinylated, fumarylated, alanylated or dimethylaminomethylcarbonylated when the active compound has a hydroxy group; a compound wherein a carboxy group thereof is ethylesterified, phenylesterified, carboxymethylesterified, dimethylaminomethylesterified, pivaloyloxymethylesterified, 1-ethoxycarbonyloxyethylesterified, phthalidylesterified, (5-methyl-2-oxo-1,3-dioxolen-4-yl)methylesterified or 1-cyclohexyloxycarbonyloxyethylesterified when the active compound has a carboxy group, and the like.

A naphthofuran compound represented by the following formula (A) (hereinafter sometimes to be referred to as compound (A)) has an inhibitory action on Stat3, β-catenin, Nanog pathways and the like, particularly induces apoptosis of cancer stem cells, and is a compound expected to effectively suppress cancer recurrence or metastasis (patent documents 1-5, non-patent documents 1-4).

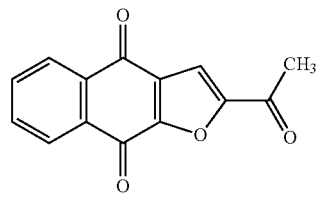

Since compound (A) has low solubility and is unsuitable for injection, it is developed as an oral preparation. However, since it shows low oral absorbability, administration of a high dose is necessary even when pharmaceutical studies of pulverization of bulk powder, use of solubilizing agents and the like are performed, which gives rise to concern about unexpected side effects such as disorder of digestive tract and the like. Therefore, it is desired to achieve improvement of oral absorbability, persistence of pharmacological action, and reduction of side effects and toxicity by converting to a prodrug. Furthermore, since oral administration is often difficult for cancer patients, the development of an injection is also desired. Accordingly, improvement of solubility by converting to a prodrug is desired.

DOCUMENT LIST

Patent Documents

Patent document 1: JP-A-2013-522326
Patent document 2: JP-A-2013-522325
Patent document 3: JP-A-2010-539098
Patent document 4: JP-A-2010-539097
Patent document 5: JP-A-2010-539095

Non-Patent Documents

Non-patent document 1: 2014 ASCO Annual Meeting abstracts, No. 2530
Non-patent document 2: 2014 ASCO Annual Meeting abstracts, No. 2546
Non-patent document 3: 2014 ASCO Annual Meeting abstracts, No. TPS3660
Non-patent document 4: Proc. Natl. Acad. Sci. USA, 2015, 112(6), pages 1839-1844

SUMMARY OF THE INVENTION

Problems to be Solved by the Invention

Since the above-mentioned compound (A) does not have a functional group such as amino group, hydroxy group, carboxy group and the like, a conventional prodrug method by a modifying group cannot be applied. While compound (A) has a structure in which an acetyl group is bonded to aromatic heterocycle, there are only a small number of examples of a prodrug by conversion to an acetyl group and a novel method of converting to a prodrug needs to be developed.

The problem of the present invention is to provide a prodrug compound improved in the solubility, oral absorbability, persistence and side effects such as disorder of gastrointestinal tract and the like of a naphthofuran compound represented by the formula (B) to be mentioned later. Furthermore, it is provision of an anticancer agent superior in solubility, oral absorbability and persistence, and showing less side effects and high safety.

Means of Solving the Problems

The present inventors have conducted intensive studies in an attempt to solve the aforementioned problems and found a novel method for a prodrug, and found that a compound represented by the following formula (IA) or formula (I), or a pharmaceutically acceptable salt thereof, has superior oral absorbability, and further, is easily converted to a naphthofuran compound represented by the formula (B') or formula (B) to be mentioned later, which shows an extremely superior anticancer action as a medicament in the body, and shows superior persistence, which resulted in the completion of the present invention.

The compound and a pharmaceutically acceptable salt thereof of the present invention have high oral absorbability, are converted, after administration, to a compound having a superior anticancer action on cancer cells and capable of inducing apoptosis of cancer stem cells, and show superior persistence. Therefore, they can be a superior anticancer agent particularly capable of preventing or treating cancer metastasis and/or cancer recurrence.

Accordingly, the present invention relates to [1] a compound represented by the formula (IA):

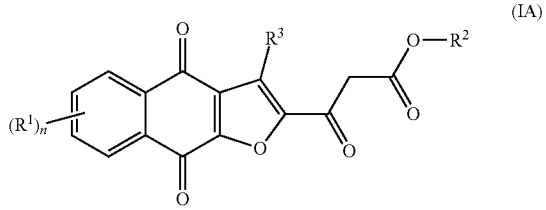

wherein
$R^1$ in the number of n are each independently
a hydrogen atom,
a halogen atom,
hydroxy,
amino,
cyano,
nitro,
$C_{1-12}$ alkyl optionally substituted by substituent(s) selected from substituent group α,
$C_{2-6}$ alkenyl optionally substituted by substituent(s) selected from substituent group α,
$C_{2-6}$ alkynyl optionally substituted by substituent(s) selected from substituent group α,
$C_{3-7}$ cycloalkyl optionally substituted by substituent(s) selected from substituent group α,
$C_{3-7}$ cycloalkenyl optionally substituted by substituent(s) selected from substituent group α,
aryl optionally substituted by substituent(s) selected from substituent group α,
a heterocyclyl group optionally substituted by substituent(s) selected from substituent group α,
$C_{1-6}$ alkoxy optionally substituted by substituent(s) selected from substituent group α,
aryloxy optionally substituted by substituent(s) selected from substituent group α,
$C_{1-6}$ alkylthio optionally substituted by substituent(s) selected from substituent group α, or
arylthio optionally substituted by substituent(s) selected from substituent group α, or
two $R^1$ bonded to the adjacent carbon atoms on a benzene ring are optionally joined to form $C_{1-4}$ alkylenedioxy optionally substituted by substituent(s) selected from substituent group α,
$R^2$ is
$C_{1-12}$ alkyl optionally substituted by substituent(s) selected from substituent group α,
$C_{2-6}$ alkenyl optionally substituted by substituent(s) selected from substituent group α,
$C_{2-6}$ alkynyl optionally substituted by substituent(s) selected from substituent group α,
$C_{3-7}$ cycloalkyl optionally substituted by substituent(s) selected from substituent group α,
aryl optionally substituted by substituent(s) selected from substituent group α,
aryl $C_{1-6}$ alkyl optionally substituted by substituent(s) selected from substituent group α, or
a heterocyclyl group optionally substituted by substituent(s) selected from substituent group α,
$R^3$ is
a hydrogen atom,
a halogen atom,
cyano,
nitro,
$C_{1-12}$ alkyl optionally substituted by substituent(s) selected from substituent group α,
$C_{2-6}$ alkenyl optionally substituted by substituent(s) selected from substituent group α,
$C_{2-6}$ alkynyl optionally substituted by substituent(s) selected from substituent group α,
$C_{3-7}$ cycloalkyl optionally substituted by substituent(s) selected from substituent group α,
$C_{3-7}$ cycloalkenyl optionally substituted by substituent(s) selected from substituent group α,
aryl optionally substituted by substituent(s) selected from substituent group α,
a heterocyclyl group optionally substituted by substituent(s) selected from substituent group α,
$C_{1-6}$ alkoxy optionally substituted by substituent(s) selected from substituent group α,
aryloxy optionally substituted by substituent(s) selected from substituent group α,
$C_{1-6}$ alkylthio optionally substituted by substituent(s) selected from substituent group α, or
arylthio optionally substituted by substituent(s) selected from substituent group α,
n is an integer of 1-4, and
the substituent group α consists of
a halogen atom,
hydroxy,
optionally substituted amino,
carboxy,
$C_{1-6}$ alkoxycarbonyl,
a sulfonic acid group (sulfo group),
a phosphoric acid group, a di $C_{1-6}$ alkyl phosphoric acid group,
cyano,
optionally substituted $C_{1-6}$ alkyl,
$C_{3-7}$ cycloalkyl,
$C_{3-7}$ cycloalkyl $C_{1-6}$ alkyl,
optionally substituted $C_{1-6}$ alkoxy,
$C_{1-6}$ alkylthio,
optionally substituted aryl,
optionally substituted aryloxy,
aryl $C_{1-6}$ alkoxy,
an optionally substituted heterocyclyl group,
optionally substituted $C_{1-6}$ alkylcarbonyl,
heterocyclylcarbonyl,
optionally substituted $C_{1-6}$ alkylcarbonyloxy,
optionally substituted $C_{3-7}$ cycloalkylcarbonyloxy,
arylcarbonyloxy,
heterocyclylcarbonyloxy,
optionally substituted $C_{1-6}$ alkoxycarbonyloxy,
optionally substituted heterocyclyl $C_{1-6}$ alkoxycarbonyloxy,
$C_{3-7}$ cycloalkyloxycarbonyloxy,
heterocyclyloxycarbonyloxy,
optionally substituted heterocyclyloxy,
tri $C_{1-6}$ alkylammonio,
optionally substituted $C_{1-6}$ alkylsulfonyl and $C_{1-6}$ alkylsulfamoylcarbonyl,
or a pharmaceutically acceptable salt thereof;
[2] a compound represented by the formula (I):

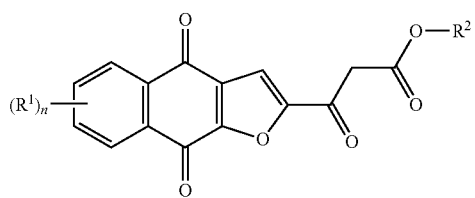

wherein
$R^1$ is
a hydrogen atom or a halogen atom,
$R^2$ is
$C_{1-12}$ alkyl optionally substituted by substituent(s) selected from substituent group α,
$C_{2-6}$ alkenyl optionally substituted by substituent(s) selected from substituent group α,
$C_{2-6}$ alkynyl optionally substituted by substituent(s) selected from substituent group α,
$C_{3-7}$ cycloalkyl optionally substituted by substituent(s) selected from substituent group α,
aryl optionally substituted by substituent(s) selected from substituent group α,
aryl $C_{1-6}$ alkyl optionally substituted by substituent(s) selected from substituent group α, or
a heterocyclyl group optionally substituted by substituent(s) selected from substituent group α,
n is an integer of 1-4, and
the substituent group α consists of
a halogen atom,
hydroxy,
optionally substituted amino,
carboxy,
$C_{1-6}$ alkoxycarbonyl,
a sulfonic acid group (sulfo group),
a phosphoric acid group,
a di $C_{1-6}$ alkyl phosphoric acid group,
cyano,
optionally substituted $C_{1-6}$ alkyl,
$C_{3-7}$ cycloalkyl,
$C_{3-7}$ cycloalkyl $C_{1-6}$ alkyl,
optionally substituted $C_{1-6}$ alkoxy,
$C_{1-6}$ alkylthio,
optionally substituted aryl,
optionally substituted aryloxy,
aryl $C_{1-6}$ alkoxy,
an optionally substituted heterocyclyl group,
optionally substituted $C_{1-6}$ alkylcarbonyl,
heterocyclylcarbonyl,
optionally substituted $C_{1-6}$ alkylcarbonyloxy,
optionally substituted $C_{3-7}$ cycloalkylcarbonyloxy,
arylcarbonyloxy,
heterocyclylcarbonyloxy,
optionally substituted $C_{1-6}$ alkoxycarbonyloxy,
optionally substituted heterocyclyl $C_{1-6}$ alkoxycarbonyloxy,
$C_{3-7}$ cycloalkyloxycarbonyloxy,
heterocyclyloxycarbonyloxy,
optionally substituted heterocyclyloxy,
tri $C_{1-6}$ alkylammonio,
optionally substituted $C_{1-6}$ alkylsulfonyl and
$C_{1-6}$ alkylsulfamoylcarbonyl,
or a pharmaceutically acceptable salt thereof;
[3] the compound of the above-mentioned [1] or [2], wherein
the substituent group α consists of
a halogen atom,
hydroxy,
optionally substituted amino,
carboxy,
$C_{1-6}$ alkoxycarbonyl,
a sulfonic acid group (sulfo group),
a phosphoric acid group,
a di $C_{1-6}$ alkyl phosphoric acid group,
cyano,
$C_{1-6}$ alkyl,
$C_{3-7}$ cycloalkyl,
$C_{1-6}$ alkoxy,
optionally substituted aryl,
optionally substituted aryloxy,
aryl $C_{1-6}$ alkoxy,
an optionally substituted heterocyclyl group,
optionally substituted $C_{1-6}$ alkylcarbonyl,
heterocyclylcarbonyl,
optionally substituted $C_{1-6}$ alkylcarbonyloxy,
optionally substituted $C_{3-7}$ cycloalkylcarbonyloxy,
heterocyclylcarbonyloxy,
optionally substituted $C_{1-6}$ alkoxycarbonyloxy,
optionally substituted heterocyclyl $C_{1-6}$ alkoxycarbonyloxy,
$C_{3-7}$ cycloalkyloxycarbonyloxy,
heterocyclyloxycarbonyloxy,
optionally substituted heterocyclyloxy and
tri $C_{1-6}$ alkylammonio,
or a pharmaceutically acceptable salt thereof;
[4] the compound of the above-mentioned [2], wherein
$R^2$ is $C_{1-6}$ alkyl optionally substituted by substituent(s) selected from substituent group α, $C_{2-6}$ alkenyl optionally substituted by substituent(s) selected from substituent group α, $C_{3-7}$ cycloalkyl optionally substituted by substituent(s) selected from substituent group α, aryl optionally substituted by substituent(s) selected from substituent group α, aryl $C_{1-6}$ alkyl optionally substituted by substituent(s) selected from substituent group α, or a heterocyclyl group optionally substituted by substituent(s) selected from substituent group α, and the substituent group α consists of a halogen atom, hydroxy, optionally substituted amino, carboxy, a sulfonic acid group (sulfo group), a phosphoric acid group, cyano, $C_{1-6}$ alkyl, $C_{3-7}$ cycloalkyl, $C_{1-6}$ alkoxy, aryl and a heterocyclyl group, or a pharmaceutically acceptable salt thereof;

[5] the compound of the above-mentioned [2], wherein $R^2$ is (1) $C_{1-6}$ alkyl optionally substituted by substituent(s) selected from hydroxy, optionally substituted amino, carboxy, a sulfonic acid group (sulfo group), a phosphoric acid group, a di $C_{1-6}$ alkyl phosphoric acid group, a heterocyclyl group, optionally substituted $C_{1-6}$ alkoxy, optionally substituted $C_{1-6}$ alkylcarbonyloxy, heterocyclylcarbonyloxy, $C_{3-7}$ cycloalkyloxycarbonyloxy and heterocyclyloxycarbonyloxy;

(2) $C_{2-6}$ alkynyl optionally substituted by substituent(s) selected from hydroxy, optionally substituted amino, carboxy, a sulfonic acid group (sulfo group), a phosphoric acid group and a heterocyclyl group;

(3) a heterocyclyl group optionally substituted by substituent(s) selected from hydroxy and optionally substituted $C_{1-6}$ alkyl; or (4) aryl $C_{1-6}$ alkyl substituted by substituent(s) selected from hydroxy, optionally substituted amino, carboxy, a sulfonic acid group (sulfo group), a phosphoric acid group and a heterocyclyl group, or a pharmaceutically acceptable salt thereof;

[6] the compound of the above-mentioned [2], wherein $R^2$ is (1) $C_{1-6}$ alkyl optionally substituted by substituent(s) selected from hydroxy, optionally substituted $C_{1-6}$ alkoxy, optionally substituted $C_{1-6}$ alkylcarbonyloxy and heterocyclylcarbonyloxy; or (2) $C_{2-6}$ alkynyl optionally substituted by substituent(s) selected from optionally substituted amino and a heterocyclyl group; or (3) a heterocyclyl group optionally substituted by optionally substituted $C_{1-6}$ alkyl, or a pharmaceutically acceptable salt thereof;

[7] the compound of any of the above-mentioned [1]-[6], wherein $R^1$ in the number of n is a hydrogen atom, or a pharmaceutically acceptable salt thereof;

[8] the compound of the above-mentioned [1], which is any of the compounds of Examples 1-154, or a pharmaceutically acceptable salt thereof;

[9] the compound of the above-mentioned [1], which is

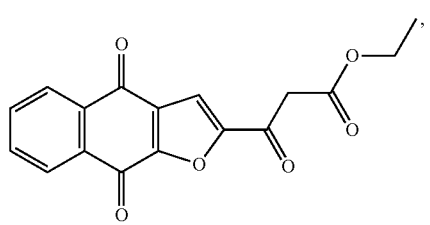

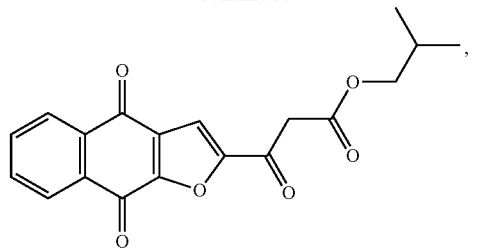

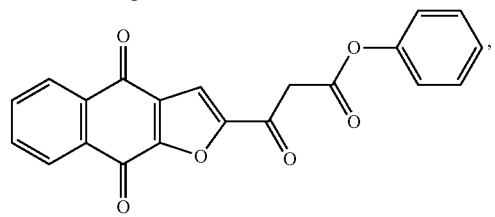

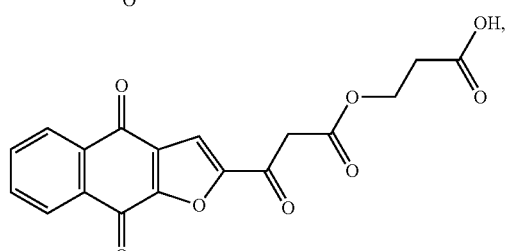

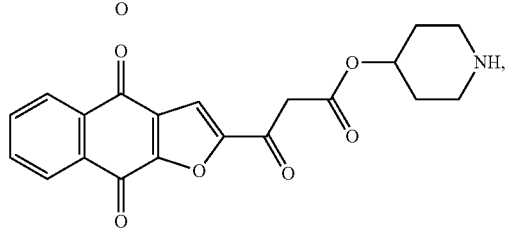

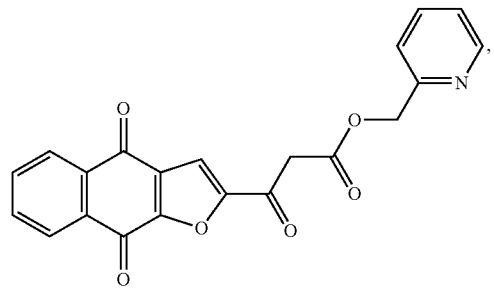

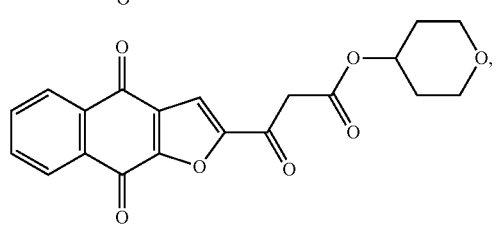

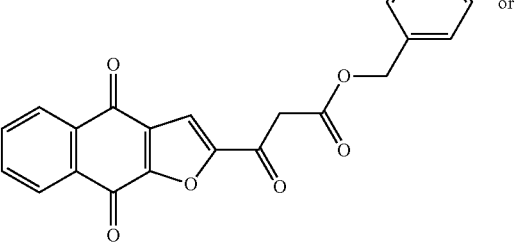

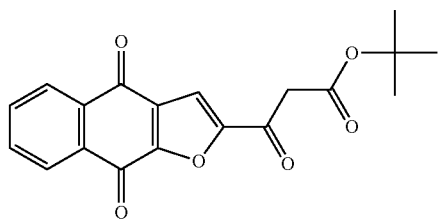
or a pharmaceutically acceptable salt thereof;
[10] the compound of the above-mentioned [1], which is
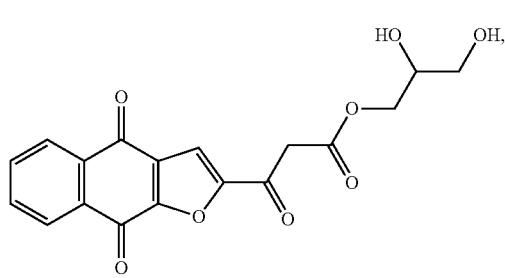
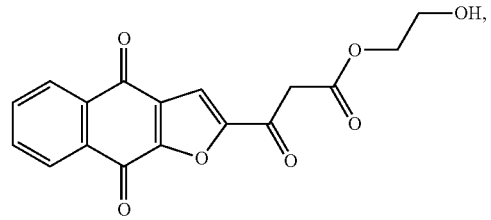
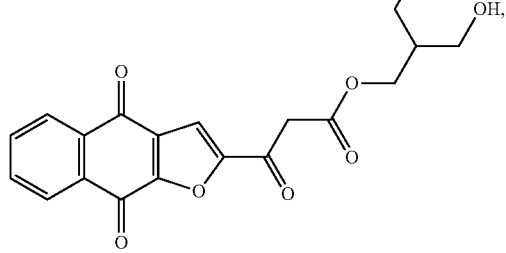
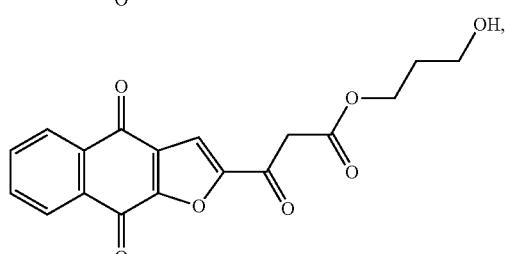
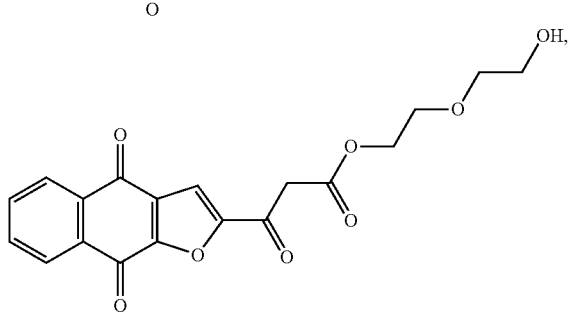
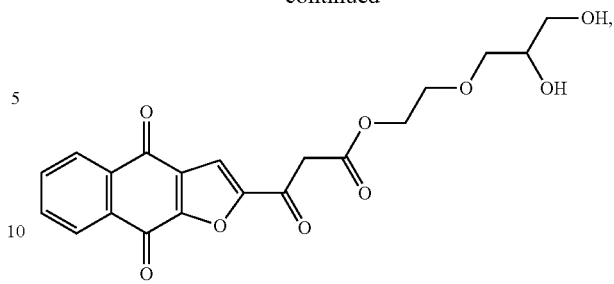
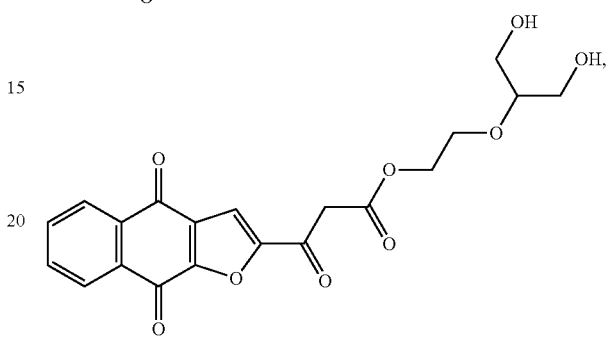
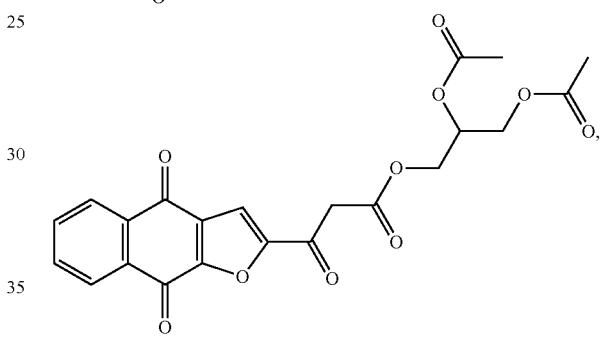
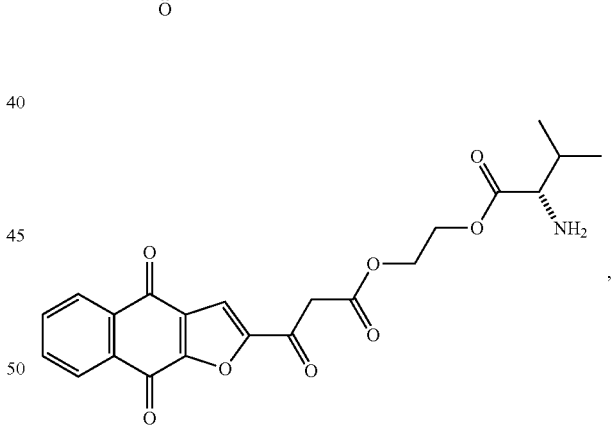
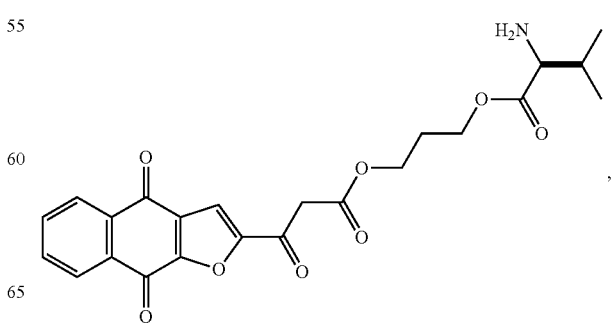

11
-continued
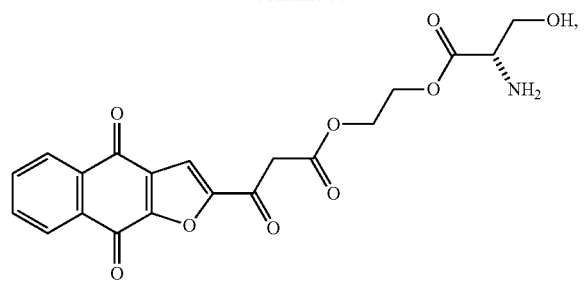
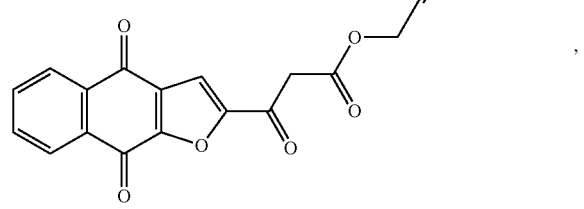
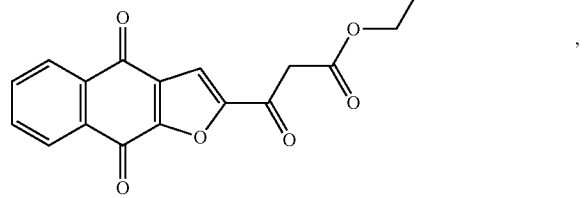
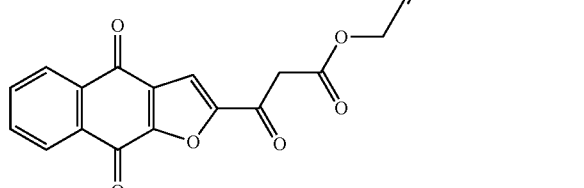
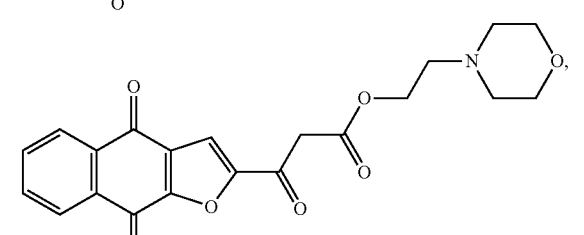
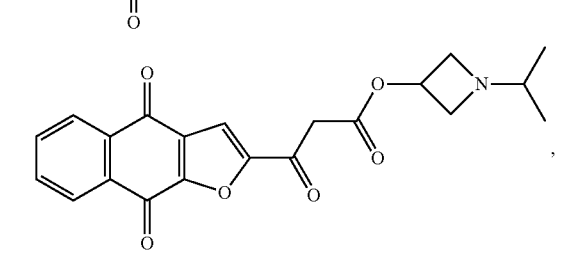
12
-continued
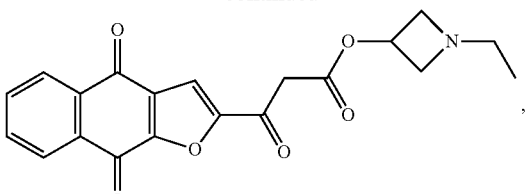
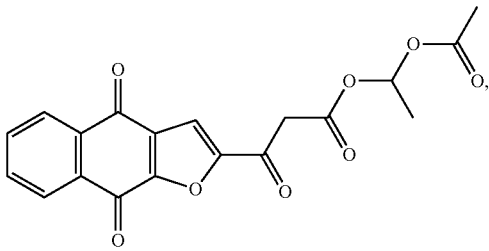
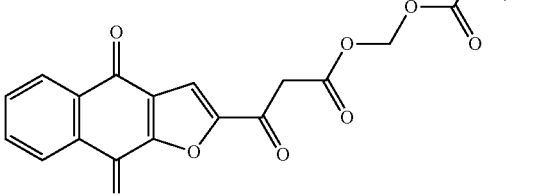
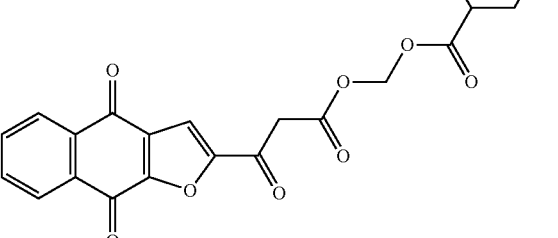
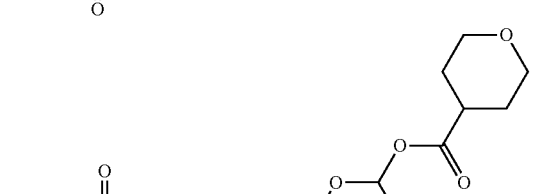
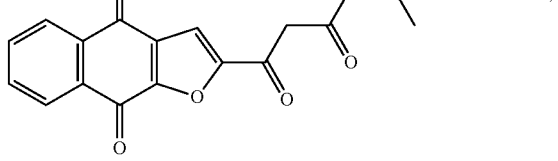
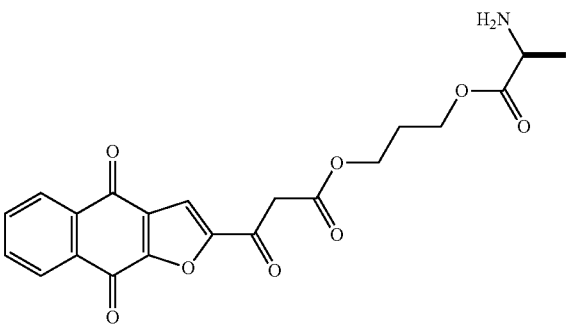

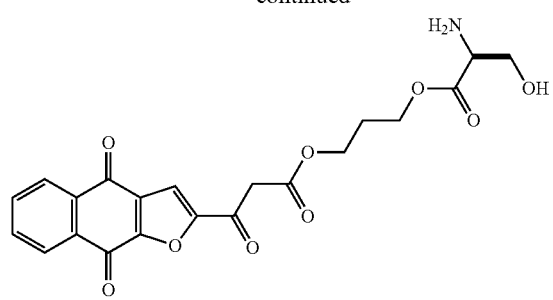
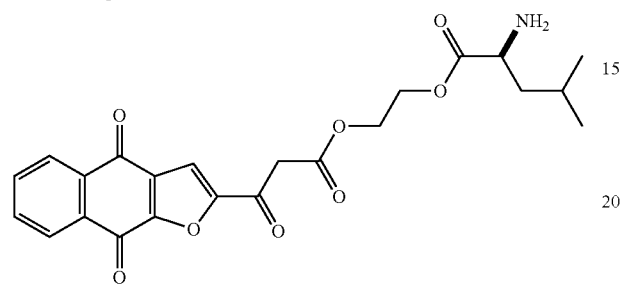
or a pharmaceutically acceptable salt thereof;
[11] the compound of the above-mentioned [1], which is
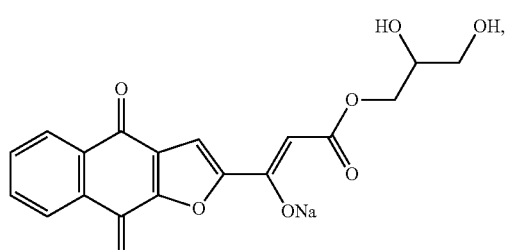
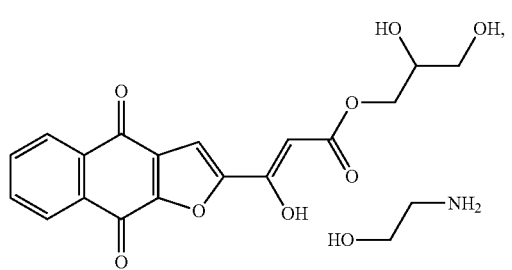
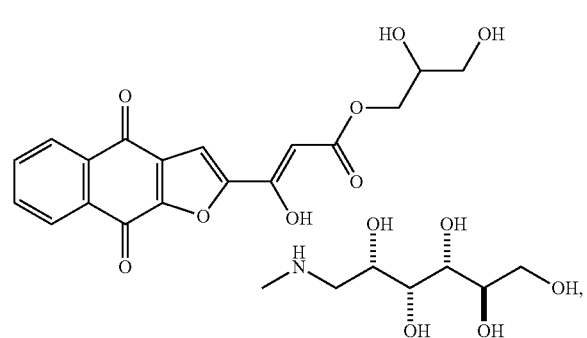
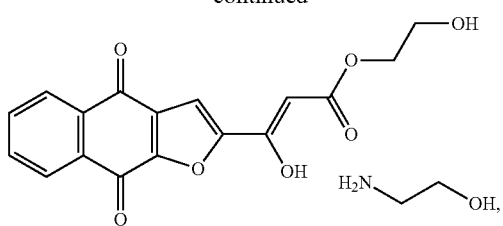
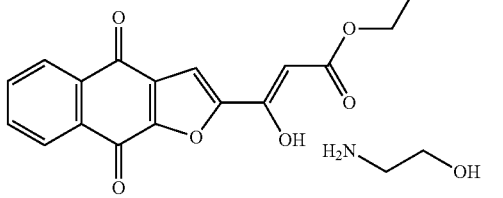
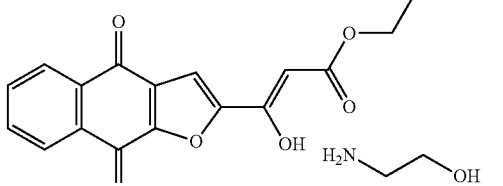
or

[12] a pharmaceutical composition comprising a compound of any of the above-mentioned [1]-[11] or a pharmaceutically acceptable salt thereof as an active ingredient;
[13] an anticancer agent comprising a compound of any of the above-mentioned [1]-[11] or a pharmaceutically acceptable salt thereof as an active ingredient;
[14] a prophylactic or therapeutic agent for cancer, cancer metastasis and/or cancer recurrence, comprising a compound of any of the above-mentioned [1]-[11] or a pharmaceutically acceptable salt thereof as an active ingredient;
[15] the agent of the above-mentioned [13] or [14], targeting a cancer stem cell;
and the like.

Effect of the Invention

A compound represented by the above-mentioned formula (IA) (hereinafter sometimes to be referred to as compound (IA)) and a pharmaceutically acceptable salt thereof of the present invention are prodrugs which undergo, after administration to the body, metabolism such as hydrolysis and the like under physiological conditions and are converted to a compound represented by the following formula (B') (hereinafter sometimes to be referred to as compound (B')), and a compound represented by the formula (I) (hereinafter sometimes to be referred to as compound (I)) and a pharmaceutically acceptable salt thereof, which are encompassed in compound (IA), are prodrugs which undergo, after administration to the body, metabolism such as hydrolysis and the like under physiological conditions and are converted to a compound represented by the following formula (B) (hereinafter sometimes to be referred to as compound (B)). They have high oral absorbability and superior persistence, and are useful as anticancer agents, or agents for the prophylaxis or treatment of cancer metastasis and/or cancer recurrence.

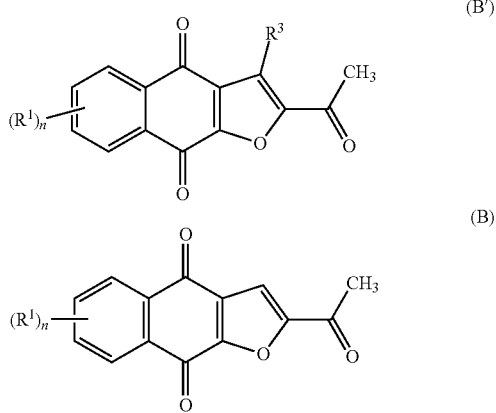

In addition, a medicament containing compound (IA) or compound (I) of the present invention as an active ingredient shows high oral absorbability and less side effects, and therefore, it can be a highly safe therapeutic agent for cancer or an agent for the prophylaxis or treatment of cancer metastasis and/or cancer recurrence. Moreover, since compound (IA) or compound (I) of the present invention show improved water-solubility, compound (IA) or compound (I) can be each prepared as an injection, which is heretofore difficult to prepare from compound (B') and compound (B).

Compound (IA) or compound (I) of the present invention, or a pharmaceutically acceptable salt thereof are useful as agents for the prophylaxis or treatment of, but are not limited to, breast cancer, head and neck cancer, lung cancer, ovarian cancer, pancreatic cancer, colonrectal cancer, prostate cancer, esophageal cancer, nasopharyngeal cancer, pituitary cancer, gallbladder cancer, thyroid cancer, salivary gland cancer, urinary bladder cancer, renal cell carcinoma, melanoma, hepatoma, cervical cancer, endometrial carcinoma, Kaposi's sarcoma, Ewing's sarcoma, medulloblastoma, sarcoma, brain tumor, gastric cancer, multiple myeloma, leukemia or lymphoma.

DESCRIPTION OF EMBODIMENTS

The present invention is explained in detail in the following.

The definition of the term and each symbol used in the present specification is explained in the following.

In the present specification, the "halogen atom" refers to a fluorine atom, a chlorine atom, a bromine atom or an iodine atom.

In the present specification, the "$C_{1-6}$ alkyl" means a linear or branched chain monovalent saturated hydrocarbon group having 1-6 carbon atoms. Examples of the "$C_{1-6}$ alkyl" include methyl, ethyl, propyl, isopropyl, butyl, isobutyl, sec-butyl, tert-butyl, pentyl, isopentyl, neopentyl, 1-ethylpropyl, 4-methylpentyl, hexyl and the like.

In the present specification, the "$C_{1-12}$ alkyl" means a linear or branched chain monovalent saturated hydrocarbon group having 1-12 carbon atoms. Examples of the "$C_{1-12}$ alkyl" include methyl, ethyl, propyl, isopropyl, butyl, isobutyl, sec-butyl, tert-butyl, pentyl, isopentyl, neopentyl, 1-ethylpropyl, 4-methylpentyl, hexyl, heptyl, octyl, nonyl, decyl, undecyl, dodecyl and the like.

In the present specification, the "$C_{3-7}$ cycloalkyl" means a monovalent group induced from a saturated hydrocarbon ring having 3-7 carbon atoms. The "cycloalkyl" may be crosslinked. Examples of the "$C_{3-7}$ cycloalkyl" include cyclopropyl, cyclobutyl, cyclopentyl, cyclohexyl, cycloheptyl and the like.

In the present specification, the "$C_{3-7}$ cycloalkyl $C_{1-6}$ alkyl" means a monovalent group wherein the aforementioned "$C_{3-7}$ cycloalkyl" is bonded to the aforementioned "$C_{1-6}$ alkyl". Examples of the "$C_{3-7}$ cycloalkyl $C_{1-6}$ alkyl" include cyclopropylmethyl, cyclobutylmethyl, cyclopentylmethyl, cyclohexylmethyl, cycloheptylmethyl and the like.

In the present specification, the "$C_{1-4}$ alkylene" means a linear or branched chain divalent saturated hydrocarbon group having 1-4 carbon atoms. Examples of the "$C_{1-4}$ alkylene" include methylene, ethylene, propane-1,3-diyl, butane-1,4-diyl and the like.

In the present specification, the "$C_{3-7}$ cycloalkenyl" means a monovalent group induced from an unsaturated hydrocarbon ring having 3-7 carbon atoms. The "cycloalkenyl" may be crosslinked. Examples of the "$C_{3-7}$ cycloalkenyl" include cyclopropenyl, cyclobutenyl, cyclopentenyl, cyclohexenyl, cycloheptenyl and the like.

In the present specification, the "$C_{2-6}$ alkenyl" means a linear or branched chain monovalent hydrocarbon group having one or more carbon-carbon double bond and 2-6 carbon atoms. Examples of the "$C_{2-6}$ alkenyl" include vinyl, 1-propenyl (allyl), 2-propenyl, isopropenyl, 2-methyl-1-propenyl, 1-butenyl, 2-butenyl, 3-butenyl, 2-buten-2-yl, 3-methyl-2-butenyl, 3-methyl-2-buten-2-yl, 1-pentenyl, 2-pentenyl, 3-pentenyl, 4-pentenyl, 2-penten-2-yl, 2-penten- 3-yl, 4-methyl-1-pentenyl, 1-hexenyl, 2-hexenyl, 3-hexenyl, butadienyl (e.g., but-1,3-dien-1-yl), pentadienyl (e.g., penta-1,3-dien-1-yl) and the like.

In the present specification, the "$C_{2-6}$ alkynyl" means a linear or branched chain monovalent hydrocarbon group having one or more carbon-carbon triple bonds and 2-6 carbon atoms. Examples of the "$C_{2-6}$ alkynyl" include ethenyl, 1-propynyl, 2-propynyl, 1-butynyl, 2-butynyl, 3-butynyl, 3-methyl-2-butynyl, 1-pentynyl, 2-pentynyl, 3-pentynyl, 4-pentynyl, 4-methyl-1-pentynyl and the like.

In the present specification, the "$C_{1-6}$ alkoxy" means a group wherein the aforementioned "$C_{1-6}$ alkyl" group is bonded to an oxygen atom, i.e., a straight chain or branched chain alkoxy group having 1-6 carbon atoms. Examples of the "$C_{1-6}$ alkoxy" include methoxy, ethoxy, propoxy, isopropoxy, butoxy, isobutoxy, sec-butoxy, tert-butoxy, pentyloxy, isopentyloxy, neopentyloxy, 1-ethylpropyloxy, hexyloxy and the like.

In the present specification, the "$C_{1-4}$ alkylenedioxy" means a divalent group wherein an oxygen atom is bonded to each of the two binding sites of the aforementioned "$C_{1-4}$ alkylene" group. Examples of the "$C_{1-4}$ alkylenedioxy" include methylenedioxy, ethylenedioxy, propane-1,3-dioxy, butane-1,4-dioxy and the like.

In the present specification, the "$C_{1-6}$ alkylthio" means a group wherein the aforementioned "$C_{1-6}$ alkyl" group is bonded to a sulfur atom, i.e., a straight chain or branched chain alkylthio group having 1-6 carbon atoms. Examples of the "$C_{1-6}$ alkylthio" include methylthio, ethylthio, propylthio, isopropylthio, butylthio, isobutylthio, sec-butylthio, tert-butylthio, pentylthio, isopentylthio, neopentylthio, 1-ethylpropylthio, hexylthio and the like.

In the present specification, the "$C_{1-6}$ alkoxycarbonyl" means a group wherein the aforementioned "$C_{1-6}$ alkoxy" group is bonded to carbonyl, i.e., a straight chain or branched chain alkoxy-carbonyl group having 1-6 carbon atoms. Examples of the "$C_{1-6}$ alkoxycarbonyl" include methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl, pentyloxycarbonyl, isopentyloxycarbonyl, neopentyloxycarbonyl, 1-ethylpropyloxycarbonyl, hexyloxycarbonyl and the like.

In the present specification, the "$C_{1-6}$ alkylsulfamoylcarbonyl" means a group wherein the nitrogen atom of a "$C_{1-6}$ alkylsulfamoyl ($C_{1-6}$ alkyl-$S(O)_2NH_2$)" group is bonded to carbonyl, i.e., a straight chain or branched chain alkylsulfamoyl-carbonyl group having 1-6 carbon atoms. Examples of the "$C_{1-6}$ alkylsulfamoylcarbonyl" include methanesulfamoylcarbonyl and the like.

In the present specification, the "di $C_{1-6}$ alkyl phosphoric acid group" means a monovalent group wherein the same or different the aforementioned two "$C_{1-6}$ alkyl" groups are esterified to a phosphoric acid group. Examples of the "di $C_{1-6}$ alkyl phosphoric acid group" include dimethylphosphoric acid group, diethylphosphoric acid group, dipropylphosphoric acid group, diisopropylphosphoric acid group, dibutylphosphoric acid group, diisobutylphosphoric acid group, di sec-butylphosphoric acid group, di-tert-butylphosphoric acid group and the like.

In the present specification, the "aryl" means a monovalent aromatic hydrocarbon group having 6-14 carbon atoms. Examples of the "aryl" include phenyl, naphthyl (e.g., 1-naphthyl, 2-naphthyl), acenaphthylenyl, azulenyl, anthryl, phenanthryl and the like.

In the present specification, the "aryloxy" means a monovalent group wherein the aforementioned "aryl" group is bonded to an oxygen atom. Examples of the "aryloxy" include phenoxy, naphthyloxy (e.g., 1-naphthyloxy, 2-naphthyloxy), acenaphthylenyloxy, azulenyloxy, anthryloxy, phenanthryloxy and the like.

In the present specification, the "arylthio" means a monovalent group wherein the aforementioned "aryl" group is bonded to a sulfur atom. Examples of the "arylthio" include phenylthio, naphthylthio (e.g., 1-naphthylthio, 2-naphthylthio), acenaphthylenylthio, azulenylthio, anthrylthio, phenanthrylthio and the like.

In the present specification, the "aryl $C_{1-6}$ alkyl" means a monovalent group wherein the aforementioned "aryl" group is bonded to the aforementioned "$C_{1-6}$ alkyl". Examples of the "aryl $C_{1-6}$ alkyl" include benzyl, naphthylmethyl, 2-phenylethyl, 1-phenylethyl, 1-phenylpropyl and the like.

In the present specification, the "aryl $C_{1-6}$ alkoxy" means a monovalent group wherein the aforementioned "aryl $C_{1-6}$ alkyl" group is bonded to an oxygen atom. Examples of the "aryl $C_{1-6}$ alkoxy" include benzyloxy, naphthylmethyloxy, 2-phenylethyloxy, 1-phenylethyloxy, 1-phenylpropyloxy and the like.

In the present specification, the "heterocyclyl group" means a 3- to 14-membered (monocyclic, bicyclic or tricyclic) heterocyclyl group containing at least one hetero atom selected from the group consisting of oxygen atom, nitrogen atom and sulfur atom, and aromatic heterocycle and nonaromatic heterocycle can be mentioned.

In the present specification, the "aromatic heterocyclyl group" means a monovalent 5- to 14-membered monocyclic aromatic heterocyclyl group and a fused aromatic heterocyclyl group, each containing at least one hetero atom selected from the group consisting of oxygen atom, nitrogen atom and sulfur atom. The fused aromatic heterocyclyl group in the present invention is bi or tricyclic, and optionally has a hetero atom on plural rings. As the monocyclic aromatic heterocyclyl group, a 5- or 6-membered ring group can be mentioned; and as a fused aromatic heterocyclyl group, a group wherein each ring constituting the group is a 5- or 6-membered ring can be mentioned. Examples of the "aromatic heterocyclyl group" include monocyclic aromatic heterocyclyl groups such as furyl, thienyl, pyrrolyl, imidazolyl, pyrazolyl, oxazolyl, isoxazolyl, thiazolyl, triazolyl, tetrazolyl, thiadiazolyl, oxadiazolyl, pyridyl, pyridazinyl, pyrimidinyl and the like, fused aromatic heterocyclyl groups such as indolyl, isoindolyl, indazolyl, benzofuranyl, benzothiophenyl, benzimidazolyl (e.g., 5-benzimidazolyl), benzoxazolyl, benzothiazolyl, quinolyl, isoquinolyl, benzoxazinyl, benzothiazinyl, furo[2,3-b]pyridyl, thieno[2,3-b]pyridyl, naphthyridinyl, imidazopyridyl, oxazolopyridyl, thiazolopyridyl, quinolyl, carbazolyl, dibenzothiophenyl and the like.

In the present specification, the "nonaromatic heterocyclyl group" means a monovalent 3- to 14-membered monocyclic nonaromatic heterocyclyl group or a fused nonaromatic heterocyclyl group, each containing at least one hetero atom selected from the group consisting of oxygen atom, nitrogen atom and sulfur atom. The fused nonaromatic heterocyclyl group in the present invention is bi or tricyclic and optionally has a hetero atom on both rings. As the monocyclic nonaromatic heterocyclyl group, a 3- to 9-membered ring group can be mentioned; and as a fused nonaromatic heterocyclyl group, a group wherein each ring constituting the group is a 5- or 6-membered ring can be mentioned. Examples of the "nonaromatic heterocyclyl group" include monocyclic nonaromatic heterocyclyl groups such as oxetanyl (e.g., 3-oxetanyl), tetrahydrofuryl (e.g., tetrahydrofuran-3-yl), dioxolyl (e.g., 1,3-dioxol-4-yl), dioxolanyl (e.g., 1,3-dioxolan-4-yl), oxazolidinyl, imidazolinyl (e.g., 1-imidazolinyl, 2-imidazolinyl, 4-imidazolinyl), aziridinyl (e.g., 1-aziridinyl, 2-aziridinyl), azetidinyl (e.g., 1-azetidinyl, 2-azetidinyl, 3-azetidinyl), pyrrolidinyl (e.g., 1-pyrrolidinyl, 2-pyrrolidinyl, 3-pyrrolidinyl), piperidyl (e.g., 1-piperidyl, 2-piperidyl, 3-piperidyl, 4-piperidyl), dioxanyl (e.g., 1,4-dioxan-2-yl), azepanyl (e.g., 1-azepanyl, 2-azepanyl, 3-azepanyl, 4-azepanyl), azocanyl (e.g., 1-azocanyl, 2-azocanyl, 3-azocanyl, 4-azocanyl), azonanyl (e.g., 1-azonanyl, 2-azonanyl, 3-azonanyl, 4-azonanyl, 5-azonanyl), piperazinyl (e.g., 1,4-piperazin-1-yl, 1,4-piperazin-2-yl), diazepinyl (e.g., 1,4-diazepin-1-yl, 1,4-diazepin-2-yl, 1,4-diazepin-5-yl, 1,4-diazepin-6-yl), diazocanyl (e.g., 1,4-diazocan-1-yl, 1,4-diazocane-2-yl, 1,4-diazocane-5-yl, 1,4-diazocane-6-yl, 1,5-diazocan-1-yl, 1,5-diazocane-2-yl, 1,5-diazocane-3-yl), tetrahydropyranyl (e.g., tetrahydropyran-4-yl, tetrahydropyran-2-yl), morpholinyl (e.g., 4-morpholinyl), thiomorpholinyl (e.g., 4-thiomorpholinyl), 2-oxazolidinyl, dihydrofuryl, dihydropyranyl and the like, a fused nonaromatic heterocyclyl groups such as dihydroquinolyl, dihydroisoquinolyl (e.g., 3,4-dihydroisoquinolin-2-yl), dihydroindole (e.g., 2,3-dihydroindol-5-yl, 2,3-dihydroindol-1-yl), dihydroisoindole (e.g., 2,3-dihydroisoindol-2-yl) and the like, and the like.

In the present specification, the "heterocyclylcarbonyl" means a monovalent group wherein the aforementioned "heterocyclyl" group is bonded to a carbonyl. Preferable examples of the "heterocyclylcarbonyl" include morpholinocarbonyl, piperidinocarbonyl and the like.

In the present specification, the "heterocyclylcarbonyloxy" means a monovalent group wherein the aforementioned "heterocyclylcarbonyl" group is bonded to an oxygen atom. Preferable examples of the "heterocyclylcarbonyloxy" include tetrahydropyran-4-ylcarbonyloxy, piperidin-4-ylcarbonyloxy, pyrrolidin-2-ylcarbonyloxy, azetidin-3-ylcarbonyloxy and the like.

In the present specification, the "$C_{1-6}$ alkylcarbonyloxy" means a monovalent group wherein the aforementioned "$C_{1-6}$ alkyl" group is bonded to carbonyloxy. Examples of the "$C_{1-6}$ alkylcarbonyloxy" include acetyloxy, propionyloxy, butyryloxy, isobutyryloxy, pentanoyloxy, isopentanoyloxy, 1-methylbutyryloxy, pivaloyloxy, hexanoyloxy, isohexanoyloxy, 3,3-dimethylbutyryloxy, 1-ethylbutyryloxy, 4-methylhexanoyloxy, heptanoyloxy and the like.

In the present specification, the "arylcarbonyloxy" means a monovalent group wherein the aforementioned "aryl" group is bonded to carbonyloxy. Preferable examples of the "arylcarbonyloxy" include benzoyloxy and the like.

In the present specification, the "$C_{3-7}$ cycloalkylcarbonyloxy" means a monovalent group wherein the aforementioned "$C_{3-7}$ cycloalkyl" group is bonded to carbonyloxy. Examples of the "$C_{3-7}$ cycloalkylcarbonyloxy" include cyclopropylcarbonyloxy, cyclobutylcarbonyloxy, cyclopentylcarbonyloxy, cyclohexylcarbonyloxy, cycloheptylcarbonyloxy and the like.

In the present specification, the "$C_{1-6}$ alkoxycarbonyloxy" means a monovalent group wherein the aforementioned "$C_{1-6}$ alkoxycarbonyl" group is bonded to an oxygen atom. Examples of the "$C_{1-6}$ alkoxycarbonyloxy" include methoxycarbonyloxy, ethoxycarbonyloxy, propoxycarbonyloxy, isopropoxycarbonyloxy, butoxycarbonyloxy, isobutoxycarbonyloxy, sec-butoxycarbonyloxy, tert-butoxycarbonyloxy, pentyloxycarbonyloxy, isopentyloxycarbonyloxy, neopentyloxycarbonyloxy, 1-ethylpropyloxycarbonyloxy, hexyloxycarbonyloxy and the like.

In the present specification, the "heterocyclyl $C_{1-6}$ alkoxycarbonyloxy" means a monovalent group wherein the aforementioned "heterocyclyl" group is bonded to the aforementioned "$C_{1-6}$ alkoxycarbonyloxy". Preferable examples of the "heterocyclyl $C_{1-6}$ alkoxycarbonyloxy" include dioxolan-4-ylmethoxycarbonyloxy and the like.

In the present specification, the "$C_{3-7}$ cycloalkyloxycarbonyloxy" means a "$C_{3-7}$ cycloalkyloxycarbonyloxy" wherein the $C_{3-7}$ cycloalkyl moiety is the aforementioned "$C_{3-7}$ cycloalkyl" group. Examples of the "$C_{3-7}$ cycloalkyloxycarbonyloxy" include cyclopropyloxycarbonyloxy, cyclobutyloxycarbonyloxy, cyclopentyloxycarbonyloxy, cyclohexyloxycarbonyloxy, cycloheptyloxycarbonyloxy and the like.

In the present specification, the "heterocyclyloxycarbonyloxy" means a "heterocyclyloxycarbonyloxy" wherein the heterocyclyl moiety is the aforementioned "heterocyclyl" group. Preferable examples of the "heterocyclyloxycarbonyloxy" include tetrahydropyran-4-yloxycarbonyloxy and the like.

In the present specification, the "heterocyclyloxy" means a monovalent group wherein the aforementioned "heterocyclyl" group is bonded to an oxygen atom. Preferable examples of the "heterocyclyloxy" include tetrahydropyran-2-yloxy and the like.

In the present specification, the "tri $C_{1-6}$ alkylammonio" means a "tri $C_{1-6}$ alkylammonio" wherein the $C_{1-6}$ alkyl moiety is the aforementioned "$C_{1-6}$ alkyl" group. Preferable examples of the "tri $C_{1-6}$ alkylammonio" include trimethylammonio, triethylammonio and the like.

Being "optionally substituted" means an embodiment of being unsubstituted or substituted by 1-4 substituents. When di- to tetra-substituted, the respective substituents may be the same or different.

Being "substituted" means an embodiment of being substituted by 1-4 substituents. When di- to tetra-substituted, the respective substituents may be the same or different.

In the present specification, the "optionally substituted $C_{1-6}$ alkyl" means $C_{1-6}$ alkyl optionally substituted by 1-4 substituents selected from a halogen atom, hydroxy, carboxy, cyano, nitro, optionally substituted amino, a sulfonic acid group (sulfo group), a phosphoric acid group, a di $C_{1-6}$ alkyl phosphoric acid group, optionally substituted $C_{1-6}$ alkoxy, $C_{3-7}$ cycloalkyl, a heterocyclyl group, optionally substituted $C_{1-6}$ alkylcarbonyloxy, heterocyclylcarbonyloxy, $C_{3-7}$ cycloalkyloxycarbonyloxy, and heterocyclyloxycarbonyloxy. Preferable examples of the "optionally substituted $C_{1-6}$ alkyl" include 2-aminoethyl, 2-hydroxyethyl, 2-carboxyethyl and the like.

In the present specification, the "optionally substituted $C_{1-6}$ alkoxy" means $C_{1-6}$ alkoxy optionally substituted by 1-4 substituents selected from a halogen atom, hydroxy, carboxy, cyano, nitro, optionally substituted amino, $C_{1-6}$ alkoxy, $C_{3-7}$ cycloalkyl, $C_{2-6}$ alkenyl, $C_{2-6}$ alkynyl, aryl, $C_{1-6}$ alkylsulfamoylcarbonyl, and a heterocyclyl group. Preferable examples of the "optionally substituted $C_{1-6}$ alkoxy" include 2-diethylaminoethoxy, 2-carboxyethoxy, 2-methanesulfamoylcarbonylethoxy, 2-hydroxyethoxy, 2,3-dihydroxypropoxy, 1,3-dihydroxy-2-propoxy, 2-[2-(2-hydroxyethoxy)ethoxy]ethoxy and the like.

In the present specification, the "optionally substituted amino" means an amino optionally substituted by 1 or 2 substituents selected from $C_{1-6}$ alkyl, $C_{3-7}$ cycloalkyl, $C_{2-6}$ alkenyl, $C_{2-6}$ alkynyl, aryl, aryl $C_{1-6}$ alkyl, optionally substituted $C_{1-6}$ alkylcarbonyl, and a heterocyclyl group. Examples of the "optionally substituted amino" include amino, methylamino, ethylamino, propylamino, isopropylamino, butylamino, isobutylamino, sec-butylamino, tert-butylamino, cyclopropylamino, cyclobutylamino, 1-propenylamino (allylamino), phenylamino, naphthylamino (e.g., 1-naphthylamino, 2-naphthylamino), benzylamino, naphthylmethylamino, 2-phenylethylamino, pyridylamino, dimethylamino, diethylamino, N-methyl-N-ethylamino, N-methyl-N-(2-amino-3-methylbutyryl)amino and the like.

In the present specification, the "optionally substituted aryl" means an aryl optionally substituted by 1-4 substituents selected from $C_{1-6}$ alkyl, $C_{1-6}$ alkoxy, $C_{3-7}$ cycloalkyl, $C_{2-6}$ alkenyl, $C_{2-6}$ alkynyl, aryl, aryl $C_{1-6}$ alkyl, a heterocyclyl group, a halogen atom, hydroxy, amino, carboxy, cyano, and nitro. Preferable examples of the "optionally substituted aryl" include 4-carboxyphenyl and the like.

In the present specification, the "optionally substituted aryloxy" means aryloxy optionally substituted by 1-4 substituents selected from $C_{1-6}$ alkyl optionally substituted by substituent(s) selected from amino and carboxy, $C_{1-6}$ alkoxy, $C_{3-7}$ cycloalkyl, $C_{2-6}$ alkenyl, $C_{2-6}$ alkynyl, aryl, aryl $C_{1-6}$ alkyl, a heterocyclyl group, a halogen atom, hydroxy, amino, carboxy, cyano, and nitro. Preferable examples of the "optionally substituted aryloxy" include 4-(2-amino-2-carboxyethyl)phenoxy and the like.

In the present specification, the "optionally substituted heterocyclyl group" means a heterocyclyl group optionally substituted by 1-4 substituents selected from $C_{1-6}$ alkyl, $C_{1-6}$ alkoxy, $C_{3-7}$ cycloalkyl, $C_{2-6}$ alkenyl, $C_{2-6}$ alkynyl, aryl, aryl $C_{1-6}$ alkyl, a heterocyclyl group, a halogen atom, hydroxy, amino, carboxy, cyano, nitro and oxo. Preferable examples of the "optionally substituted heterocyclyl group" include 5-methyl-2-oxo-1,3-dioxol-4-yl, 3,4,5,6-tetrahydroxytetrahydropyran-2-yl, 1,4-dioxan-2-yl, 2,2-dimethyl-1,3-dioxolan-4-yl, 2-oxo-1,3-dioxolan-4-yl, piperazin-1-yl, 4-(2-propenyl)piperazin-1-yl, morpholin-4-yl, 3-pyridyl and the like.

In the present specification, the "optionally substituted $C_{1-6}$ alkylcarbonyl" means a $C_{1-6}$ alkylcarbonyl optionally substituted by 1-4 substituents selected from $C_{1-6}$ alkyl, $C_{1-6}$ alkylcarbonyloxy, $C_{1-6}$ alkoxy, $C_{3-7}$ cycloalkyl, $C_{2-6}$ alkenyl, $C_{2-6}$ alkynyl, aryl, aryl $C_{1-6}$ alkyl, a heterocyclyl group, a halogen atom, hydroxy, amino, carboxy, cyano and nitro. Preferable examples of the "optionally substituted $C_{1-6}$ alkylcarbonyl" include carboxyacetyl and the like.

In the present specification, the "optionally substituted $C_{1-6}$ alkylcarbonyloxy" means $C_{1-6}$ alkylcarbonyloxy optionally substituted by 1-4 substituents selected from $C_{1-6}$ alkyl, $C_{1-6}$ alkylcarbonyloxy, $C_{1-6}$ alkoxy, $C_{3-7}$ cycloalkyl, $C_{2-6}$ alkenyl, $C_{2-6}$ alkynyl, aryl, aryl $C_{1-6}$ alkyl, a heterocyclyl group, a halogen atom, hydroxy, amino, carboxy, cyano and nitro. Preferable examples of the "optionally substituted $C_{1-6}$ alkylcarbonyloxy" include
acetyloxy,
isobutyryloxy,
pivaloyloxy,
hydroxyacetyloxy,
1-ethylbutyryloxy,
2-hydroxy-2-methylpropionyloxy,
3-hydroxypropionyloxy,
3-hydroxy-2,2-dimethylpropionyloxy,
3-acetoxy-2,2-dimethylpropionyloxy,
3-methoxy-2,2-dimethylpropionyloxy,
2'-aminopropionyloxy-2,2-dimethylpropionyloxy,
2,3-dihydroxypropionyloxy,
2,6-diaminohexanoyloxy,
2-amino-3-methylbutyryloxy,
2-aminopropionyloxy,
2-amino-3-hydroxypropionyloxy,
2-amino-3-phenylpropionyloxy,
aminoacetyloxy,
3-aminopropionyloxy,
3-carboxypropionyloxy,
and the like.

In the present specification, the "optionally substituted $C_{3-7}$ cycloalkylcarbonyloxy" means $C_{3-7}$ cycloalkylcarbonyloxy optionally substituted by 1-4 substituents selected from $C_{1-6}$ alkyl, $C_{1-6}$ alkoxy, $C_{3-7}$ cycloalkyl, $C_{2-6}$ alkenyl, $C_{2-6}$ alkynyl, aryl, aryl $C_{1-6}$ alkyl, a heterocyclyl group, a halogen atom, hydroxy, amino, carboxy, cyano and nitro. Preferable examples of the "optionally substituted $C_{3-7}$ cycloalkylcarbonyloxy" include cyclohexylcarbonyloxy, 4,4-difluorocyclohexylcarbonyloxy and the like.

In the present specification, the "optionally substituted $C_{1-6}$ alkoxycarbonyloxy" means $C_{1-6}$ alkoxycarbonyloxy optionally substituted by 1-4 substituents selected from $C_{1-6}$ alkyl, $C_{1-6}$ alkoxy, $C_{3-7}$ cycloalkyl, $C_{2-6}$ alkenyl, $C_{2-6}$ alkynyl, aryl, aryl $C_{1-6}$ alkyl, a heterocyclyl group, a halogen atom, hydroxy, amino, carboxy, cyano and nitro. Preferable examples of the "optionally substituted $C_{1-6}$ alkoxycarbonyloxy" include ethoxycarbonyloxy, 1-ethylpropyloxycarbonyloxy, 2,3-dihydroxypropyloxycarbonyloxy and the like.

In the present specification, the "optionally substituted heterocyclyl $C_{1-6}$ alkoxycarbonyloxy" means heterocyclyl $C_{1-6}$ alkoxycarbonyloxy optionally substituted by 1-4 substituents selected from $C_{1-6}$ alkyl, $C_{1-6}$ alkoxy, $C_{3-7}$ cycloalkyl, $C_{2-6}$ alkenyl, $C_{2-6}$ alkynyl, aryl, aryl $C_{1-6}$ alkyl, a heterocyclyl group, a halogen atom, hydroxy, amino, carboxy, cyano and nitro. Preferable examples of the "optionally substituted heterocyclyl $C_{1-6}$ alkoxycarbonyloxy" include (2,2-dimethyl-1,3-dioxolan-4-yl)methoxycarbonyloxy and the like.

In the present specification, the "optionally substituted $C_{1-6}$ alkylsulfonyl" means $C_{1-6}$ alkylsulfonyl optionally substituted by 1-4 substituents selected from $C_{1-6}$ alkylcarbonyloxy, $C_{1-6}$ alkoxy, $C_{3-7}$ cycloalkyl, $C_{2-6}$ alkenyl, $C_{2-6}$ alkynyl, aryl, a heterocyclyl group, a halogen atom, hydroxy, amino, carboxy, cyano and nitro. Preferable examples of the "optionally substituted $C_{1-6}$ alkylsulfonyl" include methanesulfonyl, 2-hydroxyethanesulfonyl, 2-aminoethanesulfonyl and the like.

In the present specification, the "optionally substituted heterocyclyloxy" means heterocyclyloxy optionally substituted by 1-4 substituents selected from $C_{1-6}$ alkyl optionally substituted by hydroxy, $C_{1-6}$ alkoxy, $C_{3-7}$ cycloalkyl, $C_{2-6}$ alkenyl, $C_{2-6}$ alkynyl, aryl, aryl $C_{1-6}$ alkyl, a heterocyclyl group, a halogen atom, hydroxy, amino, carboxy, cyano and nitro. Preferable examples of the "optionally substituted heterocyclyloxy" include 3,4,5-trihydroxy-6-hydroxymethyltetrahydropyran-2-yl and the like.

Compound (I) of the present invention or a pharmaceutically acceptable salt thereof is a prodrug to be converted to compound (B) by undergoing metabolism by hydrolysis and the like under physiological conditions after administration into the body. Compound (I) is considered to be converted to compound (B) by hydrolysis of ester group represented by $CO_2R^2$ by hydrolases such as esterase and the like under physiological conditions in vivo, followed by decarboxylation.

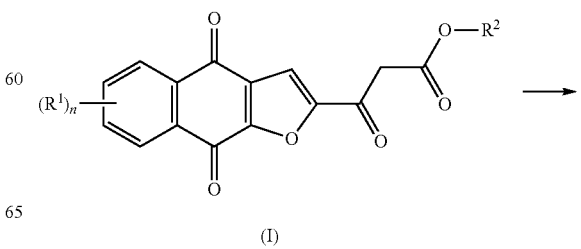

(I)

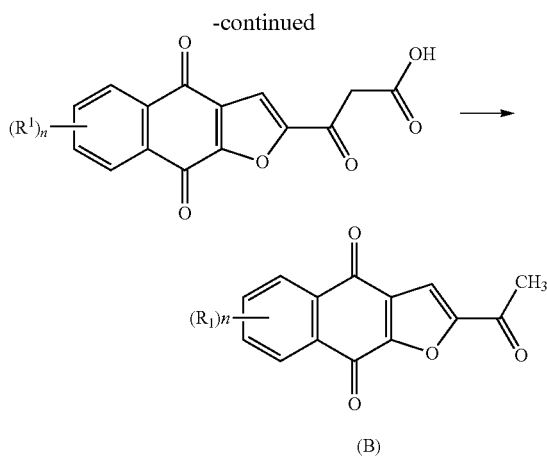

(B)

Therefore, the absorbability and persistence of compound (B) can be controlled by selecting, as a group represented by $R^2$, a group which is not easily hydrolyzed under pH environment or by a digestive enzyme in the gastrointestinal tract and, once absorbed, rapidly hydrolyzed by hydrolases such as esterase and the like in vivo. In addition, the intestinal absorbability can be improved by controlling the properties (water-solubility, liposolubility etc.) of compound (I) by introducing a functional group that improves water-solubility into a group represented by $R^2$, which further enables use as an injection.

From such aspects, a group for $R^2$ is
(1) $C_{1-6}$ alkyl optionally substituted by substituent(s) selected from hydroxy, optionally substituted amino, carboxy, a sulfonic acid group (sulfo group), a phosphoric acid group, a di $C_{1-6}$ alkyl phosphoric acid group, a heterocyclyl group, optionally substituted $C_{1-6}$ alkoxy, optionally substituted $C_{1-6}$ alkylcarbonyloxy, heterocyclylcarbonyloxy, $C_{3-7}$ cycloalkyloxycarbonyloxy and heterocyclyloxycarbonyloxy;
(2) $C_{2-6}$ alkynyl optionally substituted by substituent(s) selected from hydroxy, optionally substituted amino, carboxy, a sulfonic acid group (sulfo group), a phosphoric acid group and a heterocyclyl group;
(3) a heterocyclyl group optionally substituted by substituent(s) selected from hydroxy and optionally substituted $C_{1-6}$ alkyl; or
(4) aryl $C_{1-6}$ alkyl substituted by substituent(s) selected from hydroxy, optionally substituted amino, carboxy, a sulfonic acid group (sulfo group), a phosphoric acid group and a heterocyclyl group, is preferable, and
(1) $C_{1-6}$ alkyl optionally substituted by substituent(s) selected from hydroxy, optionally substituted $C_{1-6}$ alkoxy, optionally substituted $C_{1-6}$ alkylcarbonyloxy and heterocyclylcarbonyloxy;
(2) $C_{2-6}$ alkynyl optionally substituted by substituent(s) selected from optionally substituted amino and a heterocyclyl group; or
(3) a heterocyclyl group optionally substituted by optionally substituted $C_{1-6}$ alkyl, is more preferable.

In another embodiment of the group for $R^2$,
(1) $C_{1-6}$ alkyl optionally substituted by substituent(s) selected from hydroxy, optionally substituted amino, carboxy, a sulfonic acid group (sulfo group), a phosphoric acid group, a heterocyclyl group, optionally substituted $C_{1-6}$ alkylcarbonyloxy, heterocyclylcarbonyloxy, $C_{3-7}$ cycloalkyloxycarbonyloxy and heterocyclyloxycarbonyloxy;
(2) $C_{2-6}$ alkynyl optionally substituted by substituent(s) selected from hydroxy, optionally substituted amino, carboxy, a sulfonic acid group (sulfo group), a phosphoric acid group and a heterocyclyl group; or
(3) aryl $C_{1-6}$ alkyl substituted by substituent(s) selected from hydroxy, optionally substituted amino, carboxy, a sulfonic acid group (sulfo group), a phosphoric acid group and a heterocyclyl group, is preferable, and
(1) $C_{1-6}$ alkyl optionally substituted by substituent(s) selected from hydroxy, optionally substituted $C_{1-6}$ alkylcarbonyloxy, heterocyclylcarbonyloxy, $C_{3-7}$ cycloalkyloxycarbonyloxy and heterocyclyloxycarbonyloxy; or
(2) $C_{2-6}$ alkynyl optionally substituted by optionally substituted amino, is more preferable.

In still another embodiment of the group for $R^2$,
(1) $C_{1-6}$ alkyl optionally substituted by substituent(s) selected from hydroxy, optionally substituted amino, carboxy, a sulfonic acid group (sulfo group), a phosphoric acid group and a heterocyclyl group; or
(2) aryl $C_{1-6}$ alkyl substituted by substituent(s) selected from hydroxy, optionally substituted amino, carboxy, a sulfonic acid group (sulfo group), a phosphoric acid group and a heterocyclyl group, is preferable, though it is not limited as long as the above-mentioned object can be achieved.

As a group for $R^1$, a hydrogen atom is preferable.

The method for producing a prodrug of the present invention is preferably applied to compound (B), and also similarly preferably applied to compound (B'), but is not limited to these.

When compound (IA) or compound (I) contains optical isomer, stereoisomer, regio isomer, or rotamer, these are also included in compound (IA) or compound (I).

Compound (IA) and compound (I) have a β-ketoester structure in the structural formulas, and may be, in view of the properties thereof, an enol form tautomer represented by the following formula (I'A) or (I'). The tautomer represented by the formula (I'A) or (I'), or a salt thereof are also included in the compound of the present invention (IA) or compound (I).

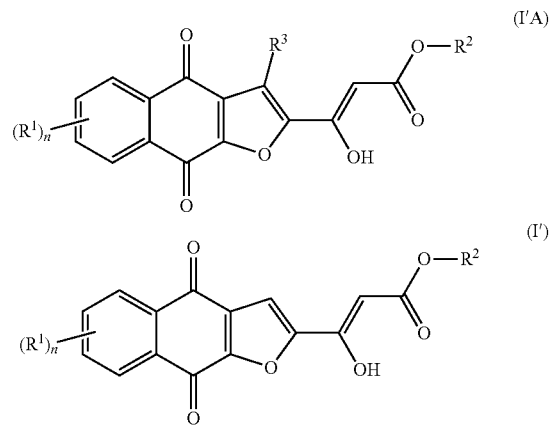

(wherein each symbol is as defined above.)

The salt of the tautomer represented by the above-mentioned formula (I'A) or (I') is not particularly limited and, for example, alkali metal salt; alkaline earth metal salt; salt with organic base; amino acid salt and the like can be mentioned. As the alkali metal salt, sodium salt, potassium salt, lithium salt and the like can be preferably mentioned, as the alkaline earth metal salt, magnesium salt, calcium salt and the like can be preferably mentioned, as the salt with organic base, N-methylmorpholine salt, ethanolamine salt, piperazine salt, diethylamine salt, triethylamine salt, tributylamine salt, tert-butylamine salt, diisopropylethylamine salt, dicyclohexylamine salt, N-methylpiperidine salt, meglumine salt, tromethamine salt, choline salt, benzathine salt, 4-phenylcyclohexylamine salt, pyridine salt, 4-pyrrolidinopyridine salt, picoline salt and the like can be preferably mentioned, and as the amino acid salt, glycine salt, lysine salt, arginine salt, ornithine salt, glutamic acid salt, aspartic acid salt and the like can be preferably mentioned.

Compound (IA) and compound (I) of the present invention can be converted to pharmaceutically acceptable salts thereof according to a method known per se. When the compound (I) of the present invention has an acidic group or basic group, it is reacted with a base or acid to give a basic salt or acidic salt.

A pharmaceutically acceptable "basic salt" of compound (IA) or compound (I) of the present invention is preferably an alkali metal salt such as sodium salt, potassium salt, and lithium salt; alkaline earth metal salt such as magnesium salt, and calcium salt; a salt with organic base such as N-methylmorpholine salt, ethanolamine salt, piperazine salt, diethylamine salt, triethylamine salt, tributylamine salt, tert-butylamine salt, diisopropylethylamine salt, dicyclohexylamine salt, N-methylpiperidine salt, meglumine salt, tromethamine salt, choline salt, benzathine salt, 4-phenylcyclohexylamine salt, pyridine salt, 4-pyrrolidinopyridine salt, and picoline salt or an amino acid salt such as glycine salt, lysine salt, arginine salt, ornithine salt, glutamic acid salt, and aspartic acid salt, preferably an alkali metal salt.

A pharmaceutically acceptable "acidic salt" of compound (IA) or compound (I) of the present invention is preferably inorganic acid salt such as hydrohalide (e.g., hydrofluoride, hydrochloride, hydrobromide, hydroiodide), nitrate, perchlorate, sulfate, phosphate and the like; organic acid salt such as lower alkanesulfonate (e.g., methanesulfonate, trifluoromethanesulfonate, ethanesulfonate), arylsulfonate (e.g., benzenesulfonate, p-toluenesulfonate), acetate, trifluoroacetate, malate, fumarate, succinate, citrate, ascorbate, tartrate, oxalate, maleate and the like; or amino acid salt such as glycine salt, lysine salt, arginine salt, ornithine salt, glutamic acid salt, aspartic acid salt, most preferably hydrohalide (particularly, hydrochloride).

A pharmaceutical composition containing compound (IA) or compound (I) of the present invention, or a pharmaceutically acceptable salt thereof and a pharmaceutically acceptable carrier and the like can be administered to mammals (e.g., mouse, rat, hamster, rabbit, cat, dog, bovine, sheep, monkey, human etc.). Examples of the carrier include excipient (e.g., starch, lactose, sugar, calcium carbonate, calcium phosphate etc.), binder (e.g., starch, gum arabic, carboxymethylcellulose, hydroxypropylcellulose, crystalline cellulose etc.), lubricant (e.g., magnesium stearate, talc etc.), disintegrant (e.g., carboxymethylcellulose, talc etc.) and the like.

After mixing the above-mentioned various components, the mixture can be formulated as preparations for oral administration such as capsule, tablet, fine granule, granule, dry syrup and the like, or for parenteral administration such as injection, suppository and the like by a means known per se.

While the content of compound (IA) or compound (I), or a pharmaceutically acceptable salt thereof in the pharmaceutical composition of the present invention varies depending on the form of the preparation, it is generally about 0.01-100 wt %, preferably about 0.1-50 wt %, further preferably about 0.5-20 wt %, relative to the whole preparation.

(Production Method)

The compound (IA) or compound (I) of the present invention can be produced utilizing the characteristics based on the kind of the basic skeleton or substituent, and applying various known production methods. Examples of the known method include the methods described in "ORGANIC FUNCTIONAL GROUP PREPARATIONS", 2nd edition, ACADEMIC PRESS, INC., 1989, "Comprehensive Organic Transformations", VCH Publishers Inc., 1989, and the like.

In this case, depending on the kind of the functional group, it is sometimes effective for the production techniques to protect the functional group with a suitable protecting group at the stage of a starting material or intermediate, or replace same with a group easily convertible to the functional group.

Examples of such functional group include amino group, hydroxy group, carboxyl group and the like and examples of the protecting group thereof include the protecting groups described in T. W. Greene and P. G. Wuts, "Protective Groups in Organic Synthesis (3rd ed., 1999)", from which an appropriate one can be selected and used according to the reaction conditions thereof. According to such method, a desired compound can be obtained by introducing the substituent, performing the reaction, and removing the protecting group as necessary, or converting to a desired group.

The production method of the compound of the present invention is described below. However, the production method is not at all limited by the following methods.

(Production Method 1)

In production method 1, a compound represented by the formula (Ia) (compound (Ia)) is produced by subjecting a compound represented by the formula (1) (compound (1)) to a method known per se to give a compound represented by the formula (2) (compound (2)) as an acid halide, and reacting the obtained compound (2) with a compound represented by the formula (3) (compound (3)).

Compound (1) to be used in this production method can be produced according to a method known per se (e.g., the methods described in patent documents 1-5, the method described in J. Med. Chem., 2012, 55, 7273-7284 etc.).

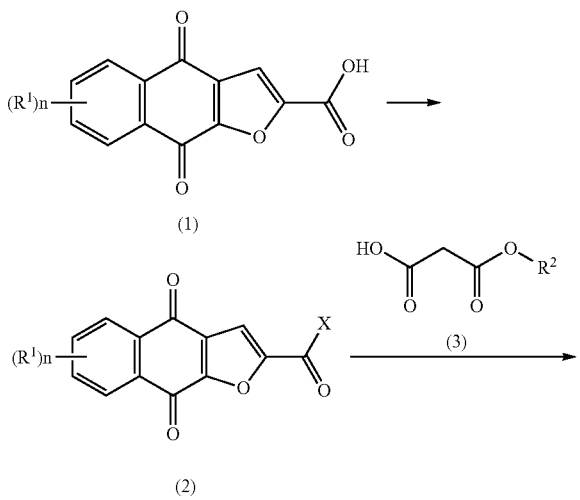

-continued

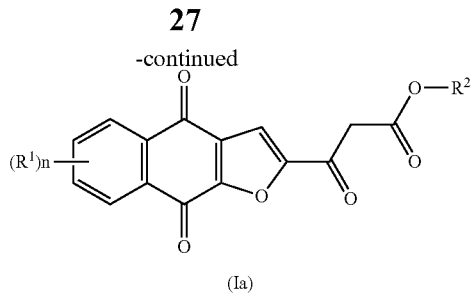

(Ia)

[wherein n, $R^1$ and $R^2$ are as defined above, and X is a halogen atom (fluorine atom, chlorine atom, bromine atom, iodine atom).]

In production method 1, the reaction of compound (2) and compound (3) is performed in the presence of a base such as magnesium chloride, triethylamine and the like, in an inert solvent. Compound (3) may be used not only in the form of a free acid but also as a salt such as potassium salt, sodium salt, lithium salt and the like.

The inert solvent to be used includes, for example, alcohols such as methanol, ethanol, propanol, 2-propanol and butanol; aromatic hydrocarbons such as benzene, toluene, and xylene; ethers such as diethyl ether, diisopropyl ether, tetrahydrofuran, 1,4-dioxane and 1,2-dimethoxyethane; amides such as N,N-dimethylformamide, N,N-dimethylacetamide, N-methyl-2-pyrrolidone, N-methylpyrrolidinone and hexamethylphosphoric triamide; halogenated hydrocarbons such as methylene chloride, chloroform, carbon tetrachloride, dichloroethane, chlorobenzene, o-dichlorobenzene, m-dichlorobenzene, fluorobenzene, trichloromethylbenzene and trifluoromethylbenzene; acetonitrile; and a mixture of these and the like.

While the reaction conditions such as reaction temperature, reaction time and the like vary depending on the reaction reagent, reaction solvent and the like to be used, they are generally −20 to 100° C. for 30 min to 20 hr.

The amount of compound (3) to be used is not particularly limited, and is generally 1-5 mol, preferably 1-3 mol, per 1 mol of compound (2), and the amounts of magnesium chloride and the base to be used are each generally 2-5 mol, preferably 2-3 mol, per 1 mol of compound (2). Compound (3) to be used in this production method can be produced according to a method known per se.

(Production Method 2)

In production method 2, compound (Ia) is produced by reacting a compound represented by the formula (4) (compound (4)) and a compound represented by the formula (5) (compound (5)).

Compound (4) to be used in this production method can be produced according to a method known per se (e.g., the methods described in patent documents 1-5 etc.).

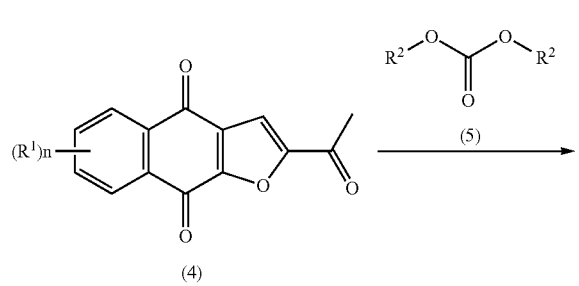

(4) (5)

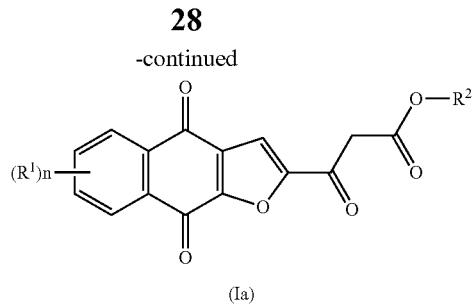

(Ia)

[wherein n, $R^1$ and $R^2$ are as defined above.]

In production method 2, the reaction of compound (4) and compound (5) is performed in the presence of a base such as sodium hydride and the like in an inert solvent.

The inert solvent to be used includes, for example, alcohols such as methanol, ethanol, propanol, 2-propanol and butanol; aromatic hydrocarbons such as benzene, toluene, and xylene; ethers such as diethyl ether, diisopropyl ether, tetrahydrofuran, 1,4-dioxane and 1,2-dimethoxyethane; amides such as N,N-dimethylformamide, N,N-dimethylacetamide, N-methyl-2-pyrrolidone, N-methylpyrrolidinone and hexamethylphosphoric triamide; halogenated hydrocarbons such as methylene chloride, chloroform, carbon tetrachloride, dichloroethane, chlorobenzene, o-dichlorobenzene, m-dichlorobenzene, fluorobenzene, trichloromethylbenzene and trifluoromethylbenzene; acetonitrile; and a mixture of these and the like.

While the reaction conditions such as reaction temperature, reaction time and the like vary depending on the reaction reagent, reaction solvent and the like to be used, they are generally −20 to 100° C. for 30 min to 20 hr.

The amount of compound (5) to be used is not particularly limited, and is generally 1-5 mol, preferably 1-3 mol, per 1 mol of compound (4), and the amount of the base such as sodium hydride and the like to be used is generally 1-5 mol, preferably 1-3 mol, per 1 mol of compound (4). Compound (5) to be used in this production method can be produced according to a method known per se.

(Production Method 3)

In production method 3, compound (Ia) is produced by reacting a compound represented by the formula (6) (compound (6)) and a compound represented by the formula (7) (compound (7)).

Compound (6) to be used in this production method can be produced according to a method known per se (e.g., the methods described in patent documents 1-5, the method described in J. Med. Chem., 2012, 55, 7273-7284 etc.).

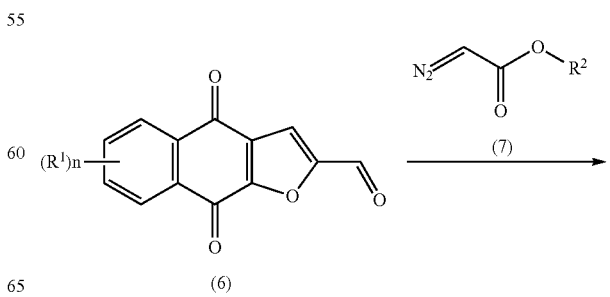

(6) (7)

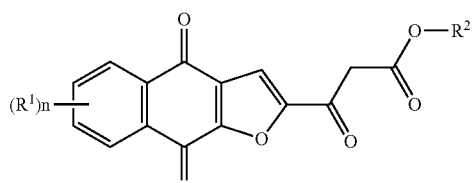

(Ia)

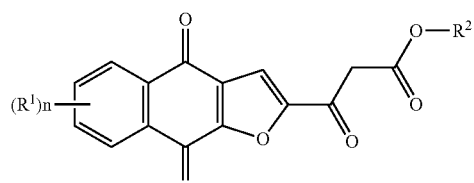

(Ia)

[wherein n, R¹ and R² are as defined above.]

In production method 3, the reaction of compound (6) and compound (7) is performed in the presence of Lewis acid and Meerwein reagent such as trimethyloxonium tetrafluoroborate or triethyloxonium tetrafluoroborate and the like in an inert solvent.

The inert solvent to be used includes, for example, alcohols such as methanol, ethanol, propanol, 2-propanol and butanol; aromatic hydrocarbons such as benzene, toluene, and xylene; ethers such as diethyl ether, diisopropyl ether, tetrahydrofuran, 1,4-dioxane and 1,2-dimethoxyethane; amides such as N,N-dimethylformamide, N,N-dimethylacetamide, N-methyl-2-pyrrolidone, N-methylpyrrolidinone and hexamethylphosphoric triamide; halogenated hydrocarbons such as methylene chloride, chloroform, carbon tetrachloride, dichloroethane, chlorobenzene, o-dichlorobenzene, m-dichlorobenzene, fluorobenzene, trichloromethylbenzene and trifluoromethylbenzene; acetonitrile; and a mixture of these and the like.

While the reaction conditions such as reaction temperature, reaction time and the like vary depending on the reaction reagent, reaction solvent and the like to be used, they are generally −20 to 100° C. for 30 min to 20 hr.

The amount of compound (7) to be used is not particularly limited, and is generally 1-5 mol, preferably 1-3 mol, per 1 mol of compound (6), and the amount of each of the Lewis acid and Meerwein reagent to be used is generally 0.05-2 mol, preferably 0.05-1 mol, per 1 mol of compound (6). Compound (7) to be used in this production method can be produced according to a method known per se.

(Production Method 4)

In production method 4, compound (Ia) is produced by reacting compound (2) and a compound represented by the formula (8) (compound (8)).

[wherein n, R¹, R² and X are as defined above.]

In production method 4, the reaction of compound (2) and compound (8) is performed in the presence of an organolithium compound such as n-butyllithium and the like, and an organic base such as diisopropylamine and the like in an inert solvent.

The inert solvent to be used includes, for example, alcohols such as methanol, ethanol, propanol, 2-propanol and butanol; aromatic hydrocarbons such as benzene, toluene, and xylene; ethers such as diethyl ether, diisopropyl ether, tetrahydrofuran, 1,4-dioxane and 1,2-dimethoxyethane; amides such as N,N-dimethylformamide, N,N-dimethylacetamide, N-methyl-2-pyrrolidone, N-methylpyrrolidinone and hexamethylphosphoric triamide; halogenated hydrocarbons such as methylene chloride, chloroform, carbon tetrachloride, dichloroethane, chlorobenzene, o-dichlorobenzene, m-dichlorobenzene, fluorobenzene, trichloromethylbenzene and trifluoromethylbenzene; acetonitrile; and a mixture of these and the like.

While the reaction conditions such as reaction temperature, reaction time and the like vary depending on the reaction reagent, reaction solvent and the like to be used, they are generally −80 to 20° C. for 30 min to 20 hr.

The amount of compound (8) to be used is not particularly limited, and is generally 1-5 mol, preferably 1-3 mol, per 1 mol of compound (2), the amount of the organolithium compound to be used is generally 1-3 mol, preferably 1-2 mol, per 1 mol of compound (2), and the amount of the organic base to be used is generally 1-5 mol, preferably 1-3 mol, per 1 mol of compound (2). Compound (8) to be used in this production method can be produced according to a method known per se.

(Production Method 5)

In production method 5, compound (Ia) of the present invention is produced by removing the protecting group of compound (Ic) having the protecting group, which can be produced according to production method 1 to production method 4.

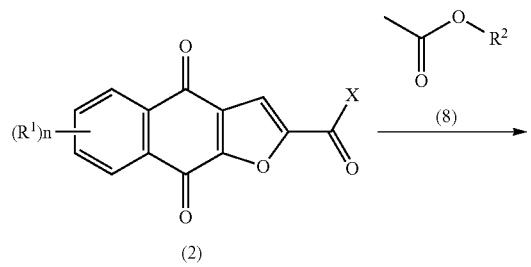

(2)

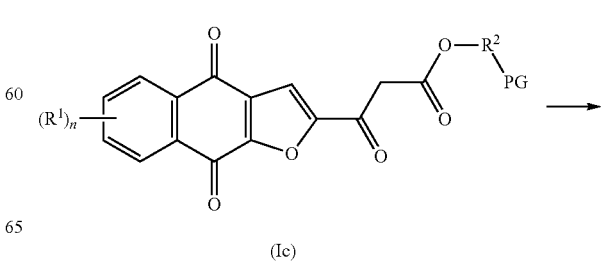

(Ic)

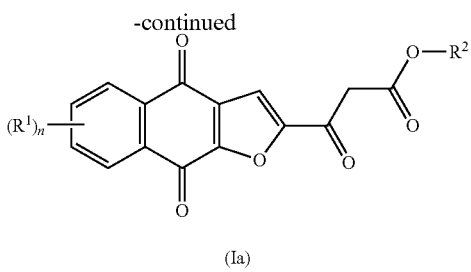

(Ia)

[wherein n, $R^1$ and $R^2$ are as defined above, and PG is a protecting group of $R^2$.]

In compound (Ic), $R^2$ is protected by a protecting group. In this step, the protecting group is removed. The deprotection method of each protecting group can be performed according to the method described in, for example, T. W. Greene and P. G. Wuts, "Protective Groups in Organic Synthesis (3rd ed., 1999)". [0119]

(Production Method 6)

In production method 6, compound (Ia) is produced by reacting compound (2) and compound (9) to give a compound represented by the formula (10) (compound (10)), and reacting compound (10) and a compound represented by the formula (11) (compound (11)).

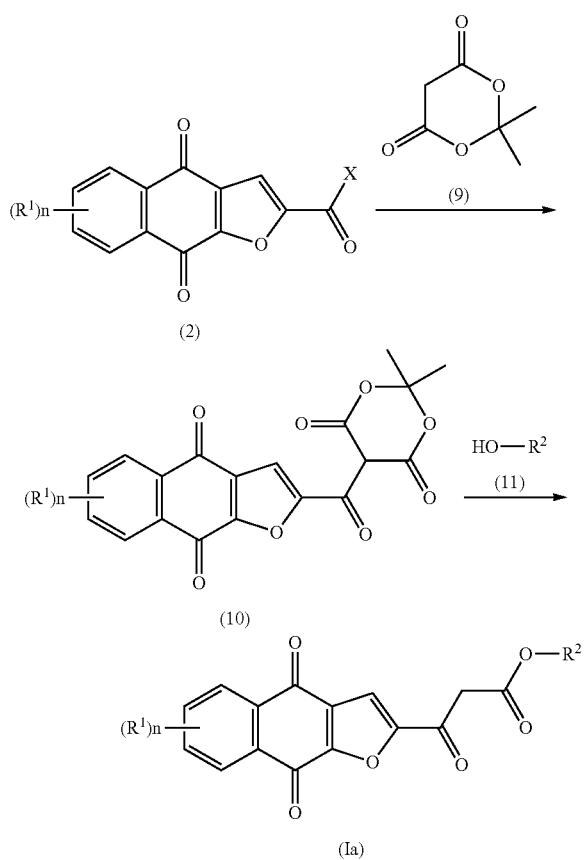

[wherein n, $R^1$, $R^2$ and X are as defined above.]

In production method 6, the reaction of compound (2) and compound (9) is performed in the presence of a base such as N,N-dimethylaminopyridine and the like in an inert solvent.

The inert solvent to be used includes, for example, alcohols such as methanol, ethanol, propanol, 2-propanol and butanol; aromatic hydrocarbons such as benzene, toluene, and xylene; ethers such as diethyl ether, diisopropyl ether, tetrahydrofuran, dioxane and 1,2-dimethoxyethane; amides such as N,N-dimethylformamide, N,N-dimethylacetamide, N-methyl-2-pyrrolidone, N-methylpyrrolidinone and hexamethylphosphoric triamide; halogenated hydrocarbons such as methylene chloride, chloroform, carbon tetrachloride, dichloroethane, chlorobenzene, o-dichlorobenzene, m-dichlorobenzene, fluorobenzene, trichloromethylbenzene and trifluoromethylbenzene; acetonitrile; and a mixture of these and the like.

While the reaction conditions such as reaction temperature, reaction time and the like vary depending on the reaction reagent, reaction solvent and the like to be used, they are generally −20 to 100° C. for 30 min to 20 hr.

The amount of compound (9) to be used is not particularly limited, and is generally 1-5 mol, preferably 1-3 mol, per 1 mol of compound (2), and the amount of the base to be used is generally 1-5 mol, preferably 2-3 mol, per 1 mol of compound (2).

In production method 6, the reaction of compound (10) and compound (11) is performed in an inert solvent.

The inert solvent to be used includes, for example, alcohols such as methanol, ethanol, propanol, 2-propanol and butanol; aromatic hydrocarbons such as benzene, toluene, and xylene; ethers such as diethyl ether, diisopropyl ether, tetrahydrofuran, dioxane and 1,2-dimethoxyethane; amides such as N,N-dimethylformamide, N,N-dimethylacetamide, N-methyl-2-pyrrolidone, N-methylpyrrolidinone and hexamethylphosphoric triamide; halogenated hydrocarbons such as methylene chloride, chloroform, carbon tetrachloride, dichloroethane, chlorobenzene, o-dichlorobenzene, m-dichlorobenzene, fluorobenzene, trichloromethylbenzene and trifluoromethylbenzene; acetonitrile; and a mixture of these and the like.

While the reaction conditions such as reaction temperature, reaction time and the like vary depending on the reaction reagent, reaction solvent and the like to be used, they are generally 0 to 150° C. for 10 min to 20 hr.

The amount of compound (11) to be used is not particularly limited, and is generally 1-5 mol, preferably 1-3 mol, per 1 mol of compound (10).

Compound (IA) of the present invention can also be produced from a starting compound having $R^3$, by a method similar to the above-mentioned production methods 1-6.

The compound (IA) or compound (I) of the present invention produced above can be isolated and purified by a known method, for example, extraction, precipitation, distillation, chromatography, fractional recrystallization, recrystallization and the like.

When the compound (IA) or compound (I) of the present invention or an intermediate in the production thereof has an asymmetric carbon, optical isomers are present. These optical isomers can be each isolated and purified by a conventional method such as fractional recrystallization (salt resolution) for recrystallization with an appropriate salt, column chromatography and the like. The above-mentioned isomers can also be produced by asymmetric synthesis. As a reference document of a method of resolving an optical isomer of the above-mentioned isomer from a racemate, J. Jacques et al, "Enantiomers, Racemates and Resolution, John Wiley And Sons, Inc." can be mentioned.

While the dose of compound (IA) or compound (I), or a pharmaceutically acceptable salt thereof of the present invention varies depending on the subject of administration, symptoms, and other factors, a single dose of about 1-500 mg is given about 1-3 times per day for oral administration to an adult, for example, a cancer patient.

Compound (IA) or compound (I), or a pharmaceutically acceptable salt thereof of the present invention are prodrug compounds having high solubility and high oral absorbability, which are converted, after administration, to compound (B') or compound (B) having a particularly superior anticancer action on cancer cells and capable of inducing apoptosis of cancer stem cells, and show superior persistence. They are useful as anticancer agents, or agents for the prophylaxis or treatment of cancer metastasis and/or cancer recurrence.

While the kind of cancer to be the prophylaxis or treatment target is not particularly limited, they are useful for the prophylaxis or treatment of, for example, breast cancer, head and neck cancer, lung cancer, ovarian cancer, pancreatic cancer, colonrectal cancer, prostate cancer, esophageal cancer, nasopharyngeal cancer, pituitary cancer, gallbladder cancer, thyroid cancer, salivary gland cancer, urinary bladder cancer, renal cell carcinoma, melanoma, hepatoma, cervical cancer, endometrial carcinoma, Kaposi's sarcoma, Ewing's sarcoma, medulloblastoma, sarcoma, brain tumor, gastric cancer, multiple myeloma, leukemia, lymphoma and the like, and have a particularly superior apoptosis inducing action on the cancer stem cells of these.

Compound (IA) or compound (I), or a pharmaceutically acceptable salt thereof of the present invention can be used in combination with other medicaments, for example, existing anticancer agents, as long as the efficacy thereof is not impaired. In this case, the administration period is not limited, and these can be administered simultaneously, or may be administered at different times, to the subject of administration. As the dose, a clinically-used dose can be appropriately selected as the standard. The mixing ratio of compound (IA) or compound (I), or a pharmaceutically acceptable salt thereof of the present invention or the like and a concomitant drug can be appropriately selected according to the subject of administration, administration route, target disease, symptom, combination and the like.

Examples of the existing anticancer agent include chemotherapeutic agent, hormonal therapeutic agent, immunotherapeutic agent, molecular targeted drug and the like.

As the "chemotherapeutic agent", alkylating agent, metabolic antagonist, antitumor antibiotic, plant-derived antitumor drug and the like are used.

As the "alkylating agent", nitrogen mustard, nitrogen mustard-N-oxide hydrochloride, chlorambucil, cyclophosphamide, ifosfamide, thiotepa, carboquone, improsulfan tosylate, busulfan, nimustine hydrochloride, mitobronitol, melphalan, dacarbazine, ranimustine, estramustine phosphate sodium, triethylenemelamine, carmustine, lomustine, streptozocin, pipobroman, etoglucid, carboplatin, cisplatin, miboplatin, nedaplatin, oxaliplatin, altretamine, ambamustine, dibrospidium hydrochloride, fotemustine, prednimustine, pumitepa, ribomustin, temozolomide, treosulphan, trofosfamide, zinostatin stimalamer, adozelesin, cystemustine, bizelesin, and DDS preparations thereof and the like are used.

As the "metabolic antagonist", mercaptopurine, 6-mercaptopurine riboside, thioinosine, methotrexate, pemetrexed, enocitabine, cytarabine, cytarabine ocfosfate, ancitabine hydrochloride, 5-FU drug (e.g., fluorouracil, tegafur, UFT, doxifluridine, carmofur, gallocitabine, emitefur, capecitabine), aminopterin, nelzarabine, leucovorin calcium, tabloid, butocine, folinate calcium, levofolinate calcium, cladribine, emitefur, fludarabine, gemcitabine, hydroxycarbamide, pentostatin, piritrexim, idoxuridine, mitoguazone, tiazofurine, ambamustine, bendamustine, and DDS preparations thereof and the like are used.

As the "antitumor antibiotic", actinomycin D, actinomycin C, mitomycin C, chromomycin A3, bleomycin hydrochloride, bleomycin sulfate, peplomycin sulfate, daunorubicin hydrochloride, doxorubicin hydrochloride, aclarubicin hydrochloride, pirarubicin hydrochloride, epirubicin hydrochloride, neocarzinostatin, mithramycin, sarcomycin, carzinophilin, mitotane, zorubicin hydrochloride, mitoxantrone hydrochloride, idarubicin hydrochloride, and DDS preparations thereof and the like are used.

As the "plant-derived antitumor drug", etoposide, etoposide phosphate, vinblastine sulfate, vincristine sulfate, vindesine sulfate, teniposide, paclitaxel, docetaxel, vinorelbine, and DDS preparations thereof and the like are used.

As the "hormonal therapeutic agent", fosfestrol, diethylstilbestrol, chlorotrianisene, medroxyprogesterone acetate, megestrol acetate, chlormadinone acetate, cyproterone acetate, danazol, allylestrenol, gestrinone, mepartricin, raloxifene, ormeloxifene, levormeloxifene, anti-estrogen (e.g., tamoxifen citrate, toremifene citrate), pill preparation, mepitiostane, testololactone, aminoglutethimide, LH-RH agonist (e.g., goserelin acetate, buserelin, leuprorelin), droloxifene, epitiostanol, ethinylestradiol sulfonate, aromatase inhibitor (e.g., fadrozole hydrochloride, anastrozole, letrozole, exemestane, vorozole, formestane), anti-androgen (e.g., flutamide, bicalutamide, nilutamide), 5α-reductase inhibitor (e.g., finasteride, epiristeride), adrenocorticohormone drug (e.g., dexamethasone, prednisolone, betamethasone, triamcinolone), androgen synthesis inhibitor (e.g., abiraterone), retinoid and drugs that retard retinoid metabolism (e.g., liarozole) and the like are used.

As the "immunotherapeutic agent", biological response modifier (e.g., picibanil, krestin, schizophyllan, lentinan, ubenimex, interferon, interleukin, macrophagecolony stimulating factor, granulocyte colony stimulating factor, erythropoietin, lymphotoxin, BCG vaccine, *Corynebacterium parvum*, levamisole, polysaccharide K, procodazole, anti-CTLA4 antibody) and the like are used.

As the "molecular targeted drug", tositumomab, ibritumomab, alemtuzumab, axitinib, bevacizumab, afatinib, bortezomib, bosutinib, carfilzomib, cetuximab, dasatinib, denosumab, edrecolomab, erlotinib, everolimus, vismodegib, gefitinib, gemtuzumab ozogamicin, imatinib, ipilimumab, lapatinib, lenalidomide, nilotinib, nimotuzumab, olaparib, panitumumab, pazopanib, pertuzumab, rituximab, siltuximab, sorafenib, sunitinib, tamibarotene, temsirolimus, thalidomide, trastuzumab, tretinoin, vandetanib, vorinostat, cabozantinib, trametinib, dabrafenib, alectinib, ceritinib, ibrutinib, palbociclib, regorafenib and the like are used.

EXAMPLES

The present invention is explained in detail in the following by referring to Examples, which are not to be construed as limitative.

Example 1

Isobutyl 3-(4,9-Dioxo-4,9-dihydro-naphtho[2,3-b]furan-2-yl)-3-oxo-propionate (1a) 4,9-Dioxo-4,9-dihydro-naphtho[2,3-b]furan-2-carbonyl Chloride

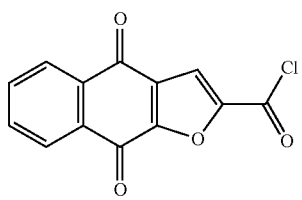 [SMILES: O=C(Cl)c1cc2c(o1)C(=O)c1ccccc1C2=O]

4,9-Dioxo-4,9-dihydro-naphtho[2,3-b]furan-2-carboxylic acid (150 mg, 0.62 mmol) synthesized by the method described in J. Med. Chem., 2012, 55, 7273-7284 was suspended in methylene chloride (6 mL), oxalyl chloride (0.06 mL, 0.70 mmol), and then one drop of N,N-dimethylformamide were added thereto at room temperature, and the mixture was stirred at room temperature for 30 min. The solvent in the reaction mixture was evaporated under reduced pressure to give 4,9-dioxo-4,9-dihydro-naphtho[2,3-b]furan-2-carbonyl chloride as a yellow powder (160 mg, yield 99%).

$^1$H-NMR (CDCl$_3$, 400 MHz) δ:7.69 (1H, s), 7.87-7.96 (2H, m), 8.09-8.18 (2H, m).

(1b) Isobutyl 3-(4,9-Dioxo-4,9-dihydro-naphtho[2,3-b]furan-2-yl)-3-oxo-propionate

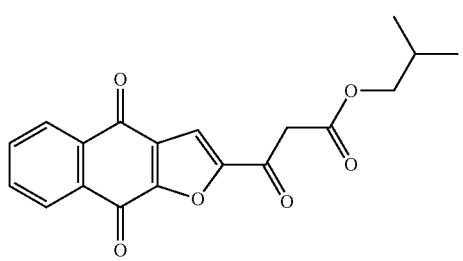 [SMILES: CC(C)COC(=O)CC(=O)c1cc2c(o1)C(=O)c1ccccc1C2=O]

Monoisobutyl malonate (200 mg, 1.25 mmol) was dissolved in acetonitrile (3 mL), triethylamine (0.28 mL, 2.0 mmol) and then magnesium chloride (150 mg, 1.6 mmol) were added thereto under ice-cooling, and the mixture was stirred under a nitrogen stream at room temperature for 1.5 hr. To the obtained solution were added, under ice-cooling, a solution of the compound (165 mg, 0.633 mmol) of Example 1(1a) in methylene chloride (4.5 mL)-acetonitrile (1.5 mL), and then triethylamine (0.19 mL, 1.4 mmol), and the mixture was stirred at 60° C. for 2 hr. To the reaction mixture were added ethyl acetate and water, and the mixture was acidified with 6M hydrochloric acid. After separation into two layers, the ethyl acetate layer was washed with saturated brine, and dried over anhydrous sodium sulfate. The solvent was evaporated under reduced pressure, and the obtained powder was purified by silica gel column chromatography (n-hexane:ethyl acetate, 10:1→47:1, V/V), and the solvent in the object fraction was evaporated under reduced pressure. To the obtained residue was added n-hexane, and the mixture was collected by filtration to give isobutyl 3-(4,9-dioxo-4,9-dihydro-naphtho[2,3-b]furan-2-yl)-3-oxo-propionate as a yellow powder (147 mg, yield 70%).

$^1$H-NMR (DMSO-d$_6$, 400 MHz) δ: 0.86 (5.4H, d, J=6.7 Hz), 0.93 (0.6H, d, J=6.7 Hz), 1.81-1.92 (0.9H, m), 1.92-2.03 (0.1H, m), 3.89 (1.8H, d, J=6.7 Hz), 4.00 (0.2H, d, J=6.7 Hz), 4.23 (1.8H, s), 6.02 (0.1H, s), 7.72 (0.1H, s), 7.85-7.96 (2H, m), 8.08-8.18 (2H, m), 8.16 (0.9H, s). MS (ESI) m/z: 363 (M+Na)$^+$.

According to Example 1, the compounds of Examples 2-5 were synthesized.

Example 2

Ethyl 3-(4,9-Dioxo-4,9-dihydro-naphtho[2,3-b]furan-2-yl)-3-oxo-propionate

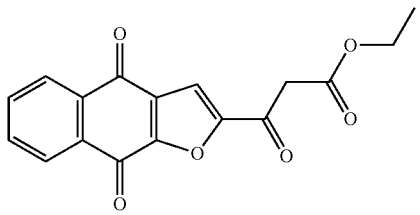 [SMILES: CCOC(=O)CC(=O)c1cc2c(o1)C(=O)c1ccccc1C2=O]

$^1$H-NMR (DMSO-d$_6$, 400 MHz) δ: 1.20 (2.7H, t, J=7.1 Hz), 1.28 (0.3H, t, J=7.1 Hz), 4.14 (1.8H, q, J=7.1 Hz), 4.20 (1.8H, s), 4.25 (0.2H, q, J=7.1 Hz), 6.00 (0.1H, s), 7.74 (0.1H, s), 7.87-7.96 (2H, m), 8.09-8.19 (2H, m), 8.15 (0.9H, s), 11.90-12.10 (0.1H, br).

MS (ESI) m/z: 335 (M+Na)$^+$.

Example 3

Phenyl 3-(4,9-Dioxo-4,9-dihydro-naphtho[2,3-b]furan-2-yl)-3-oxo-propionate

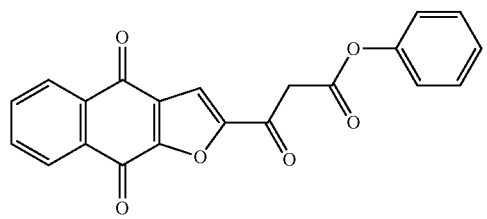 [SMILES: O=C(CC(=O)c1cc2c(o1)C(=O)c1ccccc1C2=O)Oc1ccccc1]

$^1$H-NMR (DMSO-d$_6$, 400 MHz) δ: 4.50 (1.8H, s), 6.22 (0.1H, s), 6.70-6.77 (0.2H, m), 7.13-7.20 (1.8H, m), 7.21-7.33 (1.2H, m), 7.39-7.47 (1.8H, m), 7.81 (0.1H, s), 7.88-7.96 (2H, m), 8.09-8.19 (2H, m), 8.23 (0.9H, s), 11.05-11.90 (0.1H, br). MS (ESI) m/z: 383 (M+Na)$^+$.

Example 4

Benzyl 3-(4,9-Dioxo-4,9-dihydro-naphtho[2,3-b]furan-2-yl)-3-oxo-propionate

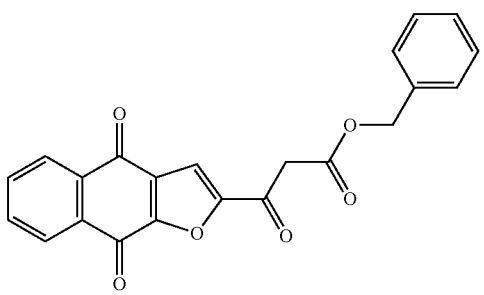 [SMILES: O=C(CC(=O)c1cc2c(o1)C(=O)c1ccccc1C2=O)OCc1ccccc1]

$^1$H-NMR (DMSO-d$_6$, 400 MHz) δ: 4.29 (1.8H, s), 5.18 (1.8H, s), 5.28 (0.2H, s), 6.07 (0.1H, s), 7.26-7.46 (5H, m), 7.74 (0.1H, s), 7.87-7.97 (2H, m), 8.10-8.20 (2H, m), 8.15 (0.9H, s), 11.82-11.94 (0.1H, br).
MS (ESI) m/z: 397 (M+Na)$^+$.

Example 5

2-Hydroxyethyl 3-(4,9-Dioxo-4,9-dihydro-naphtho[2,3-b]furan-2-yl)-3-oxo-propionate

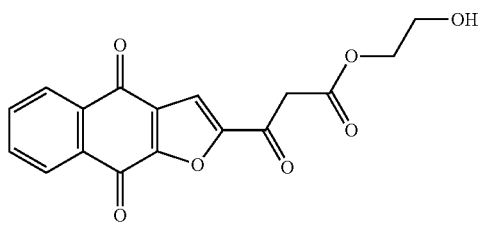 [SMILES: O=C(CC(=O)c1cc2c(o1)C(=O)c1ccccc1C2=O)OCCO]

$^1$H-NMR (DMSO-d$_6$, 400 MHz) δ: 3.52-3.70 (2H, m), 4.00-4.15 (2H, m), 4.22 (1.8H, s), 4.81 (1H, t, J=5.4 Hz), 6.01 (0.1H, s), 7.73 (0.1H, s), 7.88-7.96 (2H, m), 8.10-8.17 (2.9H, m), 11.83-12.02 (0.1H, br).
MS (ESI) m/z: 351 [M+Na]

Example 6

4-Piperidyl 3-(4,9-Dioxo-4,9-dihydro-naphtho[2,3-b]furan-2-yl)-3-oxo-propionate Hydrochloride (6a) tert-Butyl 4-[3-(4,9-Dioxo-4,9-dihydro-naphtho[2,3-b]furan-2-yl)-3-oxo-propionyloxy]piperidine-1-carboxylate

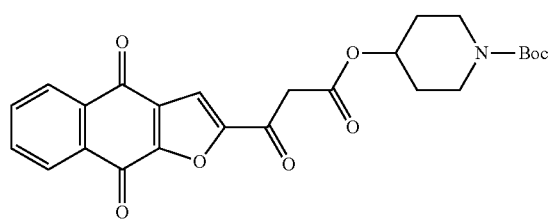 [SMILES: CC(C)(C)OC(=O)N1CCC(OC(=O)CC(=O)c2cc3c(o2)C(=O)c2ccccc2C3=O)CC1]

According to Example 1, tert-butyl 4-[3-(4,9-dioxo-4,9-dihydro-naphtho[2,3-b]furan-2-yl)-3-oxo-propionyloxy]piperidine-1-carboxylate was synthesized.
$^1$H-NMR (DMSO-d$_6$, 400 MHz) δ: 1.36 (8.1H, s), 1.40 (0.9H, s), 1.43-1.54 (2H, m), 1.72-1.83 (2H, m), 3.14-3.24 (2H, m), 3.43-3.53 (2H, m), 4.20 (1.8H, s), 4.88-4.97 (0.9H, m), 5.06-5.16 (0.1H, m), 6.01 (0.1H, s), 7.73 (0.1H, s), 7.87-7.96 (2H, m), 8.09-8.18 (2H, m), 8.14 (0.9H, s).

(6b) 4-Piperidyl 3-(4,9-Dioxo-4,9-dihydro-naphtho[2,3-b]furan-2-yl)-3-oxo-propionate Hydrochloride

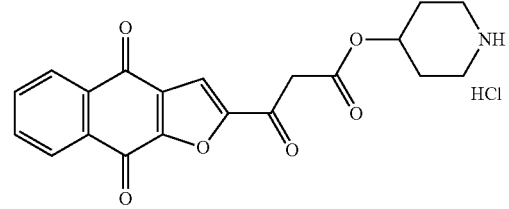 [SMILES: O=C(CC(=O)c1cc2c(o1)C(=O)c1ccccc1C2=O)OC1CCNCC1 ; Cl]

The compound of Example 6(6a) (302 mg, 0.643 mmol) was suspended in formic acid (3 mL), 8.3 M hydrogen chloride isopropanol solution (0.31 mL, 2.6 mmol) was added thereto at 0° C., and the mixture was stirred at the same temperature for 10 min. Ethyl acetate (15 mL) was added and the mixture was stirred at the same temperature for 1 hr. The precipitate was collected by filtration, and washed with ethanol (3 mL) to give 4-piperidyl 3-(4,9-dioxo-4,9-dihydro-naphtho[2,3-b]furan-2-yl)-3-oxo-propionate hydrochloride as a yellow powder (188 mg, yield 72%).
$^1$H-NMR (DMSO-d$_6$, 400 MHz) δ: 1.72-1.87 (2H, m), 1.94-2.09 (2H, m), 3.01-3.15 (4H, m), 4.25 (1.8H, s), 4.95-5.06 (0.9H, m), 5.06-5.16 (0.1H, m), 6.02 (0.1H, s), 7.72 (0.1H, s), 7.88-7.98 (2H, m), 8.10-8.20 (2H, m), 8.17 (0.9H, s), 8.60-8.98 (2.1H, br).
MS (ESI) m/z: 368 (M+H)$^+$.

Example 7

2-Carboxyethyl 3-(4,9-Dioxo-4,9-dihydro-naphtho[2,3-b]furan-2-yl)-3-oxo-propionate (7a) 2-Benzyloxycarbonylethyl 3-(4,9-Dioxo-4,9-dihydro-naphtho[2,3-b]furan-2-yl)-3-oxo-propionate

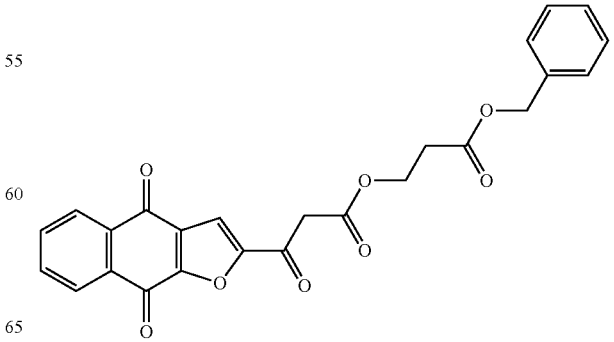

According to Example 1, 2-benzyloxycarbonylethyl 3-(4,9-dioxo-4,9-dihydro-naphtho[2,3-b]furan-2-yl)-3-oxo-propionate was synthesized.

¹H-NMR (CDCl₃, 400 MHz) δ: 2.73 (0.3H, t, J=6.1 Hz), 2.78 (1.7H, t, J=6.1 Hz), 3.98 (0.3H, s), 4.48 (0.3H, t, J=6.1 Hz), 4.53 (1.7H, t, J=6.1 Hz), 5.13 (0.3H, s), 5.18 (1.7H, s), 5.95 (0.85H, s), 7.25 (0.85H, s), 7.30-7.44 (5H, m), 7.65 (0.15H, s), 7.73-7.84 (2H, m), 8.16-8.29 (2H, m), 11.87 (0.85H, s).

(7b) 2-Carboxyethyl 3-(4,9-Dioxo-4,9-dihydro-naphtho[2,3-b]furan-2-yl)-3-oxo-propionate

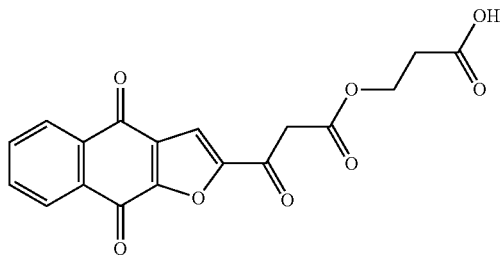 [SMILES: O=C(O)CCOC(=O)CC(=O)c1cc2c(o1)C(=O)c1ccccc1C2=O]

The compound of Example 7(7a) (462 mg, 0.914 mmol) was dissolved in a mixed solution of methanol (40 mL) and tetrahydrofuran (16 mL), 10% Pd—C (64 mg) was added thereto and the mixture was subjected to catalytic hydrogenation at 0.2 MPa at room temperature for 20 min. Pd—C was filtered off, and the solvent was evaporated under reduced pressure. The obtained residue was purified by silica gel column chromatography (chloroform:methanol, 100:1, V/V) and the solvent in the object fraction was evaporated under reduced pressure. Ethyl acetate (8 mL) was added to the obtained powder, and the powder was collected by filtration to give 2-carboxyethyl 3-(4,9-dioxo-4,9-dihydro-naphtho[2,3-b]furan-2-yl)-3-oxo-propionate as a yellow powder (220 mg, yield 68%).

¹H-NMR (DMSO-d₆, 400 MHz) δ: 2.57 (1.8H, t, J=6.1 Hz), 2.67 (0.2H, t, J=6.1 Hz), 4.20 (1.8H, s), 4.27 (1.8H, t, J=6.1 Hz), 4.37 (0.2H, t, J=6.1 Hz), 5.98 (0.1H, s), 7.75 (0.1H, s), 7.87-7.97 (2H, m), 8.09-8.19 (2H, m), 8.13 (0.9H, s), 12.20-12.50 (1.1H, br).

MS (ESI) m/z: 379 (M+Na)⁺.

Example 8

2-Pyridylmethyl 3-(4,9-Dioxo-4,9-dihydro-naphtho[2,3-b]furan-2-yl)-3-oxo-propionate

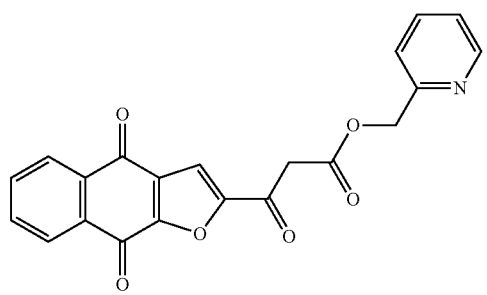 [SMILES: O=C(CC(=O)c1cc2c(o1)C(=O)c1ccccc1C2=O)OCc1ccccn1]

According to Example 1, the title compound was synthesized.

¹H-NMR (DMSO-d₆, 400 MHz) δ: 4.35 (1.8H, s), 5.25 (1.8H, s), 5.35 (0.2H, s), 6.11 (0.1H, s), 7.30-7.39 (1H, m), 7.41-7.46 (0.9H, m), 7.46-7.51 (0.1H, m), 7.75 (0.1H, s), 7.78-7.88 (1H, m), 7.88-7.96 (2H, m), 8.10-8.18 (2H, m), 8.19 (0.9H, s), 8.51-8.56 (0.9H, m), 8.56-8.59 (0.1H, m).

MS (ESI) m/z: 398 (M+Na)⁺.

Example 9

4-Tetrahydropyranyl 3-(4,9-Dioxo-4,9-dihydro-naphtho[2,3-b]furan-2-yl)-3-oxo-propionate

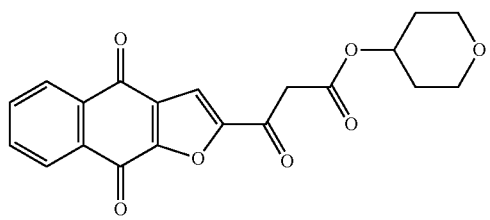 [SMILES: O=C(CC(=O)c1cc2c(o1)C(=O)c1ccccc1C2=O)OC1CCOCC1]

According to Example 1, the title compound was synthesized.

¹H-NMR (DMSO-d₆, 400 MHz) δ: 1.48-1.60 (1.8H, m), 1.60-1.68 (0.2H, m), 1.80-1.89 ((1.8H, m), 1.89-1.98 (0.2H, m), 3.41-3.50 (2H, m), 3.68-3.79 (1.8H, m), 3.80-3.88 (0.2H, m), 4.21 (1.8H, s), 4.89-5.00 (0.9H, m), 5.01-5.11 (0.1H, m), 6.02 (0.1H, s), 7.74 (0.1H, s), 7.88-7.97 (2H, m), 8.10-8.19 (2H, m), 8.15 (0.9H, s), 11.70-12.10 (0.1H, br).

MS (ESI) m/z: 391 (M+Na)⁺.

Example 10 tert-Butyl 3-(4,9-Dioxo-4,9-dihydro-naphtho[2,3-b]furan-2-yl)-3-oxo-propionate

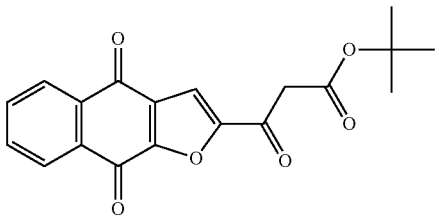 [SMILES: CC(C)(C)OC(=O)CC(=O)c1cc2c(o1)C(=O)c1ccccc1C2=O]

According to Example 1, the title compound was synthesized.

¹H-NMR (DMSO-d₆, 400 MHz) δ: 1.41 (5.4H, s), 1.52 (3.6H, s), 4.07 (1.2H, s), 5.91 (0.4H, s), 7.71 (0.4H, s), 7.86-7.97 (2H, m), 8.07-8.19 (2H, m), 8.10 (0.6H, s), 12.09 (0.4H, s).

MS (ESI) m/z: 363 (M+Na)⁺.

Example 11

2,2-Dimethyl[1,3]dioxolan-4-ylmethyl 3-(4,9-Dioxo-4,9-dihydro-naphtho[2,3-b]furan-2-yl)-3-oxo-propionate (11a) 2-(2,2-Dimethyl-4,6-dioxo-[1,3]dioxane-5-carbonyl)naphtho[2,3-b]furan-4,9-dione

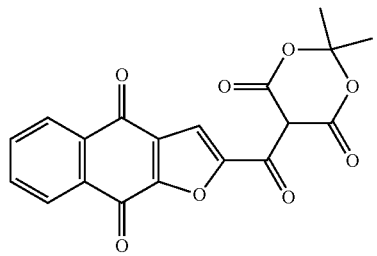 [SMILES: CC1(C)OC(=O)C(C(=O)c2cc3c(o2)C(=O)c2ccccc2C3=O)C(=O)O1]

Meldrum's acid (2.00 g, 13.9 mmol) was dissolved in methylene chloride (60 mL), N,N-dimethylaminopyridine (3.00 g, 24.6 mmol) was added thereto and the mixture was cooled to −10° C. A solution of the compound of Example 1(1a) (3.23 g, 12.4 mmol) in methylene chloride (120 mL) was added dropwise at not more than −5° C. over 30 min, and the mixture was stirred at room temperature for 1.5 hr. The solvent was evaporated under reduced pressure, ethyl acetate was added to the obtained residue and the residue was collected by filtration. To the obtained powder was added chloroform (500 mL), and the mixture was washed successively with 1.5 M hydrochloric acid (150 mL), water (150 mL) and saturated brine (200 mL), and dried over anhydrous sodium sulfate. The solvent was evaporated under reduced pressure. To the obtained residue was added diethyl ether and the residue was collected by filtration to give a yellow powder (3.93 g). The obtained powder (400 mg) was suspended in ethyl acetate (10 mL), and the suspension was heated to about 70° C. and stirred at room temperature for 30 min. The insoluble material was collected by filtration to give 2-(2,2-dimethyl-4,6-dioxo-[1,3]dioxane-5-carbonyl)naphtho[2,3-b]furan-4,9-dione as a yellow powder (350 mg).

$^1$H-NMR (DMSO-$d_6$, 400 MHz) δ: 1.61 (6H, s), 7.01 (1H, s), 7.83-7.93 (2H, m), 8.04-8.16 (2H, m).

(11b) 2,2-Dimethyl[1,3]dioxolan-4-ylmethyl 3-(4,9-Dioxo-4,9-dihydro-naphtho[2,3-b]furan-2-yl)-3-oxo-propionate

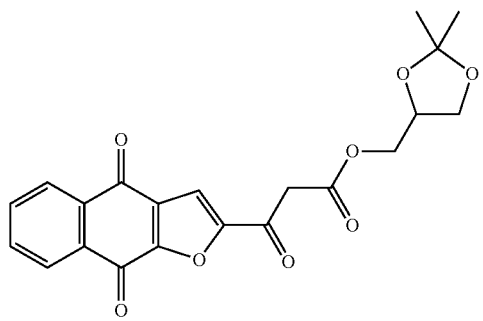 [SMILES: CC1(C)OCC(COC(=O)CC(=O)c2cc3c(o2)C(=O)c2ccccc2C3=O)O1]

The compound of Example 11(11a) (800 mg, 2.17 mmol) and 2,2-dimethyl-1,3-dioxolan-4-methanol (1.43 g, 10.8 mmol) were suspended in tetrahydrofuran (25 mL), and the suspension was stirred at 60° C. for 2 hr. The suspension was allowed to cool, water was added to the reaction mixture, and the mixture was extracted twice with methylene chloride. The organic layers were combined, washed with saturated brine, and dried over anhydrous sodium sulfate. The solvent was evaporated under reduced pressure, and the obtained residue was purified by column chromatography (ethyl acetate:chloroform, 0:10→10:90, V/V). The solvent in the object fraction was evaporated under reduced pressure to give a yellow powder (567 mg). To the obtained powder was added t-butyl methyl ether (10 mL), and the mixture was stirred at room temperature for 15 min. The insoluble material was collected by filtration. To the obtained powder was added t-butyl methyl ether (6 mL) again, and the insoluble material was collected by filtration to give 2,2-dimethyl[1,3]dioxolan-4-ylmethyl 3-(4,9-dioxo-4,9-dihydro-naphtho[2,3-b]furan-2-yl)-3-oxo-propionate as a yellow powder (438 mg, yield 51%).

$^1$H-NMR (DMSO-$d_6$, 400 MHz) δ: 1.22-1.28 (6H, m), 3.63-3.80 (1H, m), 3.95-4.04 (1H, m), 4.05-4.13 (1H, m), 4.15-4.30 (3.8H, m), 6.02 (0.1H, s), 7.75 (0.1H, s), 7.87-7.95 (2H, m), 8.08-8.17 (2.9H, m), 11.70-11.90 (0.1H, br).

MS (ESI) m/z: 421 (M+Na)$^+$.

Example 12

3-(4,9-Dioxo-4,9-dihydro-naphtho[2,3-b]furan-2-yl)-3-oxo-propionyloxymethyl 2,2-Dimethylpropionate (12a) Mono(2,2-dimethylpropionyloxymethyl) malonate

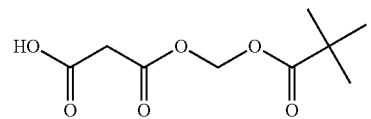

Monobenzyl malonate (2.00 g, 10.3 mmol), chloromethyl pivalate (1.55 g, 10.3 mmol), sodium iodide (1.54 g, 10.3 mmol) and potassium carbonate (1.71 g, 12.4 mmol) were suspended in N,N-dimethylformamide (20 mL), and the suspension was stirred at room temperature for 1.5 hr. Water was added to the reaction mixture, and the mixture was extracted twice with ethyl acetate. The organic layers were combined and washed twice with water and once with saturated brine, and dried over anhydrous sodium sulfate. The solvent was evaporated under reduced pressure, and the obtained residue was purified by column chromatography (n-hexane:ethyl acetate, 9:1→47:3, V/V). The solvent in the object fraction was evaporated under reduced pressure to give benzyl 2,2-dimethylpropionyloxymethyl malonate as a colorless oil (1.05 g, yield 33%).

$^1$H-NMR (CDCl$_3$, 400 MHz) δ: 1.16-1.21 (9H, m), 3.47 (2H, s), 5.12-5.18 (2H, m), 5.70-5.82 (2H, m), 7.28-7.40 (5H, m).

10% Pd—C (105 mg) was wetted with toluene (0.2 mL), a solution of benzyl 2,2-dimethylpropionyloxymethyl malonate (1.05 g, 3.41 mmol) in methanol (30 mL) was added, and the mixture was subjected to catalytic hydrogenation at 0.3 MPa at room temperature for 30 min. The insoluble material in the reaction mixture was filtered off through celite, the solvent in the filtrate was evaporated under reduced pressure and the residue was dissolved in ethyl acetate. The solvent was evaporated under reduced pressure to give mono(2,2-dimethylpropionyloxymethyl) malonate as a pale black oil (709 mg, yield 95%).

$^1$H-NMR (CDCl$_3$, 400 MHz) δ: 1.18-1.23 (9H, m), 3.48 (2H, s), 5.75-5.83 (2H, m).

(12b) 3-(4,9-Dioxo-4,9-dihydro-naphtho[2,3-b]furan-2-yl)-3-oxo-propionyloxymethyl 2,2-Dimethylpropionate

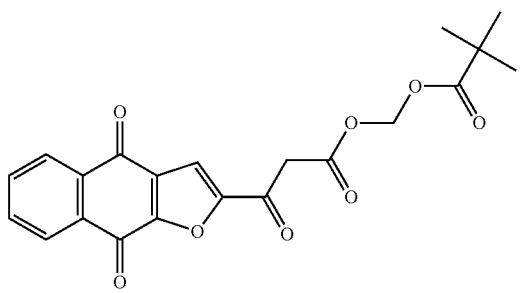 [SMILES: CC(C)(C)C(=O)OCOC(=O)CC(=O)c1cc2c(o1)C(=O)c1ccccc1C2=O]

The compound of Example 12(12a) (709 mg, 3.25 mmol) was dissolved in acetonitrile (8.5 mL), triethylamine (0.78 mL, 5.6 mmol) and then magnesium chloride (407 mg, 4.27 mmol) were added thereto under ice-cooling, and the mixture was stirred under a nitrogen stream at room temperature for 2.5 hr. To the obtained solution were added a solution of the compound of Example 1(1a) (446 mg, 1.71 mmol) in methylene chloride (17 mL) and then triethylamine (0.52 mL, 3.7 mmol) under ice-cooling, and the mixture was stirred at 60° C. for 30 min. Under ice-cooling, water was added to the reaction mixture, and the mixture was acidified with 6 M hydrochloric acid and extracted with ethyl acetate. The organic layer was washed with saturated brine, dried over anhydrous sodium sulfate, and the solvent was evaporated under reduced pressure. The obtained powder was purified by silica gel column chromatography (n-hexane:ethyl acetate, 6:4→ethyl acetate:chloroform, 25:75, V/V), and the solvent in the object fraction was evaporated under reduced pressure. To the obtained residue was added t-butylmethylether, and the residue was collected by filtration to give 3-(4,9-dioxo-4,9-dihydro-naphtho[2,3-b]furan-2-yl)-3-oxo-propionyloxymethyl 2,2-dimethylpropionate as a yellow powder (358 mg, yield 53%).

$^1$H-NMR (DMSO-d$_6$, 400 MHz) δ: 1.12-1.18 (9H, m), 4.31 (1.8H, s), 5.75 (1.8H, m), 5.85 (0.2H, m), 5.99 (0.1H, s), 7.76 (0.1H, s), 7.87-7.96 (2H, m), 8.09-8.18 (2.9H, m), 11.52-11.77 (0.1H, br). MS (ESI) m/z: 421 (M+Na)$^+$.

Example 13

2-Hydroxyethyl 3-(4,9-dioxo-4,9-dihydro-naphtho[2,3-b]furan-2-yl)-3-hydroxy-acrylate Ethanolamine Salt

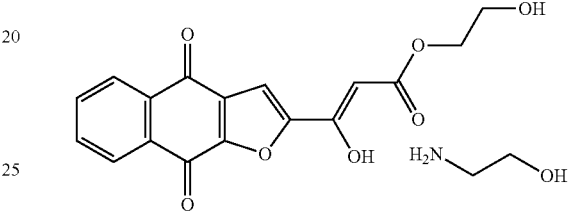

The compound of Example 5 (1.00 g, 3.05 mmol) was suspended in ethyl acetate (150 mL), ethanolamine (1.84 mL, 30.5 mmol) was added thereto and the mixture was stirred at room temperature for 40 min. The insoluble material was collected by filtration, and washed successively with ethyl acetate and ethanol to give 2-hydroxyethyl 3-(4,9-dioxo-4,9-dihydro-naphtho[2,3-b]furan-2-yl)-3-hydroxy-acrylate ethanolamine salt as a red powder (1.13 g, yield 95%).

$^1$H-NMR (DMSO-d$_6$, 400 MHz) δ: 2.82 (2H, t, J=5.5 Hz), 3.51-3.59 (4H, m), 3.86-3.96 (2H, m), 4.05-4.30 (1H, br), 5.11 (1H, s), 7.05 (1H, s), 7.80-7.98 (2H, m), 8.03-8.18 (2H, m). MS (ESI) m/z: 351 (M+Na)$^+$.

Examples 14-154 shown in the following Table 1-1-Table 1-23 were synthesized according to Examples 1, 6, 7, 11, 12 and 13.

TABLE 1-1

| Ex. No. | structure | data |
|---|---|---|
| Ex. 14 | (structure shown) | $^1$H-NMR (DMSO-d$_6$, 400 MHz) δ: 3.60-3.75 (2H, m), 4.20-4.38 (3.8H, m), 4.47 (1.8H, s), 4.54 (0.2H, s), 5.99-6.04 (0.1H, m), 7.18-7.36 (5H, m), 7.74-7.78 (0.1H, m), 7.89-7.96 (2H, m), 8.11-8.20 (2.9H, m), 11.87-11.92 (0.1H, br). MS (ESI) m/z: 441 [M + Na]$^+$ |

TABLE 1-1-continued

| Ex. No. | structure | data |
|---|---|---|
| Ex. 15 | 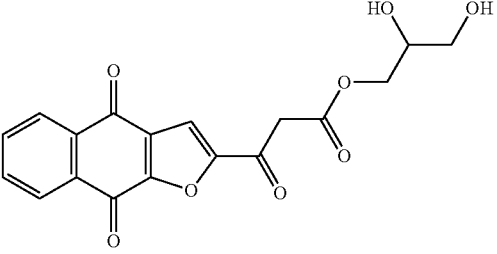 [SMILES: O=C(CC(=O)c1cc2c(o1)C(=O)c1ccccc1C2=O)OCC(O)CO] | ¹H-NMR (DMSO-d₆, 400 MHz) δ: 3.23-3.36 (2H, m), 3.59-3.77 (1H, m), 3.95-4.27 (3.8H, m), 4.43-5.26 (2H, br), 6.01 (0.1H, s), 7.73 (0.1H, s), 7.87-7.98 (2H, m), 8.08-8.18 (2.9H, m), 11.83-11.97 (0.1H, br). MS (ESI) m/z: 381 [M + Na]⁺ |
| Ex. 16 | 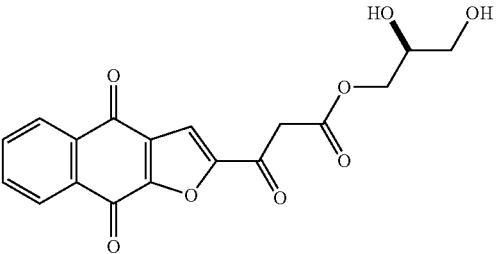 [SMILES: O=C(CC(=O)c1cc2c(o1)C(=O)c1ccccc1C2=O)OC[C@@H](O)CO] | ¹H-NMR (DMSO-d₆, 400 MHz) δ: 3.28-3.40 (2H, m), 3.60-3.77 (1H, m), 3.95-4.02 (1H, m), 4.10-4.15 (1H, m), 4.21 (1.8H, s), 4.63 (1H, t, J = 5.6 Hz), 4.90 (1H, d, J = 5.1 Hz), 6.01 (0.1H, s), 7.73 (0.1H, s), 7.87-7.98 (2H, m), 8.09-8.19 (2.9H, m), 11.80-11.92 (0.1H, br). MS (ESI) m/z: 381 [M + Na]⁺ |
| Ex. 17 | 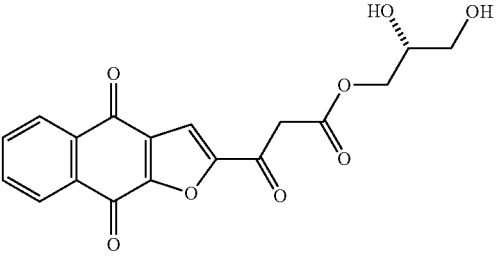 [SMILES: O=C(CC(=O)c1cc2c(o1)C(=O)c1ccccc1C2=O)OC[C@H](O)CO] | ¹H-NMR (DMSO-d₆, 400 MHz) δ: 3.28-3.40 (2H, m), 3.60-3.77 (1H, m), 3.95-4.02 (1H, m), 4.10-4.15 (1H, m), 4.21 (1.8H, s), 4.62 (1H, t, J = 5.6 Hz), 4.90 (1H, d, J = 5.1 Hz), 6.01 (0.1H, s), 7.73 (0.1H, s), 7.87-7.98 (2H, m), 8.09-8.19 (2.9H, m), 11.80-12.00 (0.1H, br). MS (ESI) m/z: 381 [M + Na]⁺ |
| Ex. 18 | 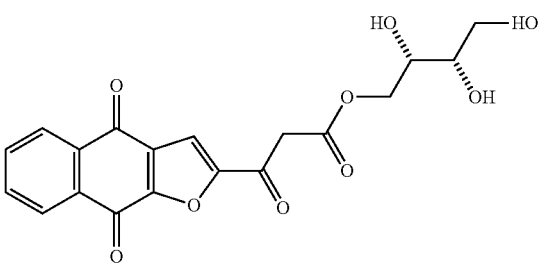 [SMILES: O=C(CC(=O)c1cc2c(o1)C(=O)c1ccccc1C2=O)OC[C@H](O)[C@@H](O)CO] | ¹H-NMR (DMSO-d₆, 400 MHz) δ: 3.53 (3H, m), 3.64-3.85 (1H, m), 4.03-4.16 (2H, m), 4.20 (1.8H, s), 4.40-4.73 (3H, m), 5.99 (0.1H, s), 7.72 (0.1H, s), 7.86-7.98 (2H, m), 8.09-8.18 (2.9H, m), 11.70-12.03 (0.1H, br). MS (ESI) m/z: 411 [M + Na]⁺ |
| Ex. 19 | 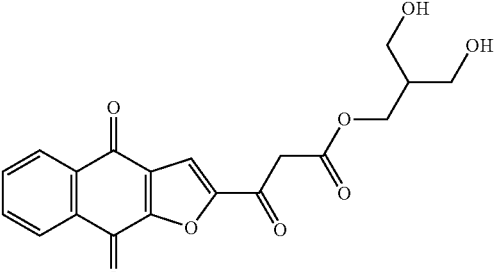 | ¹H-NMR (DMSO-d₆, 400 MHz) δ: 1.77-1.88 (1H, m), 3.32-3.56 (4H, m), 4.11 (2H, d, J = 5.9 Hz), 4.20 (1.8H, s), 4.36-4.67 (2H, br), 5.98 (0.1H, s), 7.70 (0.1H, s), 7.86-7.97 (2H, m), 8.07-8.19 (2.9H, m), 11.78-12.00 (0.1H, br). MS (ESI) m/z: 395 [M + Na]⁺ |

TABLE 1-2

| Ex. No. | structure | data |
|---|---|---|
| Ex. 20 | 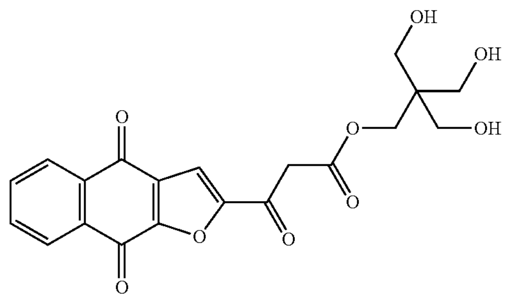 [SMILES: O=C(CC(=O)c1cc2c(o1)C(=O)c1ccccc1C2=O)OCC(CO)(CO)CO] | $^1$H-NMR (DMSO-d$_6$, 400 MHz) δ: 3.31-3.48 (6H, m), 4.02 (1.8H, s), 4.13-4.20 (2H, m), 4.27-4.63 (3H, m), 5.94 (0.1H, s), 7.67 (0.1H, s), 7.87-7.96 (2H, m), 8.09-8.18 (2.9H, m), 11.60-12.07 (0.1H, br). MS (ESI) m/z: 401 [M − H]$^-$ |
| Ex. 21 | 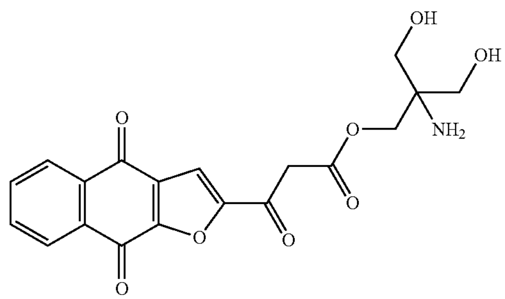 [SMILES: NC(CO)(CO)COC(=O)CC(=O)c1cc2c(o1)C(=O)c1ccccc1C2=O] | $^1$H-NMR (DMSO-d$_6$, 400 MHz) δ: 3.49-3.64 (4H, m), 4.18-4.33 (3.8H, s), 5.36-5.54 (2H, br), 5.99 (0.1H, s), 7.63 (0.1H, s), 7.88-7.98 (2H, m), 8.00-8.23 (5.9H, m). MS (ESI) m/z: 388 [M + H]$^+$ |
| Ex. 22 | 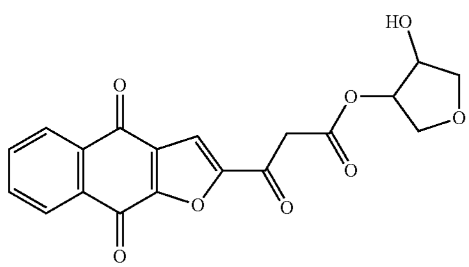 [SMILES: O=C(CC(=O)c1cc2c(o1)C(=O)c1ccccc1C2=O)OC1COCC1O] | $^1$H-NMR (DMSO-d$_6$, 400 MHz) δ: 3.38-3.54 (1H, m), 3.64-3.78 (1H, m), 3.78-3.90 (1H, m), 3.92-4.02 (1H, m), 4.16-4.40 (2.8H, m), 5.10-5.25 (2H, m), 6.04 (0.1H, s), 7.72 (0.1H, s), 7.87-7.96 (2H, m), 8.09-8.17 (2.9H, m), 11.40-12.20 (0.1H, br). MS (ESI) m/z: 393 [M + Na]$^+$ |
| Ex. 23 | 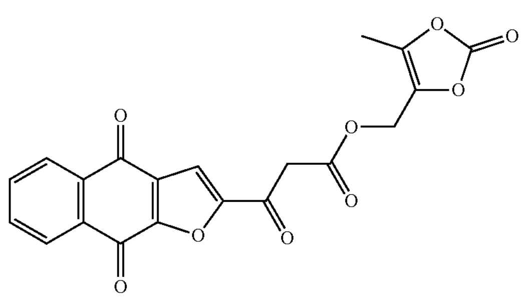 [SMILES: Cc1oc(=O)oc1COC(=O)CC(=O)c1cc2c(o1)C(=O)c1ccccc1C2=O] | $^1$H-NMR (DMSO-d$_6$, 400 MHz) δ: 2.16 (2.7H, s), 2.21 (0.3H, s), 4.28 (1.8H, s), 5.06 (1.8H, s), 5.14 (0.2H, s), 6.01 (0.1H, s), 7.75 (0.1H, s), 7.88-7.96 (2H, m), 8.09-8.16 (2.9H, m), 11.60-11.75 (0.1H, s). MS (ESI) m/z: 419 [M + Na]$^+$ |
| Ex. 24 | 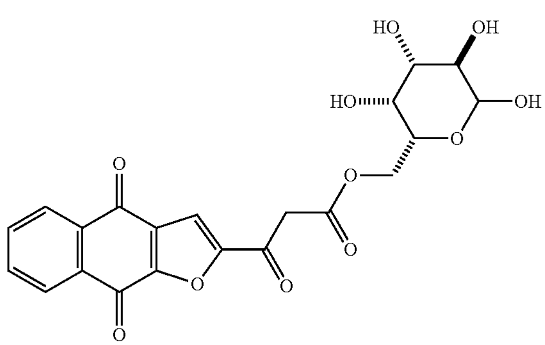 | $^1$H-NMR (DMSO-d$_6$, 400 MHz) δ: 3.40-4.49 (7.8H, m), 5.07-5.19 (0.8H, m), 5.98-6.03 (0.2H, m), 7.67-7.72 (0.2H, m), 7.93-7.99 (2H, m), 8.12-8.25 (2.8H, m), 12.08 (0.2H, s). MS (ESI) m/z: 469 [M + Na]$^+$ |

TABLE 1-2-continued

| Ex. No. | structure | data |
|---|---|---|
| Ex. 25 | (naphtho[2,3-b]furan-4,9-dione with 3-oxo-propanoate ester of morpholinyl-acetate) | $^1$H-NMR (DMSO-$d_6$, 400 MHz) δ: 3.38-3.50 (2H, m), 3.59-3.77 (6H, m), 4.17 (0.4H, s), 4.82 (0.4H, s), 4.88 (1.6H, s), 6.13 (0.8H, s), 7.43 (0.8H, s), 7.73 (0.2H, s), 7.75-7.84 (2H, m), 8.16-8.27 (2H, m), 11.74-11.86 (0.8H, br).<br>MS (ESI) m/z: 434 [M + Na]$^+$ |
| Ex. 26 | (naphtho[2,3-b]furan-4,9-dione with 3-oxo-propanoate ester of piperidinyl-acetate) | $^1$H-NMR (DMSO-$d_6$, 400 MHz) δ: 1.38-1.64 (6H, m), 3.27-3.40 (4H, m), 4.29 (1.7H, s), 4.86 (1.7H, s), 4.97 (0.3H, s), 6.06 (0.15H, s), 7.76 (0.15H, s), 7.88-7.96 (2H, m), 8.09-8.22 (2.85H, m), 11.73-11.84 (0.15H, br).<br>MS (ESI) m/z: 432 [M + Na]$^+$ |

TABLE 1-3

| Ex. No. | structure | data |
|---|---|---|
| Ex. 27 | (naphtho[2,3-b]furan-4,9-dione with 3-oxo-propanoate ester of 2-hydroxy-3-hydroxypropanoate / glyceric acid ester) | $^1$H-NMR (DMSO-$d_6$, 400 MHz) δ: 3.70-3.84 (2H, m), 3.89-4.20 (1.8H, m), 4.94-5.08 (1H, m), 5.88-6.01 (0.1H, br), 7.63-7.71 (0.1 H, m), 7.86-7.97 (2H, m), 8.08-8.20 (2.9H, m).<br>Ms (ESI) m/z: 395 [M + Na]$^+$ |
| Ex. 28 | (naphtho[2,3-b]furan-4,9-dione with diglycinyl glycerol diester, 2HCl) | $^1$H-NMR (DMSO-$d_6$, 400 MHz) δ: 3.76-3.94 (4H, m), 4.25-4.52 (5.8H, m), 5.32-5.47 (1H, m), 5.99 (0.1H, s), 7.73 (0.1H, s), 7.74-7.85 (2H, m), 8.18-8.28 (2.9H, m), 8.36-8.57 (6H, m), 11.45-11.92 (0.1H, br). |

TABLE 1-3-continued

| Ex. No. | structure | data |
|---|---|---|
| Ex. 29 | 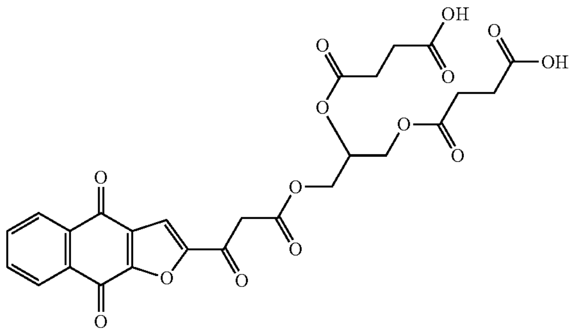 [SMILES: O=C(O)CCC(=O)OCC(COC(=O)CC(=O)c1cc2c(o1)C(=O)c1ccccc1C2=O)OC(=O)CCC(=O)O] | ¹H-NMR (DMSO-d₆, 400 MHz) δ: 2.38-2.58 (8H, m), 4.13-4.34 (5.8H, m), 5.13-5.29 (1H, m), 6.01 (0.1H, s), 1H, s), 7.75 (0.1H, s), 7.87-7 97 (2H, m), 8.09-8.19 (2.9H, m), 11.68-11.78 (0.1H, br), 12.03-12.37 (2H, br). MS (ESI) m/z: 581 [M + Na]⁺ |
| Ex. 30 | 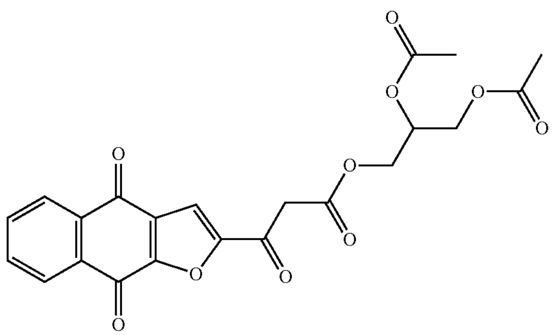 [SMILES: CC(=O)OCC(COC(=O)CC(=O)c1cc2c(o1)C(=O)c1ccccc1C2=O)OC(C)=O] | ¹H-NMR (DMSO-d₆, 400 MHz) δ: 1.97-2.09 (6H, m), 4.07-4.47 (6H, m), 5.10-5.27 (1H, m), 5.98 (0.1H, s), 7.73 (0.1H, s), 7.88-7.96 (2H, m), 8.10-8.20 (2.9H, m), 11.70-11.80 (0.1H, br). MS (ESI) m/z: 465 [M + Na]⁺ |
| Ex. 31 | 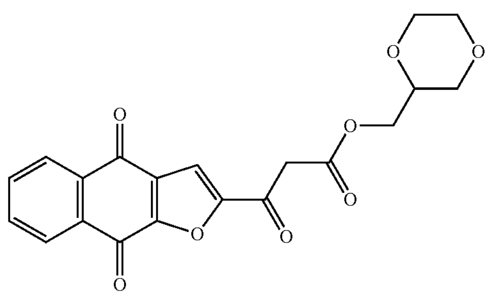 [SMILES: O=C(CC(=O)c1cc2c(o1)C(=O)c1ccccc1C2=O)OCC1COCCO1] | ¹H-NMR (DMSO-d₆, 400 MHz) δ: 3.24-3.84 (7H, m), 4.00-4.20 (2H, m), 4.25 (1.8H, s), 6.03 (0.1H, s), 7.74 (0.1H, s), 7.87-7.96 (2H, m), 8.09-8.17 (2.9H, m), 11.71-11.88 (0.1H, br). MS (ESI) m/z: 407 [M + Na]⁺ |
| Ex. 32 | 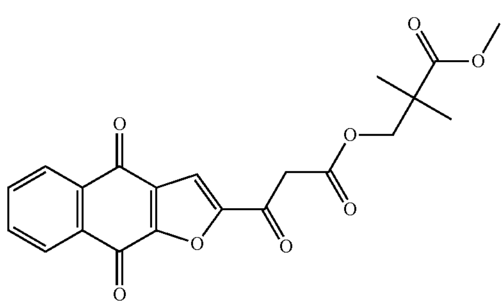 [SMILES: COC(=O)C(C)(C)COC(=O)CC(=O)c1cc2c(o1)C(=O)c1ccccc1C2=O] | ¹H-NMR (DMSO-d₆, 400 MHz) δ: 1.12 (5.4H, s), 1.22 (0.6H, s), 3.57 (2.7H, s), 3.64 (0.3H, s), 4.13 (1.8H, m), 4.20-4.24 (2H, m), 5.98 (0.1H, s), 7.73 (0.1H, s), 7.87-7.96 (2H, m), 8.09-8.18 (2.9H, m), 11.75-11.88 (0.1H, br). MS (ESI) m/z: 421 [M + Na]⁺ |

TABLE 1-4

| Ex. No. | structure | data |
|---|---|---|
| Ex. 33 | 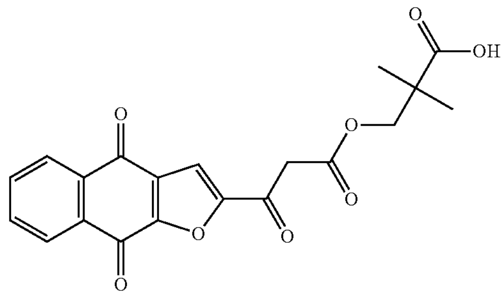 [SMILES: CC(C)(COC(=O)CC(=O)c1cc2c(o1)C(=O)c1ccccc1C2=O)C(=O)O] | $^1$H-NMR (DMSO-d$_6$, 400 MHz) δ: 1.09 (5.4H, s), 1.19 (0.6H, s), 4.10 (1.8H, s), 4.21 (2H, s), 6.00 (0.1H, s), 7.74 (0.1H, s), 7.87-7.96 (2H, m), 8.09-8.17 (2.9H, m), 12.29-12.44 (0.1H, br). MS (ESI) m/z: 407 [M + Na] $^+$ |
| Ex. 34 | 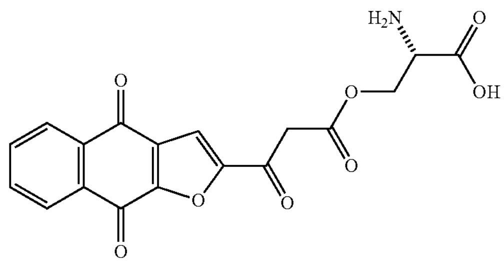 [SMILES: N[C@@H](COC(=O)CC(=O)c1cc2c(o1)C(=O)c1ccccc1C2=O)C(=O)O] | $^1$H-NMR (DMSO-d$_6$ + TFA, 400 MHz) δ: 4.19-4.32 (1.8H, m), 4.35-4.52 (2H, m), 4.54-4.63 (1H, m,), 5.96 (0.1H, s), 7.66 (0.1H, s), 7.86-7.97 (2H, m), 8.09-8.20 (2.9H, m), 8.42-8.57 (3H, br). MS (ESI) m/z: 372 [M + H] $^+$ |
| Ex. 35 | 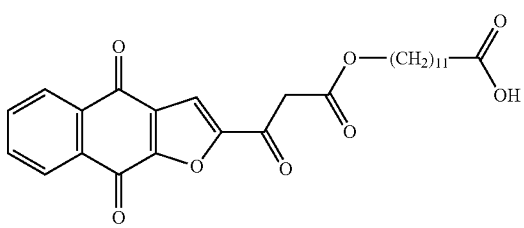 | $^1$H-NMR (DMSO-d$_6$, 400 MHz) δ: 1.11-1.29 (14H, m), 1.40-1.58 (4H, m), 2.16 (2H, t, J = 7.3 Hz), 4.08 (2H, t, J = 6.3 Hz), 4.19 (1.8H, s), 5.99 (0.1H, s), 7.72 (0.1H, s), 7.87-7.98 (2H, m), 8.09-8.17 (2.9H, m), 11.83-12.07 (0.1H, s). MS (ESI) m/z: 505 [M + Na] $^+$ |
| Ex. 36 | 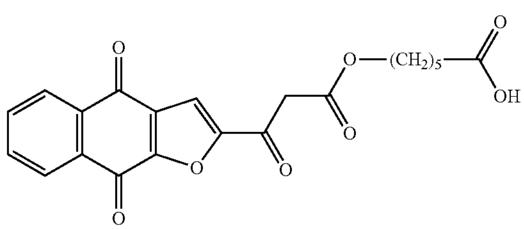 | $^1$H-NMR (DMSO-d$_6$, 400 MHz) δ: 1.24-1.42 (2H, m), 1.43-1.71 (4H, m), 2.13-2.26 (2H, m), 4.01-4.13 (2H, m), 4.21 (1.8H, s), 5.99 (0.1H, s), 7.72 (0.1H, s), 7.87-7.95 (2H, m), 8.09-8.17 (2.9H, m), 11.92-12.00 (1.1H, m). MS (ESI) m/z: 421 [M + H] $^+$ |
| Ex. 37 | 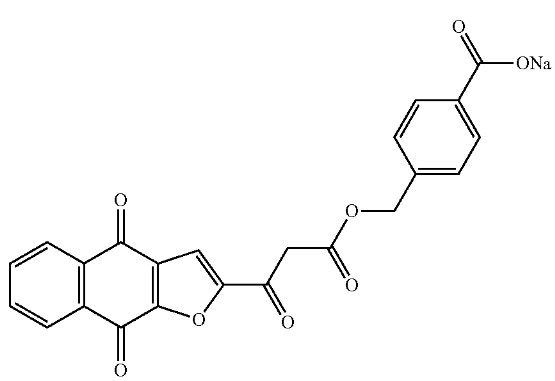 | $^1$H-NMR (DMSO-d$_6$, 400 MHz) δ: 4.10-4.63 (1H, br), 4.96-5.48 (2.5H, br), 7.03-7.28 (0.5H, br), 7.38-7.56 (2H, br), 7.75-8.03 (4H, br), 8.03-8.23 (2.9H, br). MS (ESI) m/z: 441 [M + Na] $^+$ |

TABLE 1-4-continued
| Ex. No. | structure | data |
|---|---|---|
| Ex. 38 | 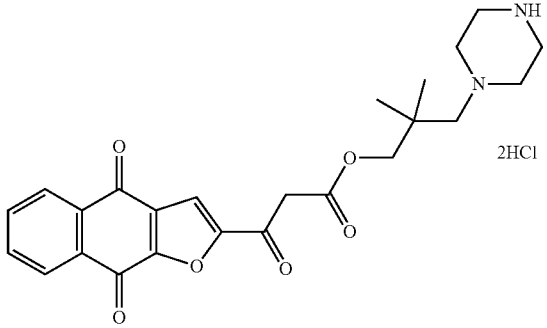 [SMILES: CC(C)(COC(=O)CC(=O)c1cc2c(o1)C(=O)c1ccccc1C2=O)CN1CCNCC1] 2HCl | $^1$H-NMR (D$_2$O, 400 MHz) δ: 1.19 (6H, s), 3.36 (2H, s), 3.65-3.77 (8H, m), 4.21 (2H, s), 7.82-7.84 (3H, m), 8.01-8.08 (2H, m). MS (ESI) m/z: 439 [M + H]$^+$ |
TABLE 1-5
| Ex. No. | structure | data |
|---|---|---|
| Ex. 39 | 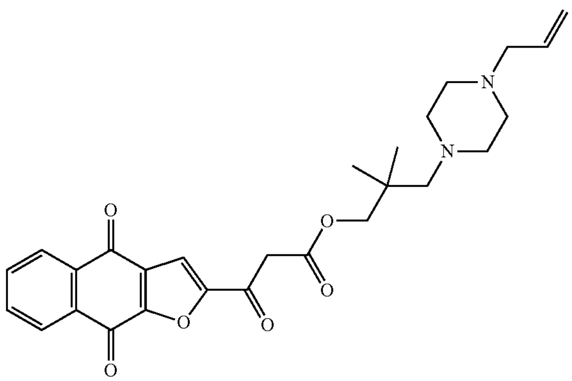 [SMILES: C=CCN1CCN(CC(C)(C)COC(=O)CC(=O)c2cc3c(o2)C(=O)c2ccccc2C3=O)CC1] | $^1$H-NMR (DMSO-d$_6$, 400 MHz) δ: 0.77 (4.8H, s), 0.94 (1.2H, s), 2.04 (1.6H, s), 2.23-2.42 (8H, m), 2.75-3.00 (2.4H, m), 3.80-3.94 (2H, m), 4.22 (1.6H, m), 5.03-5.20 (2H, m), 5.55 (0.2H, s), 5.64-5.78 (1H, m), 7.46 (0.2H, s), 7.88-7.98 (2H, m), 8.11-8.20 (2.8H, m). MS (ESI) m/z: 479 [M + H]$^+$ |
| Ex. 40 | 2HCl | $^1$H-NMR (D$_2$O, 400 MHz) δ: 2.17-2.28 (2H, m), 3.36-3.44 (2H, m), 3.56-3.74 (8H, m), 4.32-4.39 (2H, m), 7.81-7.89 (3H, m), 8.01-8.15 (2H, m). MS (ESI) m/z: 411 [M + H]$^+$ |
| Ex. 41 | HCl | $^1$H-NMR (DMSO-d$_6$, 400 MHz) δ: 1.09 (5.4H, s), 1.16 (0.6H, s), 3.08-3.27 (4H, m), 3.83-4.04 (4H, m), 4.09 (1.8H, s), 4.16 (0.2H, s), 4.31 (1.8H, s), 6.06 (0.1H, s), 7.68 (0.1H, s), 7.89-7.97 (2H, m), 8.11-8.19 (2H, m), 8.21 (0.9H, s), 9.69-9.94 (1H, br), 11.69-11.87 (0.1H, br). MS (ESI) m/z: 440 [M + H]$^+$ |

TABLE 1-5-continued
| Ex. No. | structure | data |
|---|---|---|
| Ex. 42 | 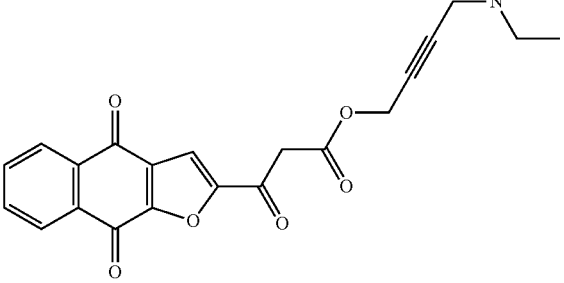 | $^1$H-NMR (DMSO-$d_6$, 400 MHz) δ: 0.89-1.00 (6H, m), 2.37-2.47 (4H, m), 3.40-3.50 (2H, m), 4.28 (1.8H, s), 4.81 (1.8H, s), 5.08 (0.2H, s), 5.78 (0.1H, s), 7.60 (0.1H, s), 7.85-7.98 (2H, m), 8.08-8.23 (2.9H, m). MS (ESI) m/z: 408 [M + H] $^+$ |
| Ex. 43 | 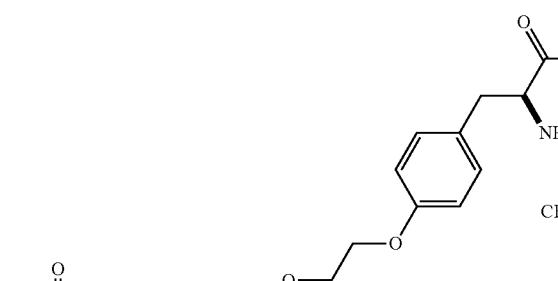 | $^1$H-NMR (DMSO-$d_6$, 400 MHz) δ: 2.80-2.98 (1.8H, m), 3.00-3.07 (0.2H, m), 4.04-4.17 (3H, m), 4.25 (1.8H, s), 4.39-4.48 (1.8H, m), 4.51-4.56 (0.2H, m), 6.05 (0.1H, s), 6.78-6.87 (1.8H, m), 6.93-6.98 (0.2H, m), 7.03-7.09 (1.8H, m), 7.15-7.20 (0.2H, m), 7.76 (0.1H, s), 7.87-7.95 (2H, m), 7.99-8.42 (6H, m), 12.99-14.66 (1H, br). MS (ESI) m/z: 492 [M + H] $^+$ |
| Ex. 44 | 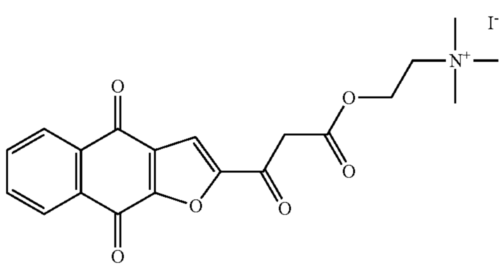 [SMILES: C[N+](C)(C)CCOC(=O)CC(=O)c1cc2c(o1)C(=O)c1ccccc1C2=O ; [I-]] | $^1$H-NMR (DMSO-$d_6$, 400 MHz) δ: 3.20 (9H, s), 3.30-3.37 (2H, m), 3.78-3.87 (2H, m), 4.74-4.85 (2H, m), 7.88-7.96 (3H, m), 8.10-8.20 (2H, m). |
TABLE 1-6
| Ex. No. | structure | data |
|---|---|---|
| Ex. 45 | 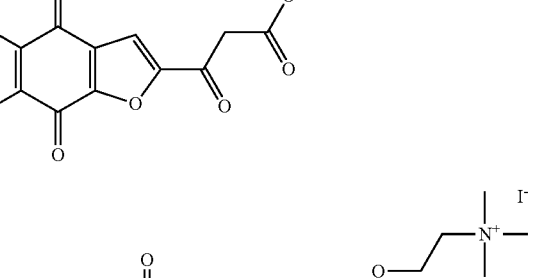 | $^1$H-NMR (DMSO-$d_6$, 400 MHz) δ: 2.08-2.10 (3H, m), 4.30 (1.7H, s), 5.73-5.81 (2H, m), 5.98 (0.15H, m), 7.89-7.95 (2H, m), 8.11-8.18 (3H, m). MS (ESI) m/z: 379 [M + Na] $^+$ |

TABLE 1-6-continued

| Ex. No. | structure | data |
|---|---|---|
| Ex. 46 | 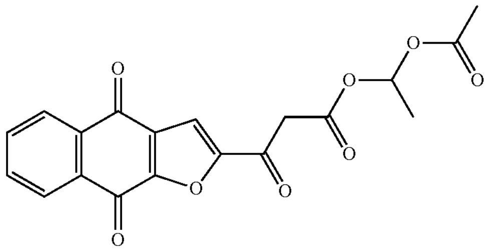 [SMILES: CC(=O)OC(C)OC(=O)CC(=O)c1cc2c(o1)C(=O)c1ccccc1C2=O] | ¹H-NMR (DMSO-d₆, 400 MHz) δ: 1.44 (2.7, d, J = 5.4 Hz), 1.50 (0.3H, d, J = 5.4 Hz), 2.04 (2.7H, s), 2.07 (0.3H, s), 4.20-4.32 (1.8H, m), 5.97 (0.1H, s), 6.79 (0.9H, q, J = 5.4 Hz), 6.87-6.93 (0.1H, m), 7.75 (0.1H, s), 7.87-7.95 (2H, m), 8.08-8.17 (2.9H, m), 11.58-11.83 (0.1H, br). MS (ESI) m/z: 393 [M + Na]⁺ |
| Ex. 47 | 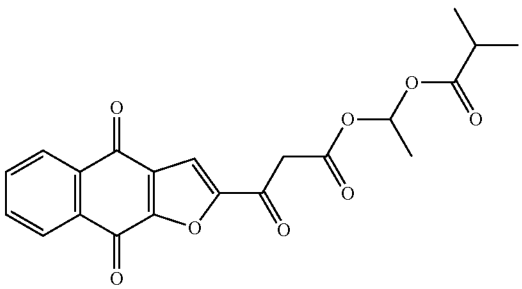 [SMILES: CC(OC(=O)CC(=O)c1cc2c(o1)C(=O)c1ccccc1C2=O)OC(=O)C(C)C] | ¹H-NMR (DMSO-d₆, 400 MHz) δ: 1.02-1.12 (6H, s), 1.44 (2.7H, d, J = 5.4 Hz), 1.50 (0.3H, d, J = 5.2 Hz), 2.52-2.64 (1H, m), 4.21-4.33 (1.8H, m), 5.98 (0.1H, s), 6.75-6.94 (1H, m), 7.77 (0.1H, s), 7.87-7.96 (2H, m), 8.08-8.18 (2.9H, m), 11.53-11.86 (0.1H, br). MS (ESI) m/z: 421 [M + Na]⁺ |
| Ex. 48 | 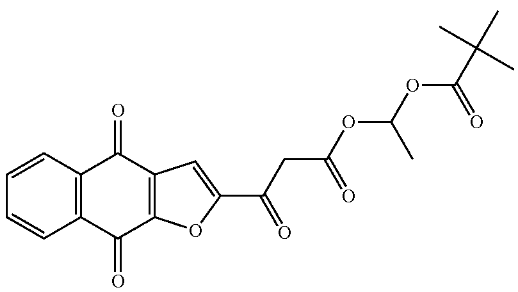 [SMILES: CC(OC(=O)CC(=O)c1cc2c(o1)C(=O)c1ccccc1C2=O)OC(=O)C(C)(C)C] | ¹H-NMR (DMSO-d₆, 400 MHz) δ: 1.09-1.18 (9H, m), 1.38-1.54 (3H, s), 4.27 (1.8H, m), 5.97 (0.1H, s), 6.76 (0.9H, q, J = 5.4 Hz), 6.88 (0.1H, q, J = 5.4 Hz), 7.76 (0.1H, s), 7.87-7.96 (2H, m), 8.08-8.20 (2.9H, m), 11.55-11.82 (0.1H, br). MS (ESI) m/z: 435 [M + Na]⁺ |
| Ex. 49 | 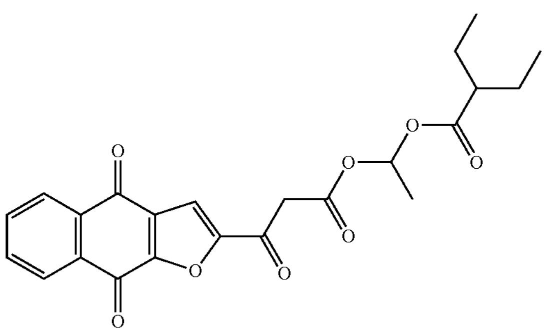 [SMILES: CCC(CC)C(=O)OC(C)OC(=O)CC(=O)c1cc2c(o1)C(=O)c1ccccc1C2=O] | ¹H-NMR (DMSO-d₆, 400 MHz) δ: 0.75-0.88 (6H, m), 1.41-1.55 (7H, m), 2.12-2.25 (1H, m), 4.20-4.31 (1.76H, m), 5.95 (0.12H, s), 6.83 (0.88H, q, J = 5.4 Hz), 6.95 (0.12H, q, J = 5.4 Hz), 7.76 (0.12H, s), 7.87-7.95 (2H, m), 8.09-8.17 (2.88H, m), 11.56-11.85 (0.12H, br). MS (ESI) m/z: 449 [M + Na]⁺ |
| Ex. 50 | 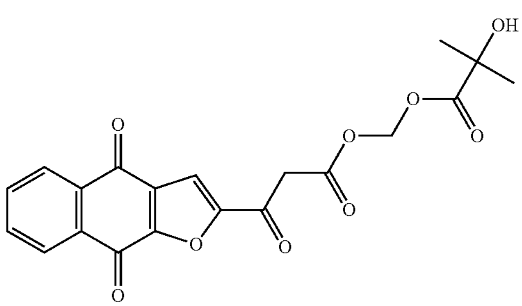 [SMILES: CC(C)(O)C(=O)OCOC(=O)CC(=O)c1cc2c(o1)C(=O)c1ccccc1C2=O] | ¹H-NMR (DMSO-d₆, 400 MHz) δ: 1.26-1.33 (6H, m), 4.33 (1.8H, s), 5.43-5.52 (1H, m), 5.78 (1.8H, s), 5.88 (0.2H, s), 5.99 (0.1H, s), 7.78 (0.1H, s), 7.75-7.85 (2H, m), 8.17-8.30 (2.9H, m), 11.60-11.75 (0.1H, br). MS (ESI) m/z: 423 [M + Na]⁺ |

TABLE 1-7

| Ex. No. | structure | data |
|---|---|---|
| Ex. 51 | 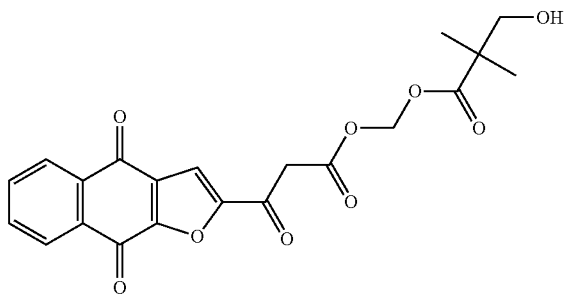 [SMILES: CC(C)(CO)C(=O)OCOC(=O)CC(=O)c1cc2c(o1)C(=O)c1ccccc1C2=O] | ¹H-NMR (DMSO-d₆, 400 MHz) δ: 1.06-1.09 (6H, m), 3.36-3.44 (2H, s), 4.30 (1.8H, s), 4.89 (1H, t, J = 5.4 Hz), 5.74 (1.8H, s), 5.83 (0.2H, s), 5.96 (0.1H, s), 7.88-7.96 (2H, m), 8.11-8.18 (3H, m). MS (ESI) m/z: 437 [M + Na]⁺ |
| Ex. 52 | 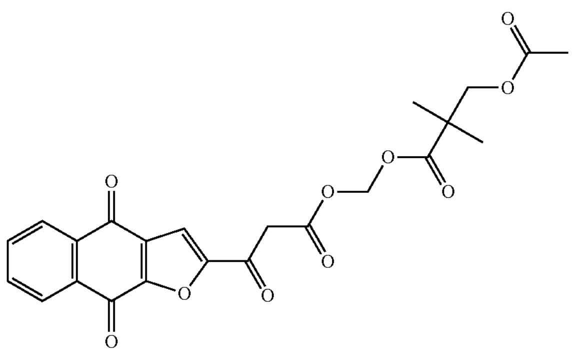 [SMILES: CC(=O)OCC(C)(C)C(=O)OCOC(=O)CC(=O)c1cc2c(o1)C(=O)c1ccccc1C2=O] | ¹H-NMR (DMSO-d₆, 400 MHz) δ: 1.11-1.21 (6H, m), 1.95-2.04 (3H, m), 3.98-4.07 (2H, m), 4.32 (1.7H, s), 5.77 (1.7H, s), 5.86 (0.3H, s), 6.00 (0.15H, s), 7.45 (0.15H, s), 7.75-7.84 (2H, m), 8.17-8.27 (2.85H, m), 11.58-11.78 (0.15H, br). MS (ESI) m/z: 479 [M + Na]⁺ |
| Ex. 53 | 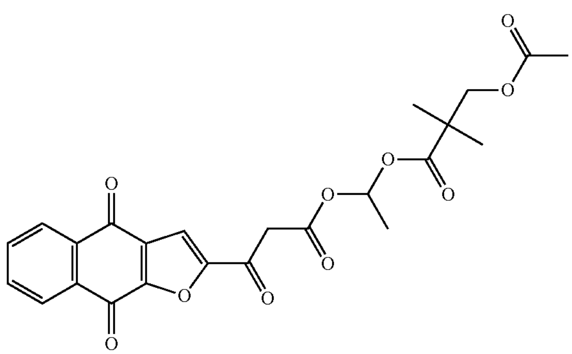 [SMILES: CC(=O)OCC(C)(C)C(=O)OC(C)OC(=O)CC(=O)c1cc2c(o1)C(=O)c1ccccc1C2=O] | ¹H-NMR (DMSO-d₆, 400 MHz) δ: 1.13 (5H, s), 1.17 (1H, m), 1.40-1.52 (3H, m), 1.97 (2.5H, s), 2.00 (0.5H, s), 3.95-4.08 (2H, m), 4.27 (1.8H, m), 5.95 (0.1H, s), 6.78 (0.8H, q, J = 5.4 Hz), 6.90 (0.2H, q, J = 5.4 Hz), 7.75 (0.1H, s), 7.88-7.97 (2H, m), 8.10-8.19 (2.9H, m), 11.60-11.75 (0.1H, s). MS (ESI) m/z: 493 [M + Na]⁺ |
| Ex. 54 | 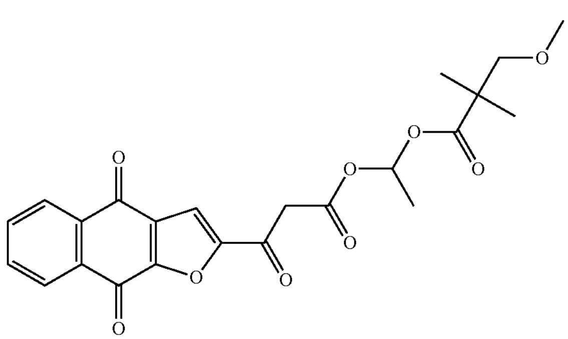 [SMILES: COCC(C)(C)C(=O)OC(C)OC(=O)CC(=O)c1cc2c(o1)C(=O)c1ccccc1C2=O] | ¹H-NMR (DMSO-d₆, 400 MHz) δ: 1.03-1.14 (6H, m), 1.37-1.52 (3H, m), 3.18-3.30 (5H, m), 4.28-4.32 (1.8H, m), 5.98 (0.1H, s), 6.72-6.81 (0.9H, m), 6.83-6.94 (0.1H, m), 7.78 (0.1H, s), 7.87-7.96 (2H, m), 8.09-8.18 (2.9H, m), 11.60-11.80 (0.1H, br). MS (ESI) m/z: 465 [M + Na]⁺ |

TABLE 1-7-continued
| Ex. No. | structure | data |
|---|---|---|
| Ex. 55 | 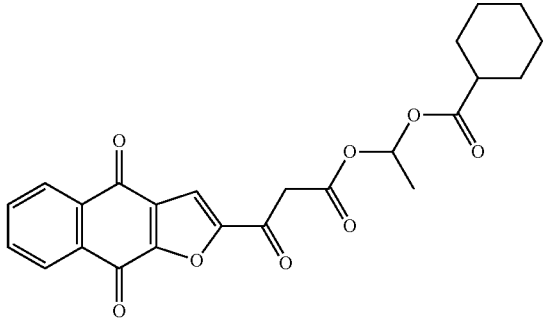 [SMILES: CC(OC(=O)CC(=O)c1cc2c(o1)C(=O)c1ccccc1C2=O)OC(=O)C1CCCCC1] | ¹H-NMR (DMSO-d₆, 400 MHz) δ: 1.08-1.85 (13H, m), 2.23-2.38 (1H, m), 4.18-4.29 (1.7H, m), 5.95 (0.15H, s), 6.73-6.94 (1H, m), 7.74 (0.15H, s), 7.85-7.95 (2H, m), 8.07-8.17 (2.85H, m), 11.49-11.82 (0.15H, br). MS (ESI) m/z: 461 [M + Na]⁺ |
| Ex. 56 | 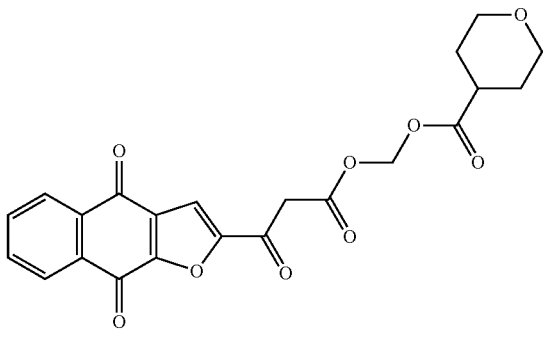 [SMILES: O=C(CC(=O)c1cc2c(o1)C(=O)c1ccccc1C2=O)OCOC(=O)C1CCOCC1] | ¹H-NMR (DMSO-d₆, 400 MHz) δ: 1.49-1.65 (2H, m), 1.70-1.83 (2H, m), 2.60-2.75 (1H, m), 3.28-3.41 (2H, m), 3.73-3.86 (2H, m), 4.32 (1.8H, s), 5.77 (1.8H, s), 5.86 (0.2H, s), 6.00 (0.1H, s), 7.78 (0.1H, s), 7.88-8.02 (2H, m), 8.09-8.22 (2.9H, m), 11.59-11.75 (0.1H, br). MS (ESI) m/z: 449 [M + Na]⁺ |
TABLE 1-8
| Ex. No. | structure | data |
|---|---|---|
| Ex. 57 | 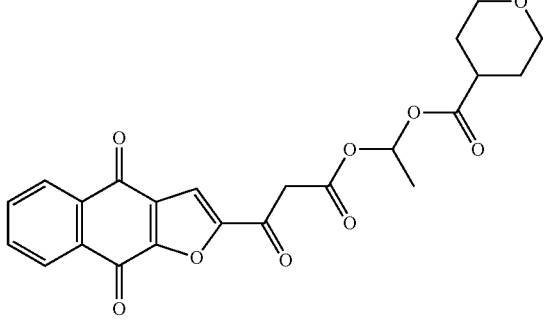 | ¹H-NMR (DMSO-d₆, 400 MHz) δ: 1.40-1.60 (5H, m), 1.66-1.78 (2H, m), 2.55-2.70 (1H, m), 3.25-3.37 (2H, m), 3.70-3.85 (2H, m), 4.27 (1.8H, s), 5.97 (0.1H, s), 6.80 (0.9H, q, J = 5.4 Hz), 6.91 (0.1H, q, J = 5.4 Hz), 7.77 (0.1H, s), 7.87-7.96 (2H, m), 8.08-8.20 (2.9H, m), 11.60-11.75 (0.1H, br). MS (ESI) m/z: 463 [M + Na]⁺ |
| Ex. 58 | 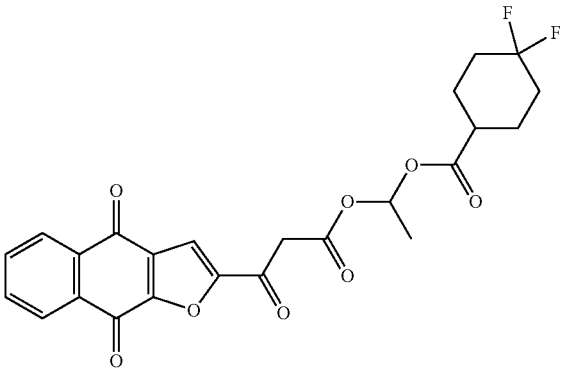 [SMILES: CC(OC(=O)CC(=O)c1cc2c(o1)C(=O)c1ccccc1C2=O)OC(=O)C1CCC(F)(F)CC1] | ¹H-NMR (DMSO-d₆, 400 MHz) δ: 1.40-1.67 (5H, m), 1.40-1.67 (6H, m), 2.53-2.64 (1H, m), 4.27 (1.8H, s), 5.95 (0.1H, s), 6.80 (0.9H, d, J = 5.4 Hz), 6.91 (0.1H, d, J = 5.4 Hz), 7.75 (0.1H, s), 7.88-7.96 (2H, m), 8.08-8.20 (2.9H, m), 12.24-12.32 (0.1H, br). MS (ESI) m/z: 497 [M + Na]⁺ |

TABLE 1-8-continued
| Ex. No. | structure | data |
|---|---|---|
| Ex. 59 | 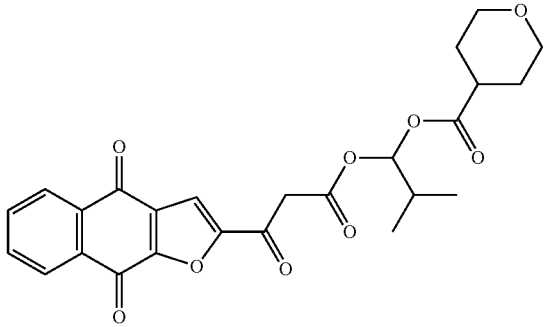 [SMILES: CC(C)C(OC(=O)CC(=O)c1cc2c(o1)C(=O)c1ccccc1C2=O)OC(=O)C1CCOCC1] | $^1$H-NMR (DMSO-d$_6$, 400 MHz) δ: 0.85-1.00 (6H, m), 1.43-1.60 (2H, m), 1.63-1.80 (2H, m), 1.92-2.04 (1H, m), 2.57-2.69 (1H, m), 3.25-3.40 (2H, m), 3.68-3.82 (2H, m), 4.22-4.35 (1.8H, m), 5.96 (0.1H, s), 6.57 (0.9H, d, J = 5.1 Hz), 6.69 (0.1H, d, J = 5.1 Hz), 7.73 (0.1H, s), 7.85-7.96 (2H, m), 8.08-8.20 (2.9H, m), 11.50-11.80 (0.1H, br). MS (ESI) m/z: 491 [M + Na]$^+$ |
| Ex. 60 | 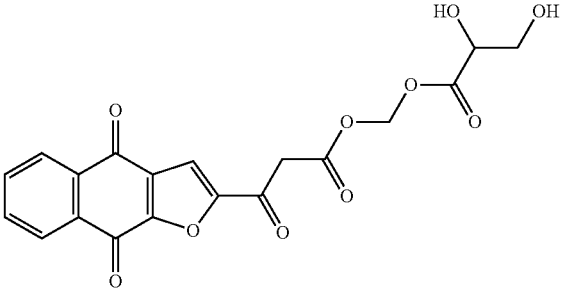 [SMILES: O=C(CC(=O)c1cc2c(o1)C(=O)c1ccccc1C2=O)OCOC(=O)C(O)CO] | $^1$H-NMR (DMSO-d$_6$, 400 MHz) δ: 3.50-3.62 (2H, m), 4.07-4.17 (1H, m), 4.31 (1.7H, s), 4.84-4.95 (1H, br), 5.57 (1H, d, J = 6.1 Hz), 5.74-5.82 (1.7H, m), 5.84-5.92 (0.3H, m), 5.99 (0.15H, s), 7.78 (0.15H, s), 7.87-7.97 (2H, m), 8.08-8.20 (2.85H, m), 11.60-11.75 (0.15H, br). MS (ESI) m/z: 425 [M + Na]$^+$ |
| Ex. 61 | 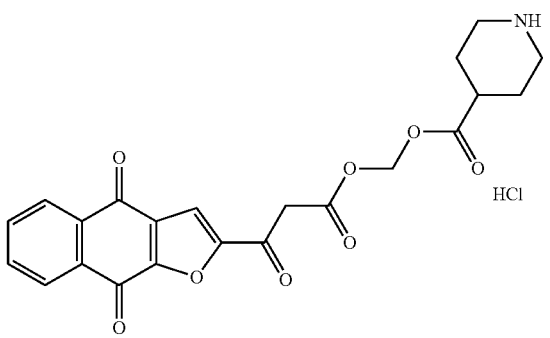 [SMILES: O=C(CC(=O)c1cc2c(o1)C(=O)c1ccccc1C2=O)OCOC(=O)C1CCNCC1 ; Cl] | $^1$H-NMR (DMSO-d$_6$, 400 MHz) δ: 1.65-1.80 (2H, m), 1.92-2.03 (2H, m), 2.70-2.82 (1H, m), 2.87-3.02 (2H, m), 3.08-3.26 (2H, m), 4.34 (1.8H, s), 5.78 (1.8H, s), 5.87 (0.2H, s), 5.99 (0.1H, m), 7.79 (0.1H, s), 7.88-7.98 (2H, m), 8.09-8.20 (2.9H, m), 8.53-8.70 (1H, br), 8.80-8.95 (1H, br), 11.47-11.89 (0.1H, br). MS (ESI) m/z: 426 [M + H]$^+$ |
| Ex. 62 | 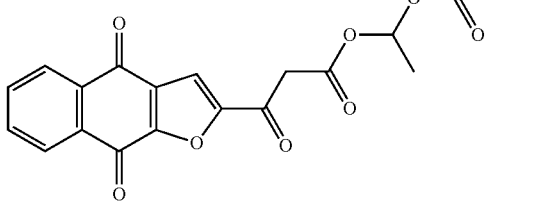 | $^1$H-NMR (DMSO-d$_6$, 400 MHz) δ: 1.17-1.24 (3H, m), 1.46-1.54 (3H, m), 4.10-4.22 (2H, m), 4.25-4.34 (1.8H, m), 5.88-5.94 (0.1H, br), 6.65-6.81 (1H, m), 7.69-7.74 (0.1H, br), 7.88-7.97 (2H, m), 8.09-8.18 (2.9H, m). MS (ESI) m/z: 423 [M + Na]$^+$ |

TABLE 1-9

| Ex. No. | structure | data |
|---|---|---|
| Ex. 63 | 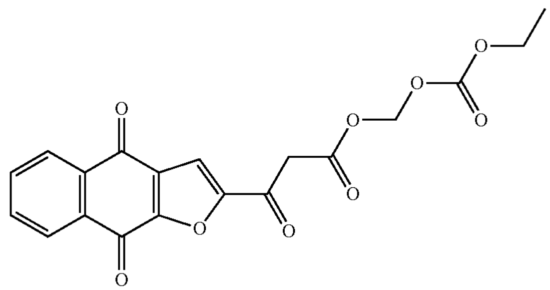 [SMILES: CCOC(=O)OCOC(=O)CC(=O)c1cc2c(o1)C(=O)c1ccccc1C2=O] | ¹H-NMR (DMSO-d₆, 400 MHz) δ: 1.19-1.26 (3H, m), 4.13-4.23 (2H, m), 4.34 (1.8H, s), 5.73 (1.8H, s), 5.84 (0.2H, s), 6.01 (0.1H, s), 7.78 (0.1H, s), 7.87-7.97 (2H, m), 8.08-8.19 (2.9H, m), 11.53-11.77 (0.1H, br). MS (ESI) m/z: 409 [M + Na] ⁺ |
| Ex. 64 | 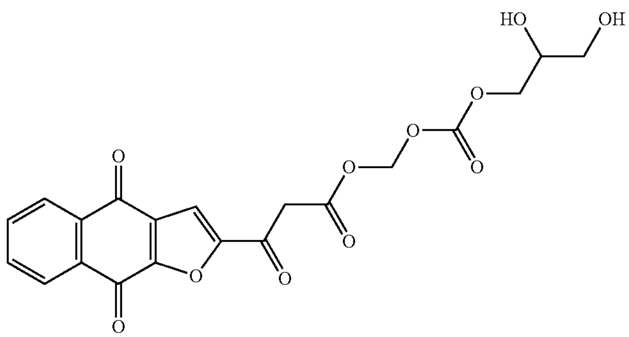 [SMILES: O=C(CC(=O)c1cc2c(o1)C(=O)c1ccccc1C2=O)OCOC(=O)OCC(O)CO] | ¹H-NMR (DMSO-d₆, 400 MHz) δ: 3.27-3.40 (2H, m), 3.62-3.72 (1H, m), 3.98-4.07 (1H, m), 4.14-4.23 (1H, m), 4.19-4.27 (1.6H, m), 4.84-4.94 (1H, br), 5.52-5.62 (1H, br), 5.76 (1.6H, s), 5.85 (0.4H, s), 6.00 (0.2H, s), 7.78 (0.2H, s), 7.87-7.97 (2H, m), 8.09-8.20 (2.8H, m), 11.50-11.82 (0.2H, br). MS (ESI) m/z: 455 [M + Na] ⁺ |
| Ex. 65 | 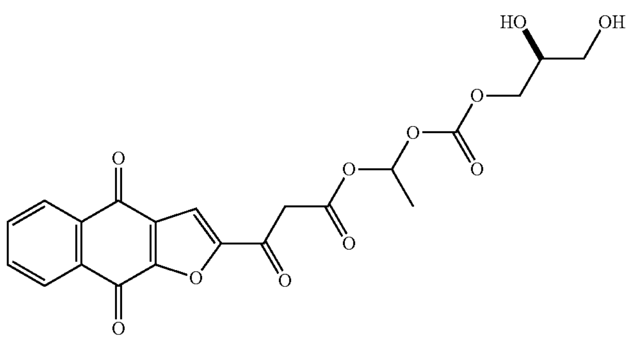 [SMILES: CC(OC(=O)CC(=O)c1cc2c(o1)C(=O)c1ccccc1C2=O)OC(=O)OC[C@@H](O)CO] | ¹H-NMR (DMSO-d₆, 400 MHz) δ: 1.42-1.56 (3H, m), 3.20-3.40 (2H, s), 3.59-3.71 (1H, m), 3.92- 4.07 (1H, m), 4.09-4.20 (1H, m), 4.24-4.36 (1.8H, m), 4.61-4.75 (1H, br), 4.95-5.05 (1H, br), 5.98 (0.1H, m), 6.65-6.85 (1H, m), 7.76 (0.1H, s), 7.87-7.97 (2H, m), 8.09-8.19 (2.9H, m), 11.20-11.66 (0.1H, br). MS (ESI) m/z: 469 [M + Na] ⁺ |
| Ex. 66 | 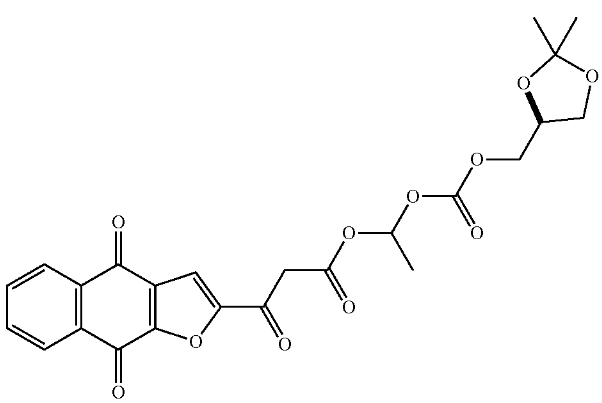 | ¹H-NMR (DMSO-d₆, 400 MHz) δ: 1.22-1.33 (6H, m), 1.48 (2.55H, d, J = 5.4 Hz), 1.54 (0.45H, d, J = 5.1 Hz), 3.61-3.71 (1H, m), 3.97-4.13 (2H, m), 4.16-4.35 (3.7H, m), 5.97-6.01 (0.15H, m), 6.70 (0.85H, q, J = 5.4 Hz), 6.78-6.85 (0.15H, m), 7.77 (0.15H, s), 7.88-7.96 (2H, m), 8.09-8.18 (2.85H, m), 11.52-11.83 (0.15H, br). MS (ESI) m/z: 509 [M + Na] ⁺ |

TABLE 1-9-continued

| Ex. No. | structure | data |
|---|---|---|
| Ex. 67 | 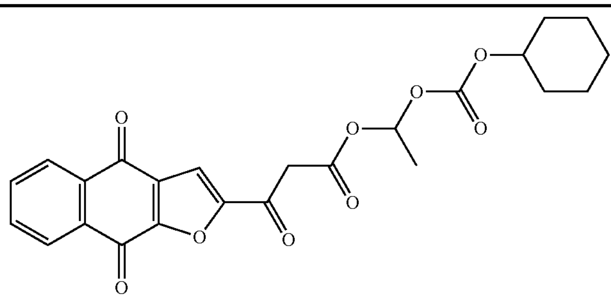 | ¹H-NMR (DMSO-d₆, 400 MHz) δ: 1.12-1.40 (6H, m), 1.46 (2.7H, d, J = 5.1 Hz), 1.53 (0.3H, d, J = 5.4 Hz), 1.56-1.67 (2H, m), 1.75-1.90 (2H, m), 4.21-4.33 (1.8H, m), 4.46-4.62 (1H, m), 5.99 (0.1H, m), 6.82 (0.9H, q, J = 5.1 Hz), 6.75-6.83 (0.1H, m), 7.77 (0.1H, s), 7.88-7.96 (2H, m), 8.07-8.17 (2.9H, m), 11.60-11.75 (0.1H, br). MS (ESI) m/z: 477 [M + Na]⁺ |

TABLE 1-10

| Ex. No. | structure | data |
|---|---|---|
| Ex. 68 | 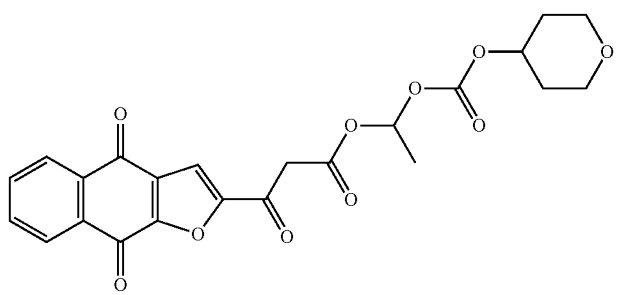 [SMILES: CC(OC(=O)CC(=O)c1cc2c(o1)C(=O)c1ccccc1C2=O)OC(=O)OC1CCOCC1] | ¹H-NMR (DMSO-d₆, 400 MHz) δ: 1.43-1.62 (5H, m), 1.81-1.95 (2H, m), 3.35-3.48 (2H, m), 3.68-3.80 (2H, m), 4.25 (0.9H, d, J = 16.6 Hz), 4.30 (0.9H, d, J = 16.6 Hz), 4.64-4.84 (1H, m), 5.99 (0.1H, s), 6.69 (0.9H, q, J = 5.4 Hz), 6.80 (0.1H, q, J = 5.4 Hz), 7.77 (0.1H, s), 7.85-7.97 (2H, m), 8.07-8.20 (2.9H, m), 11.60-11.75 (0.1H, br). MS (ESI) m/z: 479 [M + Na]⁺ |
| Ex. 69 | 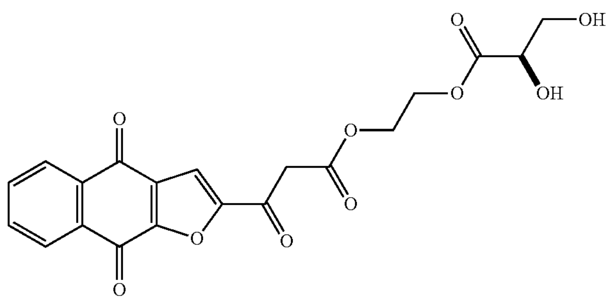 [SMILES: O=C(CC(=O)c1cc2c(o1)C(=O)c1ccccc1C2=O)OCCOC(=O)[C@H](O)CO] | ¹H-NMR (DMSO-d₆, 400 MHz) δ: 3.48-3.63 (2H, m), 4.00-4.12 (1H, m), 4.20-4.45 (5.8H, m), 4.60-5.00 (1H, br), 5.10-5.60 (1H, br), 6.00 (0.1H, s), 7.74 (0.1H, s), 7.75-7.84 (2H, m), 8.17-8.26 (2.9H, m), 11.74-11.86 (0.1H, br). MS (ESI) m/z: 439 [M + Na]⁺ |
| Ex. 70 | 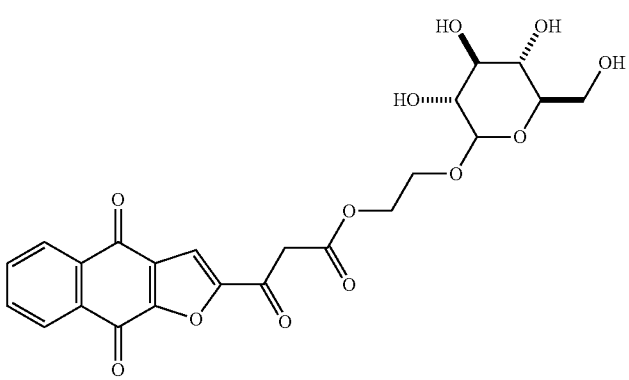 [SMILES: O=C(CC(=O)c1cc2c(o1)C(=O)c1ccccc1C2=O)OCCOC1O[C@H](CO)[C@@H](O)[C@H](O)[C@H]1O] | ¹H-NMR (acetone-d₆ + D₂O, 400 MHz) δ: 3.25-3.46 (3H, m), 3.53-4.20 (6H, m), 4.28-4.79 (2.5H, m), 4.81-4.85 (0.5H, m), 5.95-6.01 (0.5H, s), 7.49-7.53 (0.5H, m), 7.86-7.96 (2.5H, m), 8.13-8.24 (2H, m). MS (ESI) m/z: 513 [M + Na]⁺ |

TABLE 1-10-continued
| Ex. No. | structure | data |
|---|---|---|
| Ex. 71 | 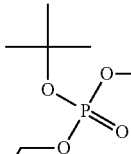 | $^1$H-NMR (DMSO-$d_6$, 400 MHz) δ: 1.37 (18H, s), 3.97-4.06 (1.8H, m), 4.08-4.15 (0.2H, m), 4.22 (1.9H, s), 4.25-4.30 (1.8H, m), 4.34-4.41 (0.2H, m), 5.95 (0.1H, s), 7.86-7.95 (2H, m), 8.08-8.18 (3H, m). MS (ESI) m/z: 543 [M + Na]$^+$ |
| Ex. 72 | 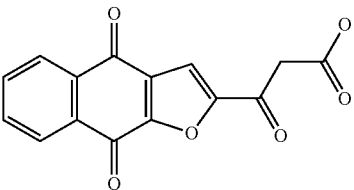 | $^1$H-NMR (DMSO-$d_6$, 400 MHz) δ: 1.33-1.64 (4H, m), 1.75-1.87 (2H, m), 2.72-2.82 (2H, m), 3.96-4.05 (1H, m), 4.27 (1.8H, s), 4.33-4.43 (4H, m), 5.86 (0.1H, s), 7.67 (0.1H, s), 7.80-8.75 (10.9H, m), 11.77-11.83 (0.1H, br). MS (ESI) mz: 457 [M + H]$^+$ |
| Ex. 73 | 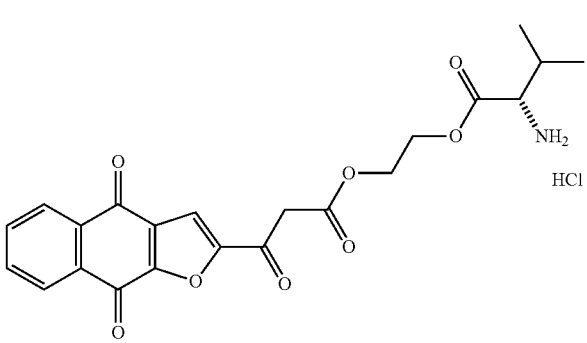 [SMILES: CC(C)[C@H](N)C(=O)OCCOC(=O)CC(=O)c1cc2c(o1)C(=O)c1ccccc1C2=O ; Cl] | $^1$H-NMR (DMSO-$d_6$, 400 MHz) δ: 0.92-1.03 (6H, m), 2.08-2.22 (1H, m), 3.92 (0.9H, m), 3.97 (0.1H, m), 4.23 (1.8H, s), 4.31-4.60 (4H, m), 5.93 (0.1H, s), 7.74 (0.1H, s), 7.88-7.96 (2H, m), 8.10-8.19 (2.9H, m), 8.24-8.60 (3H, br), 11.83-12.02 (0.1H, br). MS (ESI) mz: 428 [M + H]$^+$ |
TABLE 1-11
| Ex. No. | structure | data |
|---|---|---|
| Ex. 74 | 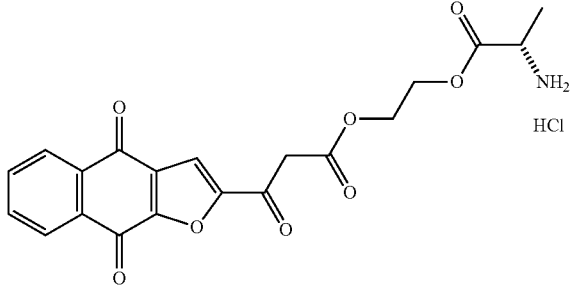 [SMILES: C[C@H](N)C(=O)OCCOC(=O)CC(=O)c1cc2c(o1)C(=O)c1ccccc1C2=O ; Cl] | $^1$H-NMR (DMSO-$d_6$, 400 MHz) δ: 1.38-1.46 (3H, m), 4.02-4.15 (1H, m), 4.27 (1.8H, s), 4.31-4.50 (4H, m), 5.98 (0.1H, s), 7.74 (0.1H, s), 7.88-7.96 (2H, m), 8.09-8.19 (2.9H, m), 8.42-8.73 (3H, br). MS (ESI) m/z: 400 [M + H]$^+$ |

TABLE 1-11-continued

| Ex. No. | structure | data |
|---|---|---|
| Ex. 75 | 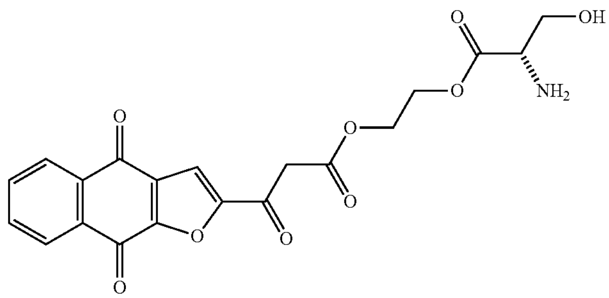 | ¹H-NMR (DMSO-d₆, 400 MHz) δ: 3.75-3.88 (2H, m), 4.10-4.21 (1H, m), 4.25 (1.8H, s), 4.30-4.50 (4H, m), 5.53-5.62 (1H, br), 5.98 (0.1H, s), 7.74 (0.1H, s), 7.75-7.84 (2H, m), 8.17-8.27 (2.9H, m), 8.30-8.60 (3H, br). MS (ESI) m/z: 416 [M + H]⁺ |
| Ex. 76 | 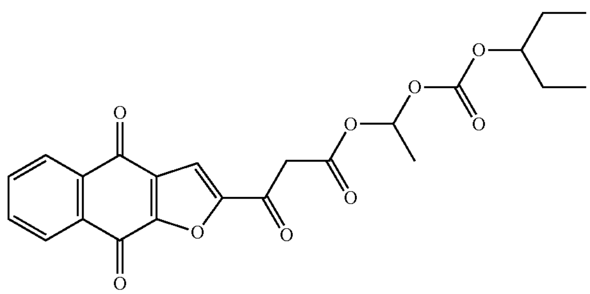 [SMILES: CCC(CC)OC(=O)OC(C)OC(=O)CC(=O)c1cc2c(o1)C(=O)c1ccccc1C2=O] | ¹H-NMR (DMSO-d₆, 400 MHz) δ: 0.77-0.88 (6H, m), 1.44-1.63 (7H, m), 4.22-4.34 (1.8H, m), 4.44-4.57 (1H, m), 5.99 (0.1H, s), 6.69 (0.9H, q, J = 5.4 Hz), 6.76-6.82 (0.1H, m), 7.77 (0.1H, s), 7.88-7.95 (2H, m), 8.09-8.18 (2.9H, m), 11.59-11.87 (0.1H, br). MS (ESI) m/z: 465 [M + Na]⁺ |
| Ex. 77 | 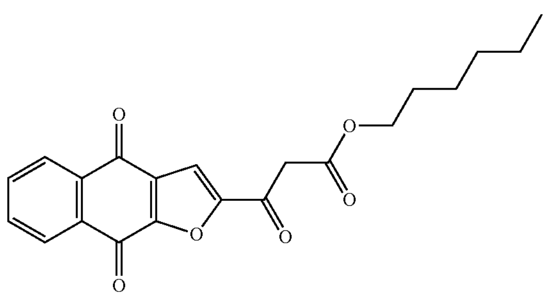 [SMILES: CCCCCCOC(=O)CC(=O)c1cc2c(o1)C(=O)c1ccccc1C2=O] | ¹H-NMR (DMSO-d₆, 400 MHz) δ: 0.77-0.92 (3H, m), 1.16-1.41 (6H, m), 1.49-1.71 (2H, m), 4.09 (2H, t, J = 6.4 Hz), 4.21 (1.8H, m), 6.01 (0.1H, s), 7.74 (0.1H, s), 7.88-7.97 (2H, m), 8.09-8.18 (2.9H, m), 11.93-12.02 (0.1H, br). MS (ESI) m/z: 391 [M + Na]⁺ |
| Ex. 78 | 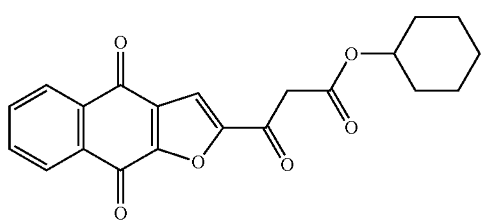 [SMILES: O=C(CC(=O)c1cc2c(o1)C(=O)c1ccccc1C2=O)OC1CCCCC1] | ¹H-NMR (DMSO-d₆, 400 MHz) δ: 1.15-1.49 (6H, m), 1.56-1.93 (4H, m), 4.18 (1.8H, m), 4.70-4.90 (1H, m), 6.00 (0.1H, s), 7.74 (0.1H, s), 7.87-7.96 (2H, m), 8.09-8.18 (2.9H, m), 12.04-12.10 (0.1H, br). MS (ESI) m/z: 389 [M + Na]⁺ |
| Ex. 79 | 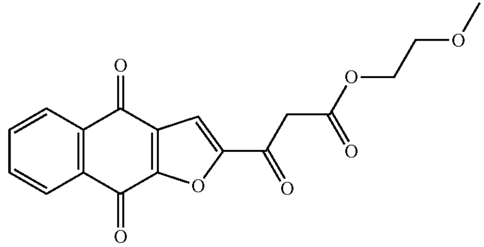 [SMILES: COCCOC(=O)CC(=O)c1cc2c(o1)C(=O)c1ccccc1C2=O] | ¹H-NMR (DMSO-d₆, 400 MHz) δ: 3.24 (2.7H, s), 3.29 (0.3H, s), 3.50-3.55 (1.8H, m), 3.58-3.63 (0.2H, m), 4.20-4.25 (3.6H, m), 4.30-4.35 (0.2H, m), 6.04 (0.1H, s), 7.76 (0.1H, s), 7.88-7.95 (2H, m), 8.09-8.17 (2.9H, m), 11.84-11.98 (0.1H, br). MS (ESI) m/z: 365 [M + Na]⁺ |

TABLE 1-12

| Ex. No. | structure | data |
|---|---|---|
| Ex. 80 | 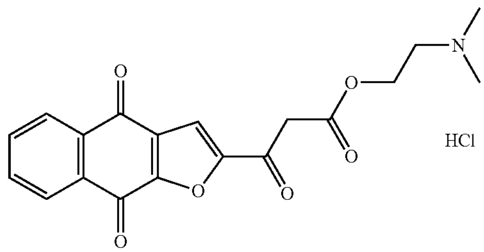 [SMILES: CN(C)CCOC(=O)CC(=O)c1cc2c(o1)C(=O)c1ccccc1C2=O ; Cl] | $^{1}$H-NMR (DMSO-d$_6$, 400 MHz) δ: 2.86 (6H, s), 3.30-3.37 (2H, m), 3.48-3.58 (2H, m), 4.64-4.73 (2H, m), 7.89-7.97 (2H, m), 8.10-8.20 (3H, m), 10.39-10.56 (1H, br). MS (ESI) m/z: 355 [M + H]$^+$ |
| Ex. 81 | 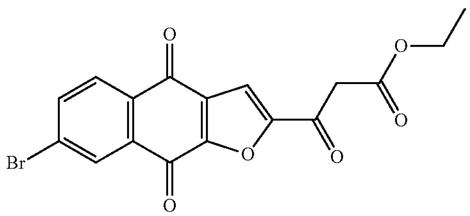 [SMILES: CCOC(=O)CC(=O)c1cc2c(o1)C(=O)c1cc(Br)ccc1C2=O] | $^{1}$H-NMR (DMSO-d$_6$, 400 MHz) δ: 1.20 (2.7H, t, J = 7.1 Hz), 1.28 (0.3H, t, J = 7.1 Hz), 4.14 (1.7H, q, J = 7.1 Hz), 4.20 (1.8H, s), 4.25 (0.2H, q, J = 7.1 Hz), 6.01 (0.1H, s), 7.77 (0.1H, s), 7.99-8.07 (1H, m), 8.08-8.23 (2.9H, m). MS (ESI) m/z: 393 [M + H]$^+$ |
| Ex. 82 | 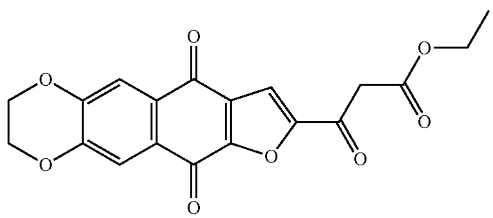 | $^{1}$H-NMR (DMSO-d$_6$, 400 MHz) δ: 1.20 (2.7H, t, J = 7.1 Hz), 1.27 (0.3H, t, J = 7.1 Hz), 4.10-4.28 (3.8H, m), 4.42 (4H, s), 5.97 (0.1H, s), 7.46-7.55 (2H, m), 7.68 (0.1H, s), 8.10 (0.9H, s). MS (ESI) m/z: 493 [M + Na]$^+$ |
| Ex. 83 | 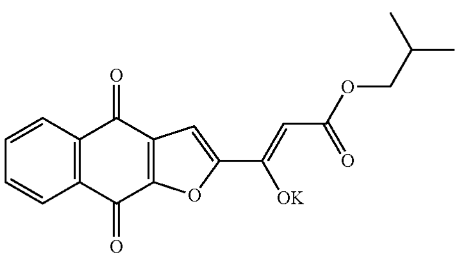 | $^{1}$H-NMR (DMSO-d$_6$, 400 MHz) δ: 0.82-0.96 (6H, m), 1.73-1.90 (1H, m), 3.62 (2H, d, J = 6.6 Hz), 5.01 (1H, s), 6.99 (1H, s), 7.80-7.93 (2H, m), 8.03-8.17 (2H, s). MS (ESI) m/z: 363 [M + Na]$^+$ |
| Ex. 84 | 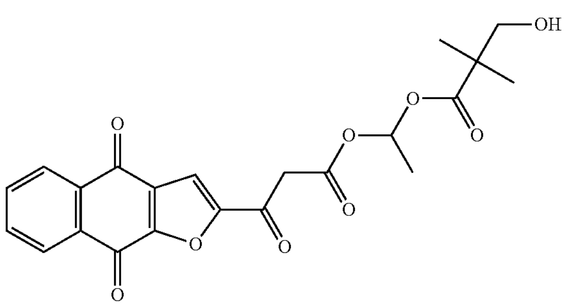 | $^{1}$H-NMR (DMSO-d$_6$, 400 MHz) δ: 1.03 (2.7H, s), 1.04 (0.3H, s), 1.08 (0.3H, s), 1.43 (2.7H, d, J = 5.4 Hz), 1.49 (0.3H, d, J = 5.4 Hz), 3.29-3.44 (2H, m), 4.21-4.31 (1.8H, m), 4.84 (1H, t, J = 5.4 Hz), 5.94 (0.1H, s), 6.76 (0.9H, q, J = 5.4 Hz), 6.96 (0.1H, q, J = 5.4 Hz), 7.74 (0.1H, s), 7.87-7.97 (2H, m), 8.10-8.18 (2.9H, m), 11.65-11.80 (0.1H, br). MS (ESI) m/z: 451 [M + Na]$^+$ |
| Ex. 85 | 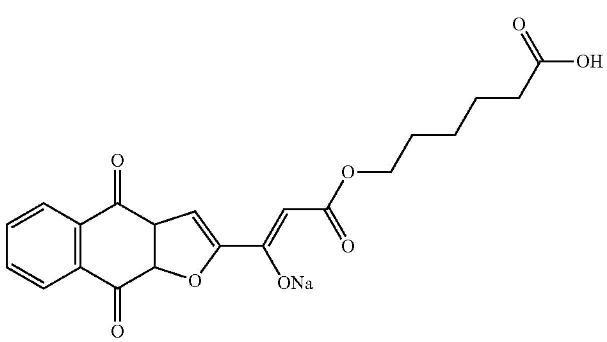 | $^{1}$H-NMR (DMSO-d$_6$, 400 MHz) δ: 1.27-1.39 (2H, m), 1.45-1.60 (4H, m), 2.20 (2H, t, J = 7.3 Hz), 3.80-3.93 (2H, br), 5.10 (1H, s), 7.06 (1H, s), 7.82-7.90 (2H, m), 8.03-8.13 (2H, m), 9.50-14.63 (1H, m). MS (ESI) m/z: 419 [M − H]$^−$ |

TABLE 1-12-continued

| Ex. No. | structure | data |
|---|---|---|
| Ex. 86 | (structure) | ¹H-NMR (DMSO-d₆, 400 MHz) δ: 3.23-3.48 (2H, m), 3.55-3.67 (1H, m), 3.72-3.93 (2H, m), 4.68-5.05 (3H, m), 6.96-7.04 (1H, br), 7.78-7.93 (2H, m), 8.00-8.16 (2H, m). MS (ESI) m/z: 381 [M + Na]⁺ |

TABLE 1-13

| Ex. No. | structure | data |
|---|---|---|
| Ex. 87 | (structure) | ¹H-NMR (DMSO-d₆, 400 MHz) δ: 1.16 (3H, t, J = 7.0 Hz), 3.93 (2H, q, J = 7.0 H), 5.11 (1H, s), 7.06 (1H, s), 7.80-7.91 (2H, m), 8.03-8.12 (2H, m). MS (ESI) m/z: 335 [M + Na]⁺ |
| Ex. 88 | (structure) | ¹H-NMR (DMSO-d₆, 400 MHz) δ: 3.35-3.41 (2H, m), 3.57-3.66 (1H, m), 3.81-3.90 (2H, m), 4.66-4.86 (2H, br), 5.11 (1H, s), 7.06 (1H, s), 7.76-7.95 (2H, m), 8.02-8.16 (2H, m). MS (ESI) m/z: 381 [M + Na]⁺ |
| Ex. 89 | (structure) | ¹H-NMR (DMSO-d₆, 400 MHz) δ: 3.27 (3H, s), 3.47-3.53 (2H, m), 3.98-4.06 (2H, m), 5.12 (1H, s), 7.08 (1H, s), 7.88-7.95 (2H, m), 8.01-8.17 (2H, m). MS (ESI) m/z: 365 [M + Na]⁺ |
| Ex. 90 | (structure) | ¹H-NMR (DMSO-d₆, 400 MHz) δ: 4.22-4.63 (5.8H, m), 4.99-5.15 (1H, m), 6.02 (0.1H, s), 7.78 (0.1H, s), 7.88-7.96 (2H, m), 8.09-8.20 (2.9H, m), 11.66-11.78 (0.1H, br). MS (ESI) m/z: 407 [M + Na]⁺ |

TABLE 1-13-continued

| Ex. No. | structure | data |
|---|---|---|
| Ex. 91 | 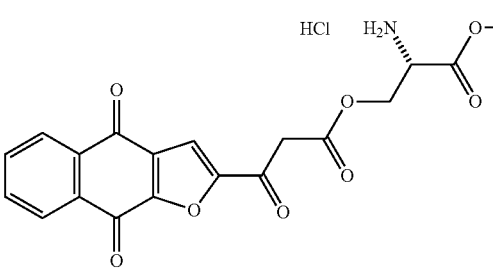 | $^1$H-NMR (DMSO-d$_6$, 400 MHz) δ: 1.21-1.27 (3H, m), 4.17-4.28 (3.8H, m), 4.48-4.61 (3H, m), 5.91 (0.1H, s), 7.69 (0.1H, s), 7.90-7.96 (2H, m), 8.11-8.20 (2.9H, m), 8.55-9.10 (3H, br). MS (ESI) m/z: 400 [M + H]$^+$ |
| Ex. 92 | 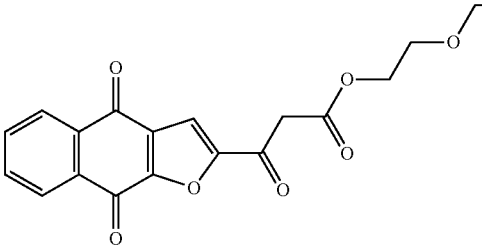 | $^1$H-NMR (DMSO-d$_6$, 400 MHz) δ: 1.07 (2.7H, t, J = 7.1 Hz), 1.12 (0.3H, t, J = 7.1 Hz), 3.42 (1.8H, q, J = 7.1 Hz), 3.49 (0.2H, q, J = 7.1 Hz), 3.52-3.58 (1.8H, m), 3.60-3.65 (0.2H, m), 4.17-4.25 (3.6H, m), 4.29-4.34 (0.2H, m), 6.04 (0.1H, s), 7.76 (0.1H, s), 7.87-7.95 (2H, m), 8.10-8.18 (2.9H, m), 11.85-11.95 (0.1H, br). MS (ESI) m/z: 379 [M + Na]$^+$ |

TABLE 1-14

| Ex. No. | structure | data |
|---|---|---|
| Ex. 93 | 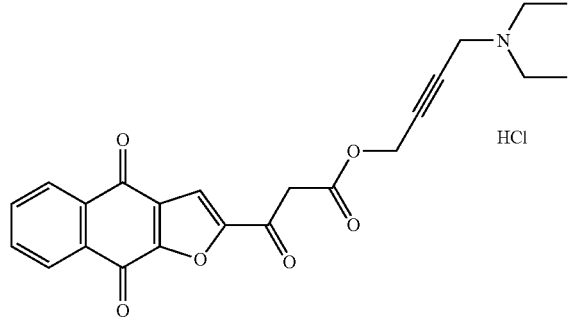 [SMILES: CCN(CC)CC#CCOC(=O)CC(=O)c1cc2c(o1)C(=O)c1ccccc1C2=O ; Cl] | $^1$H-NMR (DMSO-d$_6$, 400 MHz) δ: 1.24 (6H, t, J = 7.12 Hz), 3.02-3.25 (4H, m), 4.14-4.22 (2H, m), 4.32 (1.8H, s), 4.92 (1.8H, s), 5.01 (0.2H, s), 6.02 (0.1H, s), 7.79 (0.1H, s), 7.89-7.98 (2H, m), 8.10-8.22 (2.9H, m), 10.70-11.30 (1H, br). MS (ESI) m/z: 408 [M + H]$^+$ |
| Ex. 94 | 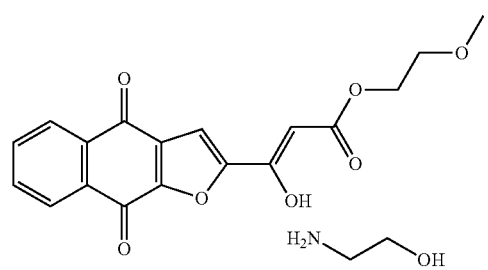 | $^1$H-NMR (DMSO-d$_6$, 400 MHz) δ: 2.80-2.85 (2H, m), 3.27 (3H, s), 3.46-3.58 (4H, m), 3.95-4.03 (1.6H, m), 4.17-4.28 (0.4H, m), 5.00-5.15 (2H, m), 7.00-7.40 (3H, m), 7.82-7.97 (2H, m), 8.05-8.18 (2H, m). MS (ESI) m/z: 365 [M + Na]$^+$ |

TABLE 1-14-continued
| Ex. No. | structure | data |
|---|---|---|
| Ex. 95 | 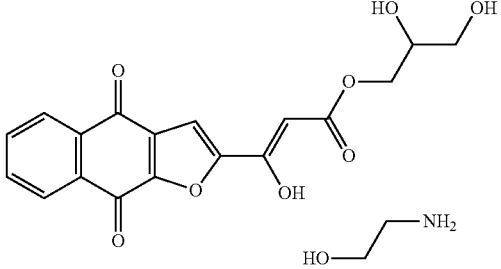 | ¹H-NMR (D₂O, 400 MHz) δ: 2.94-3.02 (2H, m), 3.49-3.63 (2H, m), 3.63-3.71 (2H, m), 3.85-4.08 (3H, m), 6.80-6.88 (1H, m), 7.51-7.64 (1H, m), 7.70-7.82 (1H, m). MS (ESI) m/z: 381 [M + Na] ⁺ |
| Ex. 96 | 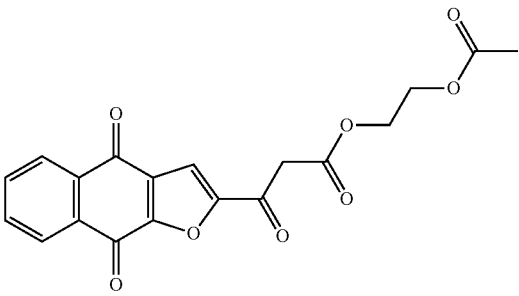 [SMILES: CC(=O)OCCOC(=O)CC(=O)c1cc2c(o1)C(=O)c1ccccc1C2=O] | ¹H-NMR (DMSO-d₆, 400 MHz) δ: 2.00 (2.7H, s), 2.05 (0.3H, s), 4.19-4.21 (2H, m), 4.24 (1.8H, m), 4.28-4.32 (2H, m), 6.02 (0.1H, s), 7.76 (0.1H, s), 7.90-7.95 (2H, m), 8.13-8.16 (2.9H, m), 11.81 (0.1H, s). MS (ESI) m/z: 393 [M + Na] ⁺ |
| Ex. 97 | 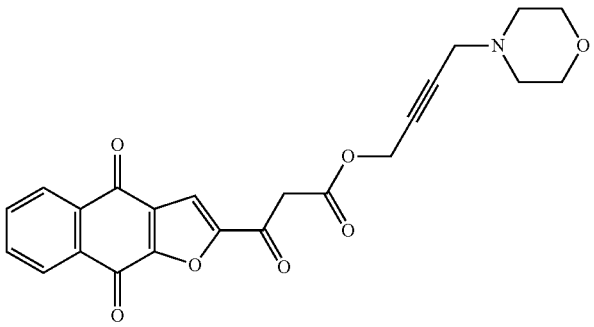 [SMILES: O=C(CC(=O)c1cc2c(o1)C(=O)c1ccccc1C2=O)OCC#CCN1CCOCC1] | ¹H-NMR (DMSO-d₆, 400 MHz) δ: 2.37-2.45 (4H, m), 3.28-3.31 (2H, m), 3.52-3.60 (4H, m), 4.29 (1.8H, s), 4.82-4.84 (1.8H, m), 4.90-4.94 (0.2H, m), 6.01 (0.1H, s), 7.75 (0.1H, s), 7.89-7.95 (2H, m), 8.10-8.19 (2.9H, m). MS (ESI) m/z: 422 [M + H] ⁺ |
| Ex. 98 | 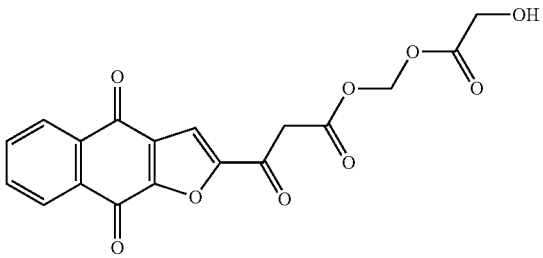 [SMILES: O=C(CO)OCOC(=O)CC(=O)c1cc2c(o1)C(=O)c1ccccc1C2=O] | ¹H-NMR (DMSO-d₆, 400 MHz) δ: 4.07 (2H, d, J = 5.4 Hz), 4.32 (1.6H, m), 5.45-5.55 (1H, m), 5.76-5.91 (2.2H, m), 7.75 (0.2H, s), 7.85-7.97 (2H, m), 8.07-8.22 (2.8H, m). MS (ESI) m/z: 395 [M + Na] ⁺ |
| Ex. 99 | 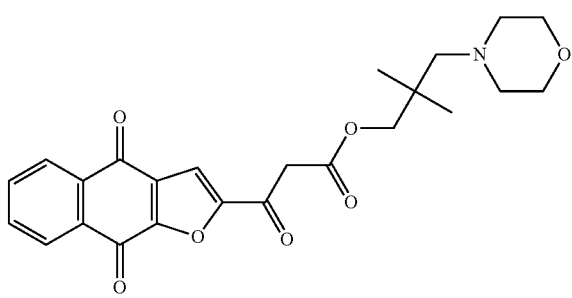 [SMILES: CC(C)(COC(=O)CC(=O)c1cc2c(o1)C(=O)c1ccccc1C2=O)CN1CCOCC1] | ¹H-NMR (DMSO-d₆, 400 MHz) δ: 0.80 (5.4H, s), 0.93 (0.6H, s), 2.05 (1.8H, s), 2.31-2.41 (3.8H, m), 2.56-2.62 (0.4H, m), 3.46-3.53 (3.6H, m), 3.60-3.66 (0.4H, m), 3.88 (1.8H, s), 3.97 (0.2H, s), 4.23 (1.8H, s), 5.82 (0.1H, s), 7.61 (0.1H, s), 7.88-7.98 (2H, m), 8.10-8.22 (2.9H, m). MS (ESI) m/z: 440 [M + H] ⁺ |

TABLE 1-15

| Ex. No. | structure | data |
|---|---|---|
| Ex. 100 | 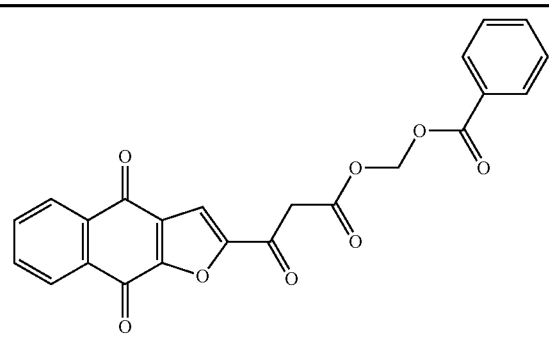 | ¹H-NMR (DMSO-d₆, 400 MHz) δ: 4.34 (1.8H, s), 6.00 (1.8H, s), 6.03 (0.1H, s), 6.10 (0.2H, s), 7.45-7.51 (1.8H, m), 7.54-7.59 (0.2H, m), 7.60-7.65 (0.9H, m), 7.68-7.74 (0.1H, m), 7.78 (0.1H, s), 7.88-8.02 (4H, m), 8.09-8.15 (2.9H, m), 11.61-11.74 (0.1H, br). MS (ESI) m/z: 441 [M + Na]⁺ |
| Ex. 101 | 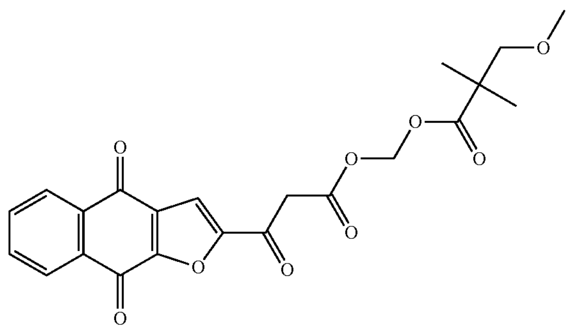 [SMILES: COCC(C)(C)C(=O)OCOC(=O)CC(=O)c1cc2c(o1)C(=O)c1ccccc1C2=O] | ¹H-NMR (DMSO-d₆, 400 MHz) δ: 1.10, 1.12 (total 6H, s, s), 3.20, 3.20 (total 3H, s, s), 4.31 (1.8H, s), 5.75 (1.8H, s), 5.84 (0.2H, s), 5.99 (0.1H, s), 7.78 (0.1H, s), 7.88-7.96 (2H, m), 8.11-8.18 (2.9H, m), 11.50-11.90 (0.1H, br). MS (ESI) m/z: 451 [M + Na]⁺ |
| Ex. 102 | 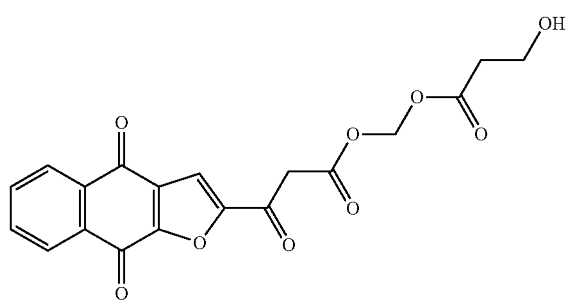 [SMILES: O=C(CCO)OCOC(=O)CC(=O)c1cc2c(o1)C(=O)c1ccccc1C2=O] | ¹H-NMR (DMSO-d₆, 400 MHz) δ: 2.48-2.55 (2H, m), 3.60-3.67 (2H, m), 4.31 (1.8H, s), 5.75 (1.8H, s), 5.85 (0.1H, s), 6.00 (0.1H, s), 7.79 (0.1H, s), 7.88-7.95 (2H, m), 8.09-8.17 (2.9H, m), 11.61-11.74 (0.1H, br). MS (ESI) m/z: 409 [M + Na]⁺ |
| Ex. 103 | 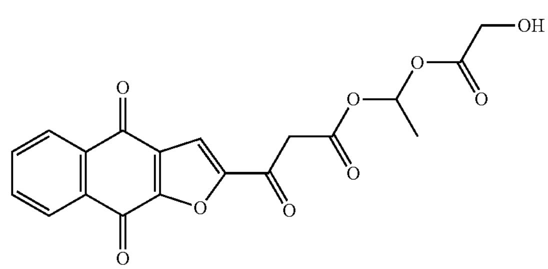 [SMILES: CC(OC(=O)CO)OC(=O)CC(=O)c1cc2c(o1)C(=O)c1ccccc1C2=O] | ¹H-NMR (DMSO-d₆, 400 MHz) δ: 1.45 (2.4H, d, J = 5.4 Hz), 1.51 (0.6H, d, J = 5.4 Hz), 3.95-4.10 (2H, m), 4.21-4.32 (1.6H, m), 5.46 (1H, d, J = 6.4 Hz), 5.97 (0.2H, s), 6.85 (0.8H, q, J = 5.4 Hz), 6.96 (0.1H, q, J = 5.4 Hz), 7.77 (0.2H, s), 7.88-7.96 (2H, m), 8.10-8.19 (2.8H, m), 11.65-11.97 (0.1H, br). MS (ESI) m/z: 409 [M + Na]⁺ |
| Ex. 104 | 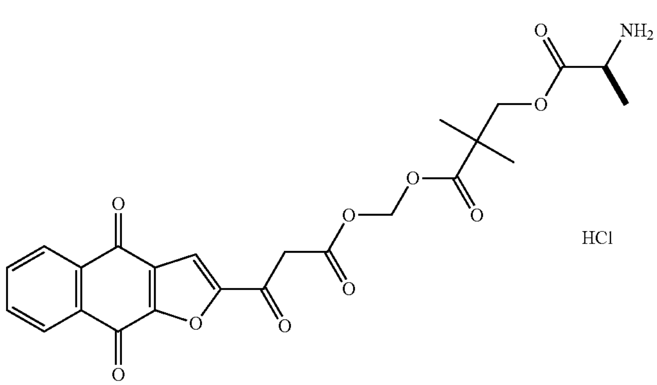 [SMILES: C[C@H](N)C(=O)OCC(C)(C)C(=O)OCOC(=O)CC(=O)c1cc2c(o1)C(=O)c1ccccc1C2=O ; Cl] | ¹H-NMR (DMSO-d₆, 400 MHz) δ: 1.19 (3H, s), 1.21 (3H, s), 1.37 (3H, d, J = 7.1 Hz), 4.07-4.17 (2H, m), 4.27-4.30 (1H, m), 4.33 (1.8H, s), 5.78 (1.8H, s), 5.85-5.90 (0.3H, m), 7.66-7.78 (0.1H, m), 7.88-7.98 (2H, m), 8.12-8.20 (2.9H, m), 8.30-8.45 (3H, m). MS (ESI) m/z: 486 [M + H]⁺ |

TABLE 1-15-continued

| Ex. No. | structure | data |
|---|---|---|
| Ex. 105 | (naphtho[2,3-b]furan-4,9-dione with 2-(2-hydroxyethoxy)ethyl 3-oxopropanoate substituent) | ¹H-NMR (DMSO-d₆, 400 MHz) δ: 3.39-3.53 (4H, m), 3.59-3.72 (2H, m), 4.20-4.34 (3.8H, s), 4.57 (1H, t, J = 5.2 Hz), 6.03 (0.1H, s), 7.76 (0.1H, s), 7.88-7.95 (2H, m), 8.10-8.17 (2.9H, m), 11.89-11.94 (0.1H, br). MS (ESI) m/z: 495 [M + Na] ⁺ |

TABLE 1-16

| Ex. No. | structure | data |
|---|---|---|
| Ex. 106 | (naphtho[2,3-b]furan-4,9-dione with carboxymethyl 3-oxopropanoate substituent) | ¹H-NMR (DMSO-d₆, 400 MHz) δ: 4.31 (1.8H, s), 4.65 (1.8H, s), 4.72 (0.2H, s), 6.04 (0.1H, s), 7.76 (0.1H, s), 7.88-7.95 (2H, m), 8.10-8.19 (2.9H, m). MS (ESI) m/z: 341 [M − H] ⁻ |
| Ex. 107 | (naphtho[2,3-b]furan-4,9-dione with 4-(2-aminoethyl)phenyl 3-oxopropanoate substituent, HCl) | ¹H-NMR (DMSO-d₆, 400 MHz) δ: 2.84-2.93 (2H, m), 2.98-3.09 (2H, m), 4.49 (1.8H, s), 6.19 (0.1H, s), 7.10-7.22 (2H, m), 7.29-7.37 (2H, m), 7.81 (0.1H, s), 7.87-7.98 (5H, m), 8.11-8.19 (2H, m), 8.23 (1H, s). MS (ESI) m/z: 404 [M + H] ⁺ |
| Ex. 108 | (naphtho[2,3-b]furan-4,9-dione with 2-morpholinoethyl 3-oxopropanoate substituent, HCl) | ¹H-NMR (DMSO-d₆, 400 MHz) δ: 3.04-3.18 (2H, m), 3.38-3.48 (4H, m), 3.72-3.84 (2H, m), 3.87-3.99 (2H, m), 4.30 (1.8H, s), 4.45-4.51 (1.8H, m), 4.57-4.64 (0.2H, m), 6.01 (0.1H, s), 7.70 (0.1H, s), 7.88-7.96 (2H, m), 8.10-8.18 (2H, m), 8.20 (0.9H, s), 10.80-11.05 (1H, br). MS (ESI) m/z: 398 [M + H] ⁺ |

TABLE 1-16-continued
| Ex. No. | structure | data |
|---|---|---|
| Ex. 109 | 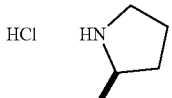 | ¹H-NMR (DMSO-d₆, 400 MHz) δ: 1.85-2.07 (3H, m), 2.22-2.34 (1H, m), 3.15-3.26 (2H, m), 4.36 (1.8H, s), 4.42-4.52 (1H, m), 5.80-5.97 (2H, m), 5.98 (0.1H, s), 7.80 (0.1H, s), 7.88-7.97 (2H, m), 8.08-8.23 (2.9H, m), 8.80-9.40 (1H, br), 9.70-10.50 (1H, br).<br>MS (ESI) m/z: 412 [M + H]⁺ |
| Ex. 110 | 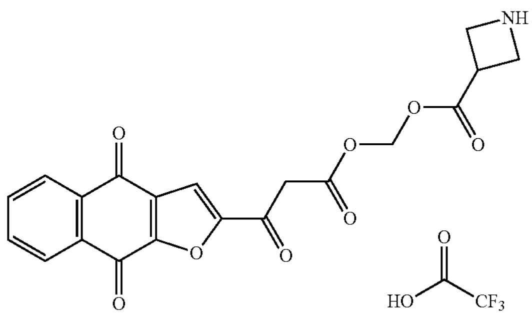 [SMILES: O=C(CC(=O)c1cc2c(o1)C(=O)c1ccccc1C2=O)OCOC(=O)C1CNC1 ; O=C(O)C(F)(F)F] | ¹H-NMR (DMSO-d₆, 400 MHz) δ: 3.76-3.85 (1H, m), 4.05-4.20 (4H, m), 4.34 (1.8H, s), 5.82 (1.6H, s), 5.90 (0.4H, s), 5.97 (0.1H, s), 7.78 (0.1H, s), 7.88-7.97 (2H, m), 8.10-8.20 (2.9H, m), 8.70-8.90 (2H, br).<br>MS (ESI) m/z: 398 [M + H]⁺ |
| Ex. 111 | 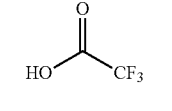 | ¹H-NMR (DMSO-d₆, 400 MHz) δ: 3.25-3.72 (7H, m), 4.20-4.27 (3.8H, m), 4.44 (1H, t, J = 5.6 Hz), 4.61 (1H, d, J = 4.9 Hz), 6.00 (0.1H, s), 7.74 (0.1H, s), 7.88-7.97 (2H, m), 8.10-8.18 (2.9H, m), 11.85-11.95 (0.1H, br).<br>MS (ESI) m/z: 425 [M + Na]⁺ |
TABLE 1-17
| Ex. No. | structure | data |
|---|---|---|
| Ex. 112 | 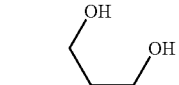 | ¹H-NMR (DMSO-d₆, 400 MHz) δ: 3.25-3.48 (5H, m), 3.68-3.77 (1.8H, m), 3.78-3.83 (0.2H, m), 4.17-4.26 (3.6H, m), 4.27-4.32 (0.2H, m), 4.47 (2H, t, J = 5.4 Hz), 5.96 (0.1H, s), 7.70 (0.1H, s), 7.87-7.97 (2H, m), 8.10-8.18 (2.9H, m).<br>MS (ESI) m/z: 425 [M + Na]⁺ |

TABLE 1-17-continued

| Ex. No. | structure | data |
|---|---|---|
| Ex. 113 | (naphthofuran-dione with pyridin-2-ylmethyl ester, HCl) | ¹H-NMR (DMSO-d₆, 400 MHz) δ: 4.36 (1.8H, s), 5.30 (1.8H, s), 5.40 (0.2H, s), 6.12 (0.1H, s), 7.41-7.62 (2H, m), 7.76 (0.1H, s), 7.89-7.99 (3H, m), 8.11-8.21 (2.9H, m), 8.58-8.65 (1H, m). MS (ESI) m/z: 398 [M + Na]⁺ |
| Ex. 114 | (naphthofuran-dione with 1-isopropylazetidin-3-yl ester, HCl) | ¹H-NMR (DMSO-d₆, 400 MHz) δ: 1.11-1.18 (6H, m), 3.38-3.51 (1H, m), 4.07-4.25 (2H, m), 4.30 (1.8H, s), 4.36-4.50 (2H, m), 5.2-5.31 (1H, br), 5.99 (0.1H, s), 7.79 (0.1H, s), 7.87-7.97 (2H, m), 8.08-8.21 (2.9H, m), 10.80-11.25 (1H, br). MS (ESI) m/z: 382 [M + H]⁺ |
| Ex. 115 | (naphthofuran-dione with 4-morpholinobut-2-ynyl ester, HCl) | ¹H-NMR (DMSO-d₆, 400 MHz) δ: 2.93-3.22 (4H, m), 3.62-4.08 (4H, m), 4.10-4.27 (2H, br), 4.32 (1.8H, s), 4.93 (1.8H, m), 5.02 (0.2H, m), 6.02 (0.1H, s), 7.78 (0.1H, s), 7.89-7.97 (2H, m), 8.10-8.21 (2.9H, m), 11.15-11.80 (1H, br). MS (ESI) m/z: 422 [M + H]⁺ |
| Ex. 116 | (naphthofuran-dione with 4-pyrrolidin-1-ylbut-2-ynyl ester, HCl) | ¹H-NMR (DMSO-d₆, 400 MHz) δ: 1.87-2.07 (4H, m), 2.97-3.57 (4H, m), 4.19-4.27 (2H, m), 4.32 (1.8H, s), 4.92 (1.8H, m), 5.00 (0.2H, m), 6.02 (0.1H, s), 7.79 (0.1H, s), 7.90-7.99 (2H, m), 8.11-8.23 (2.9H, m), 10.96-11.42 (1H, br). MS (ESI) m/z: 406 [M + H]⁺ |
| Ex. 117 | (naphthofuran-dione with (1H-tetrazol-5-yl)methyl ester) | ¹H-NMR (DMSO-d₆, 400 MHz) δ: 4.33 (1.8H, s), 5.51 (1.8H, s), 5.59 (0.2H, s), 6.06 (0.1H, s), 7.76 (0.1H, s), 7.89-7.96 (2H, m), 8.10-8.19 (2.9H, m). MS (ESI) m/z: 365 [M − H]⁻ |

TABLE 1-18

| Ex. No. | structure | data |
|---|---|---|
| Ex. 118 | 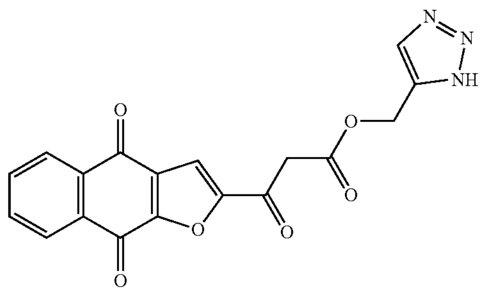 [SMILES: O=C(CC(=O)c1cc2c(o1)C(=O)c1ccccc1C2=O)OCc1cnn[nH]1] | $^1$H-NMR (DMSO-$d_6$, 400 MHz) δ: 4.26 (1.8H, s), 5.26 (1.8H, s), 5.36 (0.2H, s), 6.02 (0.1H, s), 7.75 (0.1H, s), 7.88-7.95 (2.9H, m), 7.98 (0.1H, s), 8.10-8.18 (2.9H, m). MS (ESI) m/z: 366 [M + H]$^+$ |
| Ex. 119 | 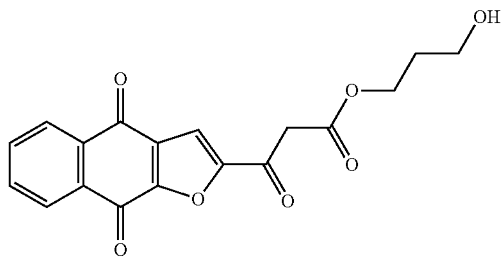 [SMILES: O=C(CC(=O)c1cc2c(o1)C(=O)c1ccccc1C2=O)OCCCO] | $^1$H-NMR (DMSO-$d_6$, 400 MHz) δ: 1.69-1.82 (2H, m), 3.40-3.53 (2H, m), 4.14-4.17 (1.8H, m), 4.20 (1.8H, s), 4.25-4.28 (0.2H, m), 4.51 (1H, t, J = 5.1 Hz), 5.98 (0.1H, s), 7.72 (0.1H, s), 7.88-7.98 (2H, m), 8.10-8.19 (2.9H, m). MS (ESI) m/z: 365 [M + Na]$^+$ |
| Ex. 120 | 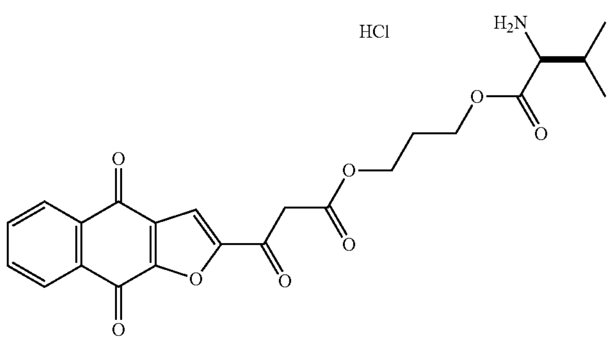 [SMILES: CC(C)[C@H](N)C(=O)OCCCOC(=O)CC(=O)c1cc2c(o1)C(=O)c1ccccc1C2=O ; Cl] | $^1$H-NMR (DMSO-$d_6$, 400 MHz) δ: 0.93-1.01 (6H, m), 1.93-2.07 (2H, m), 2.10-2.26 (1H, m), 3.84-3.94 (1H, m), 4.19-4.31 (5.8H, m), 6.01 (0.1H, s), 7.74 (0.1H, s), 7.90-7.98 (2H, m), 8.12-8.20 (2.9H, m), 8.38-8.63 (3H, m). MS (ESI) m/z: 442 [M + H]$^+$ |
| Ex. 121 | 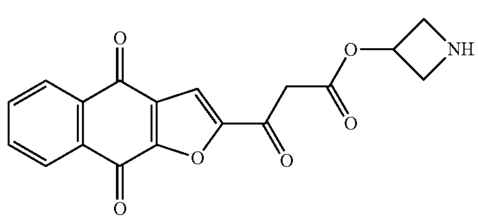 | $^1$H-NMR (DMSO-$d_6$, 400 MHz) δ: 3.95-4.13 (2H, m), 4.26-4.35 (3.8H, m), 5.25-5.38 (1H, m), 5.99 (0.1H, s), 7.78 (0.1H, s), 7.88-7.99 (2H, m), 8.10-8.23 (2.9H, m), 8.70-9.30 (2H, br). MS (ESI) m/z: 340 [M + H]$^+$ |
| Ex. 122 | 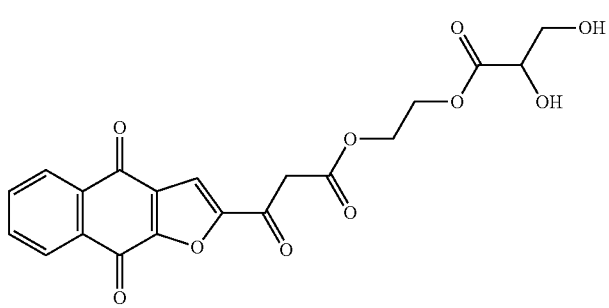 [SMILES: O=C(CC(=O)c1cc2c(o1)C(=O)c1ccccc1C2=O)OCCOC(=O)C(O)CO] | $^1$H-NMR (DMSO-$d_6$, 400 MHz) δ: 3.46-3.62 (2H, m), 4.00-4.12 (1H, m), 4.21-4.43 (5.8H, m), 4.80 (1H, t, J = 5.9 Hz), 5.37 (0.9H, d, J = 6.1 Hz), 5.44 (0.1H, d, J = 6.1 Hz), 6.00 (0.1H, s), 7.75 (0.1H, s), 7.88-7.97 (2H, m), 8.10-8.8 (2.9H, m). MS (ESI) m/z: 439 [M + Na]$^+$ |

TABLE 1-18-continued
| Ex. No. | structure | data |
|---|---|---|
| Ex. 123 | 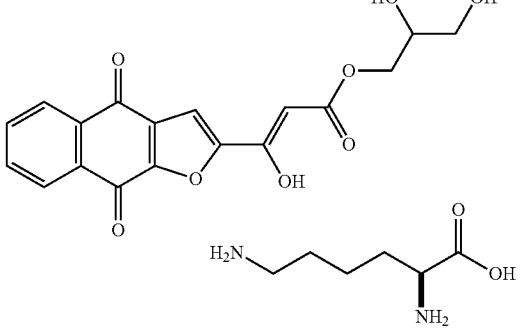 | $^1$H-NMR (DMSO-$d_6$, 400 MHz) δ: 1.22-1.42 (2H, m), 1.53-1.62 (2H, m), 1.68-1.78 (2H, m), 2.87 (2H, t, J = 7.6 Hz), 3.48-3.69 (3H, m), 3.83-3.98 (2H, m), 4.03 (1H, dd, J = 11.5, 3.7 Hz), 6.79-6.84 (1H, m), 7.51-7.60 (2H, m), 7.68-7.80 (2.0H). MS (ESI) m/z: 357 [M − H]$^−$, 381 [M + Na]$^+$ |
TABLE 1-19
| Ex. No. | structure | data |
|---|---|---|
| Ex. 124 | 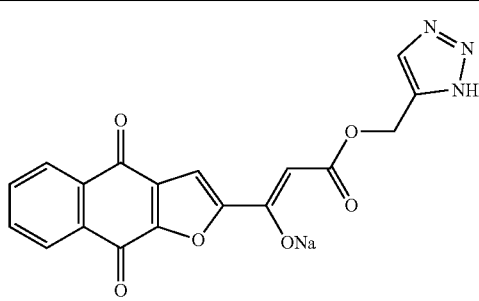 | $^1$H-NMR (DMSO-$d_6$, 400 MHz) δ: 5.00 (2H, s), 5.12 (1H, s), 7.07 (1H, s), 7.65 (1H, s), 7.80-7.90 (2H, m), 8.10-8.18 (2H, m). MS (ESI) m/z: 388 [M + Na]$^+$ |
| Ex. 125 | 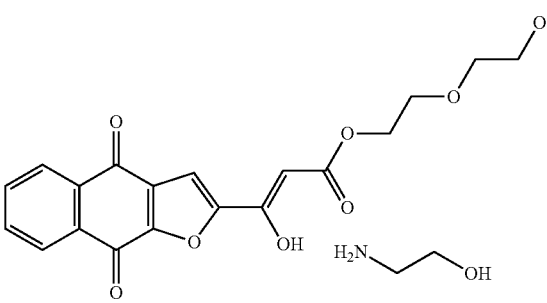 | $^1$H-NMR (DMSO-$d_6$, 400 MHz) δ: 2.82 (2H, t, J = 5.5 Hz), 3.46-3.66 (8H, m), 3.96-4.04 (2H, m), 4.17-4.32 (1H, br), 5.07 (1H, s), 7.06 (1H, s), 7.81-7.95 (2H, m), 8.04-8.20 (2H, m). MS (ESI) m/z: 395 [M + Na]$^+$ |
| Ex. 126 | 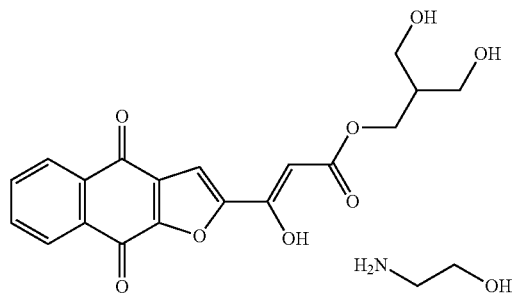 | $^1$H-NMR (DMSO-$d_6$, 400 MHz) δ: 1.75-1.89 (1H, m), 2.82 (2H, t, J = 5.4 Hz), 3.41-3.48 (4H, m), 3.55 (2H, t, J = 5.4 Hz), 3.86-4.20 (2H, m), 5.02 (1H, s), 7.05 (1H, s), 7.80-7.92 (2H, m), 8.05-8.15 (2H, m). MS (ESI) m/z: 395 [M + Na]$^+$ |

TABLE 1-19-continued

| Ex. No. | structure | data |
|---|---|---|
| Ex. 127 | 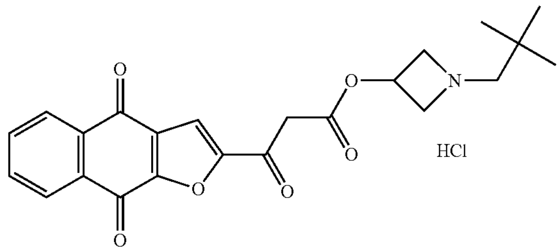 [SMILES: CC(C)(C)CN1CC(OC(=O)CC(=O)c2cc3c(o2)C(=O)c2ccccc2C3=O)C1 ; Cl] | $^1$H-NMR (DMSO-d$_6$, 400 MHz) δ: 0.96, 0.98 (total 9H, s, s), 3.15, 3.18 (total 2H, s, s), 4.15-4.70 (4H, m), 4.30 (1.8H, s), 5.15-5.35 (1H, m), 5.98 (0.1H, s), 7.80 (0.1H, s), 7.88-7.95 (2H, m), 8.10-8.17 (2H, m), 8.20 (0.9H, s), 10.15-10.40 (1H, br). MS (ESI) m/z: 410 [M + H]$^+$ |
| Ex. 128 | 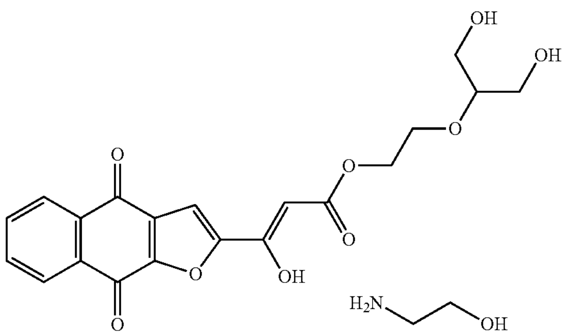 | $^1$H-NMR (DMSO-d$_6$, 400 MHz) δ: 2.84 (2H, t, J = 5.4 Hz), 3.10-4.10 (11H, m), 5.08 (1H, s), 7.07 (1H, s), 7.82-8.00 (2H, m), 8.05-8.25 (2H, m). MS (ESI) m/z: 425 [M + Na]$^+$ |
| Ex. 129 | 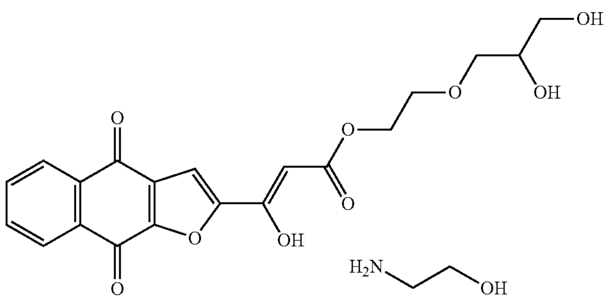 | $^1$H-NMR (DMSO-d$_6$, 400 MHz) δ: 2.97 (2H, t, J = 4.9 Hz), 3.40-3.60 (4H, m), 3.63-3.75 (4H, m), 3.76-3.85 (1H, m), 4.03-4.13 (2H, m), 4.22-4.30 (0.2H, s), 6.75 (1H, s), 7.45-7.57 (2H, m), 7.60-7.71 (2H, m) MS (ESI) m/z: 425 [M + Na]$^+$ |

TABLE 1-20

| Ex. No. | structure | data |
|---|---|---|
| Ex. 130 | 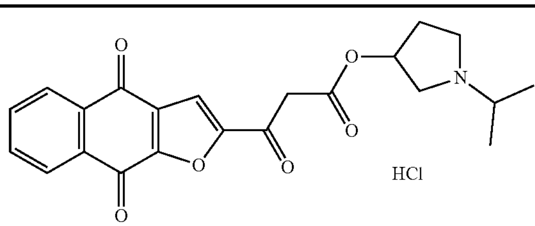 | $^1$H-NMR (DMSO-d$_6$, 400 MHz) δ: 1.23-1.34 (6H, m), 2.00-2.45 (2H, m), 3.05-3.28 (2H, m), 3.37-3.62 (2.7H, m), 3.70-3.87 (0.3H, m), 4.25 (1.8H, s), 5.33-5.47 (1H, m), 5.95 (0.1H, s), 7.73 (0.1H, s), 7.88-7.97 (2H, m), 8.10-8.24 (2.9H, m), 10.62-11.24 (1H, br) MS (ESI) m/z: 396 [M + H]$^+$ |
| Ex. 131 | 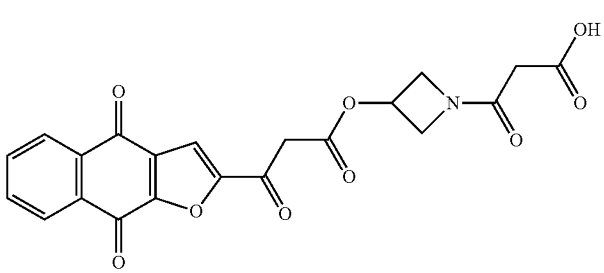 [SMILES: O=C(O)CC(=O)N1CC(OC(=O)CC(=O)c2cc3c(o2)C(=O)c2ccccc2C3=O)C1] | $^1$H-NMR (DMSO-d$_6$, 400 MHz) δ: 3.13-3.22 (2H, m), 3.80-3.93 (1H, m), 4.09-4.19 (1H, m), 4.19-4.27 (1H, m), 4.30 (1.8H, s), 4.46-4.56 (1H, m), 5.19-5.35 (1H, m), 6.03 (0.1H, s), 7.74 (0.1H, s), 7.87-7.96 (2H, m), 8.09-8.18 (2.9H, m), 11.19-13.19 (1H, br). MS (ESI) m/z: 424 [M − H]$^-$ |

TABLE 1-20-continued
| Ex. No. | structure | data |
|---|---|---|
| Ex. 132 | 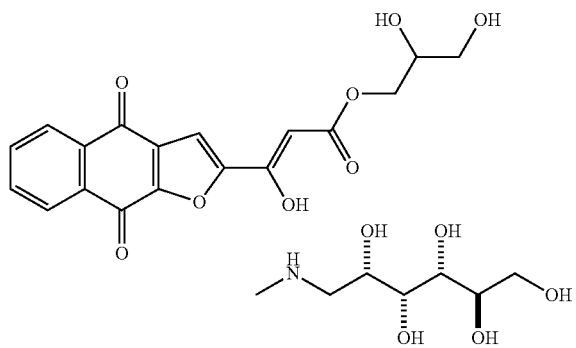 [SMILES: O=C(/C=C(\O)c1cc2c(o1)C(=O)c1ccccc1C2=O)OCC(O)CO ; CNC[C@H](O)[C@@H](O)[C@H](O)[C@H](O)CO] | ¹H-NMR (DMSO-d₆, 400 MHz) δ: 2.75 (3H, s), 3.11-3.24 (2H, m), 3.60-3.84 (7H, m), 3.97-4.18 (4H, m), 6.84-6.87 (1H, m), 7.60-7.66 (2H, m), 7.73-7.80 (2H, m).<br>MS (ESI) m/z: 381 [M + Na]⁺ |
| Ex. 133 | 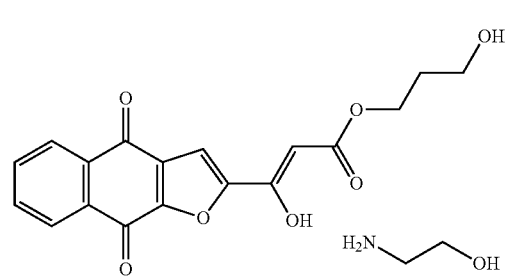 | ¹H-NMR (DMSO-d₆, 400 MHz) δ: 1.65-1.78 (2H, m), 2.81 (2H, t, J = 5.4 Hz), 3.49-3.58 (4H, m), 3.91-3.99 (2H, m), 4.09-4.30 (1H, br), 5.05 (1H, s), 7.06 (1H, s), 7.81-7.97 (2H, m), 8.03-8.22 (2H, m).<br>MS (ESI) m/z: 365 [M + Na]⁺ |
| Ex. 134 | 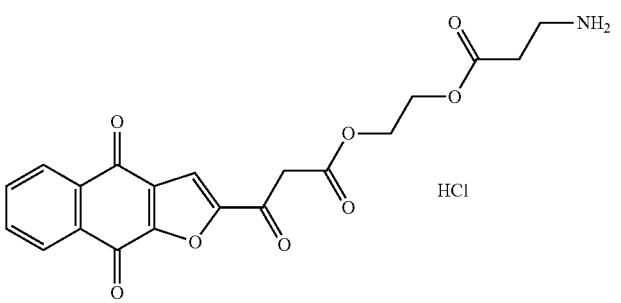 [SMILES: NCCC(=O)OCCOC(=O)CC(=O)c1cc2c(o1)C(=O)c1ccccc1C2=O ; Cl] | ¹H-NMR (DMSO-d₆, 400 MHz) δ: 2.66-2.77 (2H, m), 2.97-3.09 (2H, m), 4.25-4.32 (3.8H, m), 4.34-4.38 (2H, m), 6.01 (0.1H, s), 7.76 (0.1H, s), 7.85-8.05 (5H, m), 8.10-8.19 (2.9H, m).<br>MS (ESI) m/z: 400 [M + H]⁺ |
| Ex. 135 | 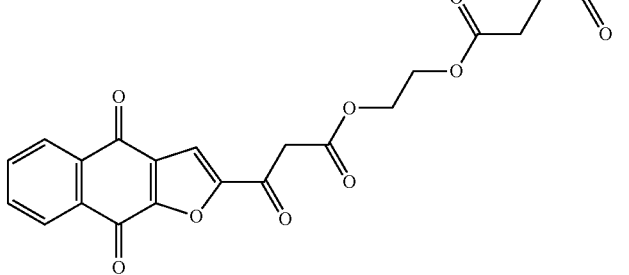 | ¹H-NMR (DMSO-d₆, 400 MHz) δ: 2.65-2.77 (4H, m), 4.08 (1H, s), 4.33-4.45 (4H, m), 6.08 (0.5H, s), 7.75 (0.5H, s), 7.75-7.85 (2H, m), 8.18-8.30 (2H, m), 11.65-11.80 (0.5H, br).<br>MS (ESI) m/z: 427 [M − H]⁻ |

TABLE 1-21

| Ex. No. | structure | data |
|---|---|---|
| Ex. 136 | 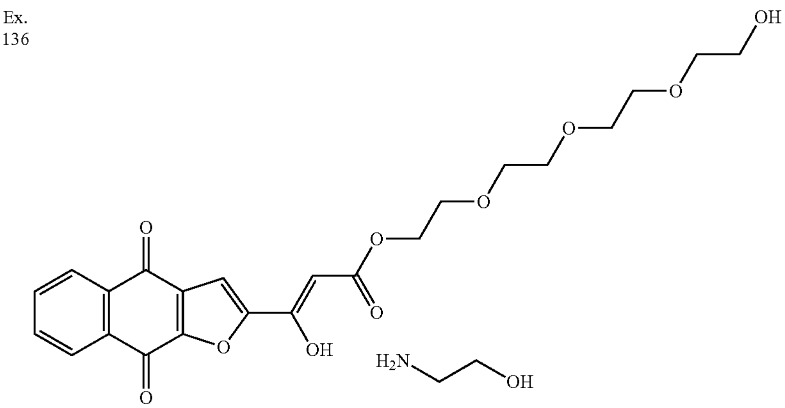 | $^1$H-NMR (DMSO-d$_6$, 400 MHz) δ: 2.84 (2H, t, J = 5.4 Hz), 3.45-3.59 (16H, m), 3.96-4.03 (1.6H, br), 4.15-4.30 (0.4H, m), 5.09 (1H, s), 7.08 (1H, s), 7.82-7.91 (2H, m), 8.04-8.15 (2H, m). MS (ESI) m/z: 522 [M + H]$^+$ |
| Ex. 137 | 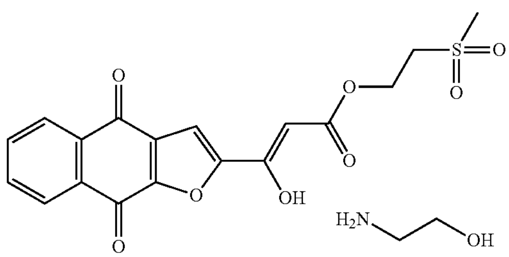 | $^1$H-NMR (DMSO-d$_6$, 400 MHz) δ: 2.85 (2H, t, J = 5.4 Hz), 3.14 (3H, s), 3.30-3.50 (2H, m), 3.57 (2H, t, J = 5.1 Hz), 4.17-4.25 (2H, m), 5.01 (1H, s), 5.05-5.15 (1H, br), 7.07 (1H, s), 7.82-7.91 (2H, m), 8.04-8.15 (2H, m). MS (ESI) m/z: 389 [M − H]$^−$, 413 [M + Na]$^+$ |
| Ex. 138 | 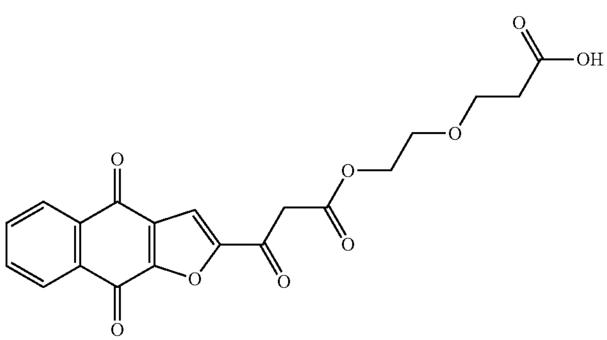 [SMILES: O=C(O)CCOCCOC(=O)CC(=O)c1cc2c(o1)C(=O)c1ccccc1C2=O] | $^1$H-NMR (DMSO-d$_6$, 400 MHz) δ: 2.39-2.47 (2H, m), 3.57-3.69 (4H, m), 4.18-4.33 (3.8H, m), 6.03 (0.1H, s), 7.76 (0.1H, s), 7.88-7.97 (2H, m), 8.09-8.20 (2.9H, m), 11.86-11.95 (0.1H, br), 12.03-12.36 (1H, br). MS (ESI) m/z: 399 [M − H]$^−$ |
| Ex. 139 | 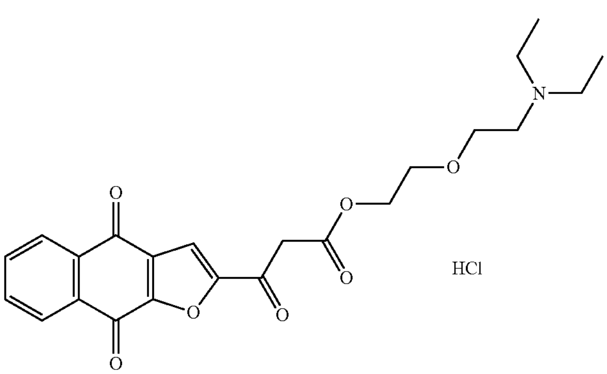 [SMILES: CCN(CC)CCOCCOC(=O)CC(=O)c1cc2c(o1)C(=O)c1ccccc1C2=O ; Cl] | $^1$H-NMR (DMSO-d$_6$, 400 MHz) δ: 1.20 (6H, t, J = 7.3 Hz), 3.05-3.18 (4H, m), 3.21-3.27 (2H, m), 3.65-3.83 (4H, m), 4.22-4.35 (3.8H, m), 6.00 (0.1H, s), 7.76 (0.1H, s), 7.88-7.98 (2H, m), 8.11-8.19 (2.9H, m), 9.70-10.05 (1H, br) MS (ESI) m/z: 426 [M − H]$^−$, 428 [M + H]$^+$ |

TABLE 1-21-continued

| Ex. No. | structure | data |
|---|---|---|
| Ex. 140 | (naphtho[2,3-b]furan-4,9-dione with 2-substituent: C(OH)=CH-C(=O)-O-CH2CH2-S(=O)2-CH2CH2-OH; H2N-CH2CH2-OH counterion) | $^1$H-NMR (DMSO-d$_6$, 400 MHz) δ: 2.85 (2H, t, J = 5.4 Hz), 3.36-3.43 (2H, m), 3.52 (2H, t, J = 4.9 Hz), 3.56 (2H, t, J = 5.4 Hz), 3.83 (2H, t, J = 4.9 Hz), 4.24 (2H, t, J = 4.9 Hz), 4.96 (1H, s), 5.00-5.15 (1H, br), 7.08 (1H, s), 7.83-7.89 (2H, m), 8.07-8.11 (2H, m). MS (ESI) m/z: 443 [M + Na]$^+$ |
| Ex. 141 | (naphtho[2,3-b]furan-4,9-dione-2-yl-C(=O)-CH2-C(=O)-O-CH2CH2-S(=O)2-CH2CH2-NH2 · HCl) | $^1$H-NMR (DMSO-d$_6$, 400 MHz) δ: 3.20-3.30 (2H, m), 3.50-3.63 (2H, m), 3.70 (1.8H, t, J = 5.6 Hz), 3.77 (0.2H, t, J = 5.6 Hz), 4.32 (1.8H, s), 4.48 (1.8H, t, J = 5.6 Hz), 4.56 (0.2H, t, J = 5.6 Hz), 6.08 (0.1H, s), 7.79 (0.1H, s), 7.89-7.98 (2H, m), 8.08-8.25 (5.9H, m). MS (ESI) m/z: 418 [M − H]$^−$, 420 [M + H]$^+$ |

TABLE 1-22

| Ex. No. | structure | data |
|---|---|---|
| Ex. 142 | (naphtho[2,3-b]furan-4,9-dione-2-yl-C(=O)-CH2-C(=O)-O-CH2CH2-O-C(=O)-CH(NH2)-CH2-Ph · HCl) | $^1$H-NMR (DMSO-d$_6$, 400 MHz) δ: 3.04-3.21 (2H, m), 4.24-4.38 (6.8H, m), 5.93 (0.1H, s), 7.19-7.34 (5H, m), 7.74 (0.1H, s), 7.91-7.95 (2H, m), 8.11-8.17 (2.9H, m), 8.40-8.70 (3H, br). MS (ESI) m/z: 476 [M + H]$^+$ |
| Ex. 143 | (naphtho[2,3-b]furan-4,9-dione-2-yl-C(=O)-CH2-C(=O)-O-CH2CH2-O-CH2CH2-C(=O)-NH-S(=O)2-CH3) | $^1$H-NMR (DMSO-d$_6$, 400 MHz) δ: 2.52-2.57 (2H, m), 3.19-3.23 (3H, m), 3.57-3.70 (4H, m), 4.18-4.33 (3.8H, m), 6.02 (0.1H, s), 7.75 (0.1H, s), 7.89-7.96 (2H, m), 8.10-8.17 (2.9H, m), 11.63-11.82 (1H, br). MS (ESI) m/z: 500 [M + Na]$^+$ |

TABLE 1-22-continued

| Ex. No. | structure | data |
|---|---|---|
| Ex. 144 | 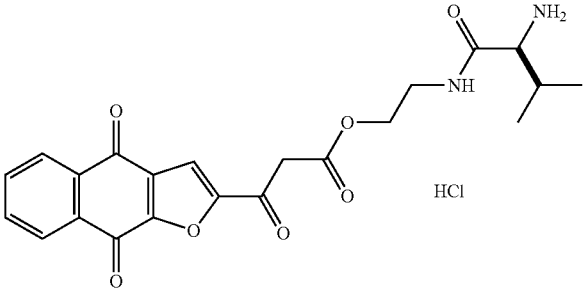 | $^1$H-NMR (DMSO-d$_6$, 400 MHz) δ: 0.87-1.02 (6H, m), 2.00-2.15 (1H, m), 2.92, 2.97, 3.08, 3.14 (total 3H, s, s, s, s), 3.38-3.45 (2H, m), 3.77-3.90 (1H, m), 4.15-4.30 (4H, m), 5.93-6.14 (total 0.1 H, s, s), 7.72, 7.78 (total 0.1H, s, s), 7.88-7.99 (2H, m), 8.06-8.20 (6H, m).<br>MS (ESI) m/z: 441 [M + H]$^+$ |
| Ex. 145 | 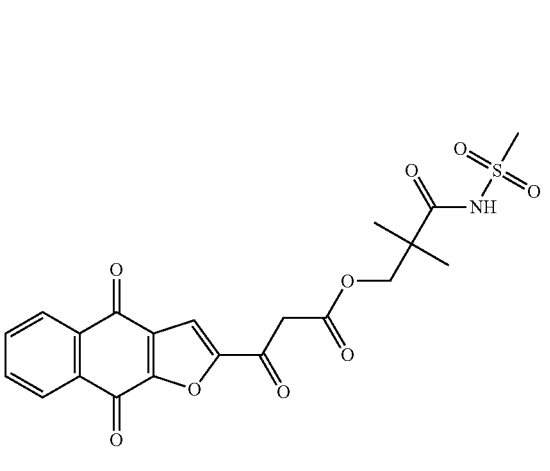 [SMILES: CC(C)(COC(=O)CC(=O)c1cc2c(o1)C(=O)c1ccccc1C2=O)C(=O)NS(C)(=O)=O] | $^1$H-NMR (DMSO-d$_6$, 400 MHz) δ: 1.13 (6H, s), 3.18, 3.22 (total 3H, s, s), 4.18-4.30 (3.8H, m), 5.99 (0.1H, s), 7.75 (0.1H, s), 7.88-7.98 (2H, m), 8.12-8.20 (2.9H, m), 11.38-11.55 (1H, br).<br>MS (ESI) m/z: 484 [M + Na]$^+$ |
| Ex. 146 | 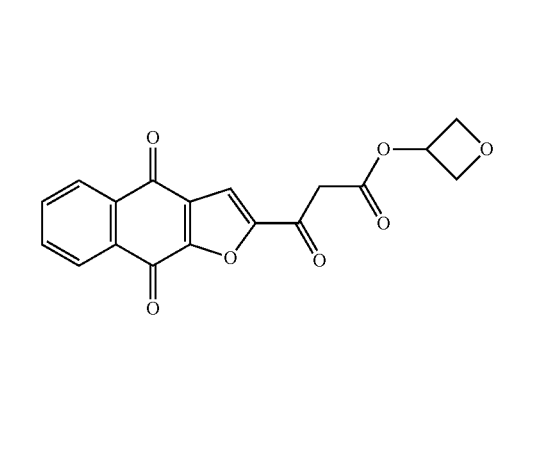 [SMILES: O=C(CC(=O)c1cc2c(o1)C(=O)c1ccccc1C2=O)OC1COC1] | $^1$H-NMR (DMSO-d$_6$, 400 MHz) δ: 4.30 (1.8H, s), 4.48-4.61 (2H, m), 4.78-4.87 (2H, m), 5.43-5.54 (1H, m), 6.06 (0.1H, s), 7.77 (0.1H, s), 7.88-7.98 (2H, m), 8.10-8.18 (2.9H, m).<br>MS (ESI) m/z: 363 [M + Na]$^+$ |
| Ex. 147 | 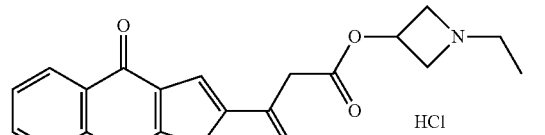 | $^1$H-NMR (DMSO-d$_6$, 400 MHz) δ: 1.10 (2.7H, t, J = 7.1 Hz), 1.17 (0.3H, t, J = 7.1 Hz), 3.15-3.25 (2H, m), 4.00-4.27 (2H, br), 4.31 (1.8H, s), 4.31-4.53 (2H, br), 5.12-5.45 (1H, br), 5.99 (0.1H, s), 7.79 (0.1H, s), 7.87-7.98 (2H, m), 8.08-8.21 (2.9H, m), 10.70-11.25 (1H, br).<br>MS (ESI) m/z: 366 [M − H]$^-$, 368 [M + H]$^+$ |

TABLE 1-23

| Ex. No. | structure | data |
|---|---|---|
| Ex. 148 | 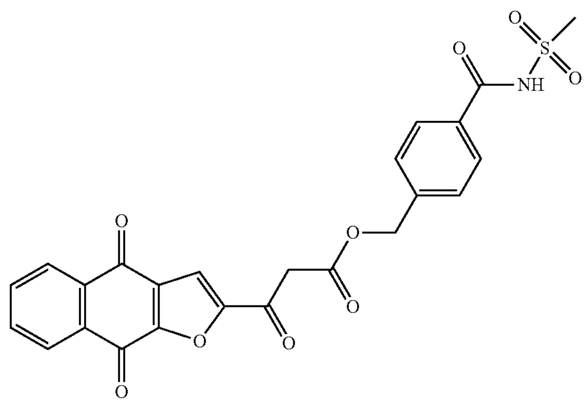 [SMILES: CS(=O)(=O)NC(=O)c1ccc(COC(=O)CC(=O)c2cc3c(o2)C(=O)c2ccccc2C3=O)cc1] | ¹H-NMR (DMSO-d₆, 400 MHz) δ: 3.29 (3H, s), 4.34 (1.8H, s), 5.26 (1.8H, s), 5.34 (0.2H, s), 6.05-6.15 (0.1H, br), 7.44-7.56 (2H, m), 7.69-7.77 (0.1H, br), 7.88-7.98 (4H, m), 8.09-8.19 (2.9H, m), 11.86-12.40 (1H, br). MS (ESI) m/z: 518 [M + Na]⁺ |
| Ex. 149 | 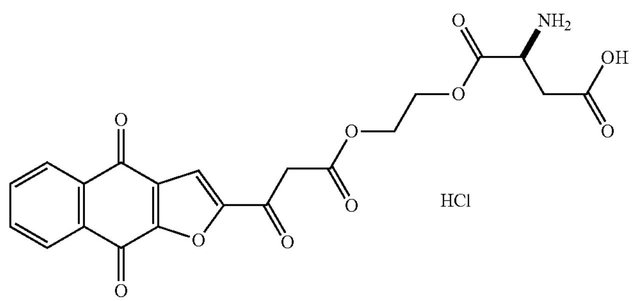 [SMILES: N[C@@H](CC(=O)O)C(=O)OCCOC(=O)CC(=O)c1cc2c(o1)C(=O)c1ccccc1C2=O ; Cl] | ¹H-NMR (DMSO-d₆, 400 MHz) δ: 2.80-2.95 (2H, m), 4.23 (1.8H, s), 4.29-4.49 (5H, m), 5.96 (0.1H, s), 7.73 (0.1H, s), 7.89-7.98 (2H, m), 8.09-8.19 (2.9H, m), 8.27-8.50 (3H, br). MS (ESI) m/z: 444 [M + H]⁺ |
| Ex. 150 | 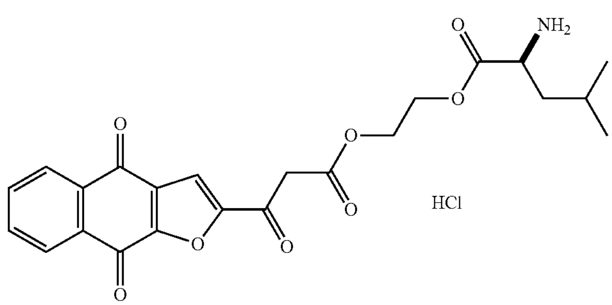 [SMILES: CC(C)C[C@H](N)C(=O)OCCOC(=O)CC(=O)c1cc2c(o1)C(=O)c1ccccc1C2=O ; Cl] | ¹H-NMR (DMSO-d₆, 400 MHz) δ: 0.89 (6H, d, J = 6.4 Hz), 1.56-1.82 (3H, m), 3.92-4.01 (1H, m), 4.25 (1.8H, s), 4.32-4.55 (4H, m), 5.96 (0.1H, s), 7.75 (0.1H, s), 7.88-7.98 (2H, m), 8.10-8.22 (2.9H, m), 8.43-8.65 (3H, br). MS (ESI) m/z: 442 [M + H]⁺ |
| Ex. 151 | 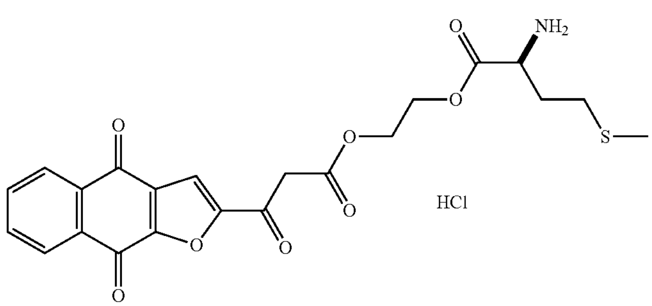 [SMILES: CSCC[C@H](N)C(=O)OCCOC(=O)CC(=O)c1cc2c(o1)C(=O)c1ccccc1C2=O ; Cl] | ¹H-NMR (DMSO-d₆, 400 MHz) δ: 1.99-2.13 (5H, m), 2.53-2.70 (2H, m), 4.06-4.18 (1H, m), 4.26 (1.8H, s), 4.31-4.52 (4H, m), 5.97 (0.1H, s), 7.74 (0.1H, s), 7.87-7.99 (2H, m), 8.08-8.20 (2.9H, s), 8.55-8.75 (3H, br). MS (ESI) m/z: 460 [M + H]⁺ |

TABLE 1-23-continued

| Ex. No. | structure | data |
|---|---|---|
| Ex. 152 | [structure with naphthofuran-dione, ester linker to glutamic acid derivative, CF₃CO₂H salt] | ¹H-NMR (DMSO-d₆, 400 MHz) δ: 1.85-2.09 (2H, m), 2.48-2.55 (2H, m), 3.53-3.59 (1H, m), 4.20-4.38 (6H, m), 7.88-7.96 (2H, m), 8.07-8.23 (3H). MS (ESI) m/z: 458 [M + H]⁺ |
| Ex. 153 | [structure with naphthofuran-dione, ester linker to alanine, HCl salt] | ¹H-NMR (DMSO-d₆, 400 MHz) δ: 1.37-1.44 (3H, m), 1.93-2.06 (2H, m), 4.03-4.14 (1H, m), 4.17-4.31 (5.8H, m), 6.02 (0.1H, s), 7.75 (0.1H, s), 7.91-7.95 (2H, m), 8.11-8.17 (2.9H, m), 8.40-8.60 (3H, br). MS (ESI) m/z: 414 [M + H]⁺ |
| Ex. 154 | [structure with naphthofuran-dione, ester linker to serine, HCl salt] | ¹H-NMR (DMSO-d₆, 400 MHz) δ: 1.91-2.08 (2H, m), 3.74-3.92 (2H, m), 4.11-4.33 (6.8H, m), 5.55-5.63 (1H, m), 6.02 (0.1H, s), 7.75 (0.1H, s), 7.89-7.96 (2H, m), 8.10-8.18 (2.9H, m), 8.33-8.56 (3H, br). MS (ESI) m/z: 430 [M + H]⁺ |

Experimental Example 1: Plasma Concentration after Oral Administration to Rat

Compound (A) or Example compound suspended in 0.5% methylcellulose solution was administered by gavage to male SD rats at a dose of 30 mg/kg or 100 mg/kg, respectively. At 0.25, 0.5, 1, 3, 5, 8 and 24 hr after administration, blood samples were collected from the cervical vein with a 1 mL syringe to which heparin was added. Using HPLC, the plasma concentration of compound (A) was determined.

After administration of the compound of Example 1-4, 6-9, 11, 12, 15-19, 22, 25, 26, 30-33, 35, 37-42, 48-53, 55-57, 60-64, 67, 68, 70, 72-75, 83, 85 or 86, compound (A) emerged in the plasma over time. The maximum plasma concentration of compound (A) at the time was markedly higher than that by the administration of compound (A) itself.

Experimental Example 2: Blood Concentration after Oral Administration to Rat or Dog Compound (A) or Example compound suspended in 0.5% methylcellulose solution was administered by gavage to male SD rat or male beagle at a dose of 30 mg/kg or 100 mg/kg, respectively. At 0.25, 0.5, 1, 2, 4, 6 and 24 hr after administration, blood samples were collected from the cervical vein with a 1 mL syringe and was added in a 2.0 mL tube to which heparin was added. The blood was treated with acetonitrile, and the blood concentration of compound (A) was determined by using HPLC or LC-MS/MS.

After administration of the compound of Example 13, 54, 60, 65, 66, 74, 75, 79, 88, 93, 95, 114, 116, 120, 125, 126, 129 or 133, compound (A) emerged in the blood over time. The maximum blood concentration of compound (A) at the time was higher than that by the administration of compound (A) itself.

Experimental Example 3: Metabolism by Plasma and Liver Microsome

Hydrolysis by plasma: The plasma (495 μL) of human or SD rat was added in a 1.5 mL plastic tube, 100 μg/mL test compound solution (5 μL) was added thereto in a warm bath at 37° C. After 15, 30 and 60 min, the reaction mixture was collected by 50 μL, acetonitrile (50 μL) was added and mixed, and the mixture was centrifuged at 12,000×g, 4° C. for 3 min. The concentration of compound (A) in the supernatant was measured by HPLC.

Hydrolysis by liver microsome: 0.5 M Phosphate buffer (100 μL), NADPH regeneration system solution A (25 μL), NADPH regeneration system solution B (5 μL), ultra-pure water (353 μL) and 100 μg/mL test compound solution (5 μL) were added in a 1.5 mL plastic tube, and 20 mg protein/mL human, beagle or SD rat liver microsome suspension (11.3 μL) was added thereto to start the reaction. After 15, 30 and 60 min, the reaction mixture was collected by 50 μL, acetonitrile (50 μL) was added thereto, respectively, and mixed, and the mixture was centrifuged at 12,000×g, 4° C. for 3 min. The concentration of compound (A) in the supernatant was measured by HPLC.

The compounds of Examples 1-5, 8, 9, 12, 15, 19, 22, 23, 30, 60, 61, 69, 72-75, 93, 95-98, 105, 108, 111, 112, 114, 118-120, 134, 136, 137, 140, 141, 146 and 147 were rapidly converted to compound (A) by the plasma and liver microsome of rat. In addition, they were gradually converted to compound (A) in human plasma, and markedly and rapidly converted to compound (A) in human or beagle liver microsome.

INDUSTRIAL APPLICABILITY

The compound of the present invention or a pharmaceutically acceptable salt thereof is effective as a prodrug of a naphthofuran compound useful as an anticancer agent, or an agent for the prophylaxis or treatment of cancer metastasis and/or cancer recurrence. In addition, a medicament containing the compound of the present invention shows high oral absorbability and less side effects, and therefore, it can be a highly safe therapeutic agent for cancer or an agent for the prophylaxis or treatment of cancer metastasis and/or cancer recurrence.

The present invention is based on patent application Nos. 2014-119113 and 2015-021492 filed in Japan, the contents of which are incorporated in full herein.

The invention claimed is:

1. A production method of a compound represented by formula (Ia):

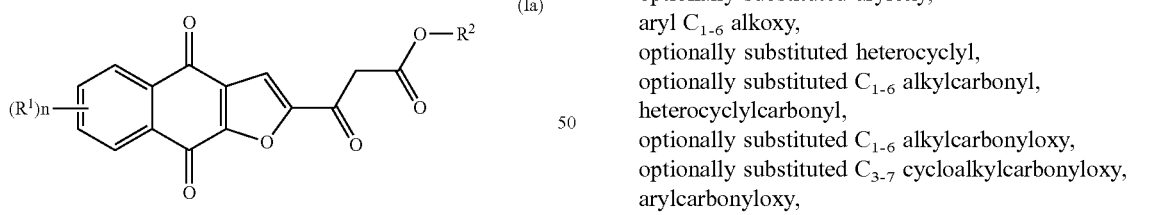

or a pharmaceutically acceptable salt thereof, wherein
each $R^1$ is independently
hydrogen
halogen
hydroxy,
amino,
cyano,
nitro,
$C_{1-12}$ alkyl,
$C_{2-6}$ alkenyl,
$C_{2-6}$ alkynyl,
$C_{3-7}$ cycloalkyl,
$C_{3-7}$ cycloalkenyl,
aryl,
heterocyclyl group,
$C_{1-6}$ alkoxy,
aryloxy,
$C_{1-6}$ alkylthio, or
arylthio, or
two $R^1$ bonded to the adjacent carbon atoms on a benzene ring are optionally joined to form $C_{1-4}$ alkylenedioxy,
$R^2$ is
$C_{1-12}$ alkyl optionally substituted by substituent(s) selected from substituent group α,
$C_{2-6}$ alkenyl optionally substituted by substituent(s) selected from substituent group α,
$C_{2-6}$ alkynyl optionally substituted by substituent(s) selected from substituent group α,
$C_{3-7}$ cycloalkyl optionally substituted by substituent(s) selected from substituent group α,
aryl optionally substituted by substituent(s) selected from substituent group α,
aryl $C_{1-6}$ alkyl optionally substituted by substituent(s) selected from substituent group α, or
heterocyclyl optionally substituted by substituent(s) selected from substituent group α,
n is an integer of 1-4 when $R^1$ is hydrogen,
n is an integer of 1 or 2 when $R^1$ is not hydrogen, and
the substituent group α consists of
halogen,
hydroxy,
optionally substituted amino,
carboxy,
$C_{1-6}$ alkoxycarbonyl,
sulfo group,
phosphoric acid group,
di $C_{1-6}$ alkyl phosphoric acid group,
cyano,
optionally substituted $C_{1-6}$ alkyl,
$C_{3-7}$ cycloalkyl,
$C_{3-7}$ cycloalkyl $C_{1-6}$ alkyl,
optionally substituted $C_{1-6}$ alkoxy,
$C_{1-6}$ alkylthio,
optionally substituted aryl,
optionally substituted aryloxy,
aryl $C_{1-6}$ alkoxy,
optionally substituted heterocyclyl,
optionally substituted $C_{1-6}$ alkylcarbonyl,
heterocyclylcarbonyl,
optionally substituted $C_{1-6}$ alkylcarbonyloxy,
optionally substituted $C_{3-7}$ cycloalkylcarbonyloxy,
arylcarbonyloxy,
monocyclic heterocyclylcarbonyloxy,
optionally substituted $C_{1-6}$ alkoxycarbonyloxy,
optionally substituted heterocyclyl $C_{1-6}$ alkoxycarbonyloxy,
$C_{3-7}$ cycloalkyloxycarbonyloxy,
heterocyclyloxycarbonyloxy,
optionally substituted heterocyclyloxy,
tri $C_{1-6}$ alkylammonio,
optionally substituted $C_{1-6}$ alkylsulfonyl and
$C_{1-6}$ alkylsulfamoylcarbonyl,
comprising
a step of reacting a compound represented by the formula (2):

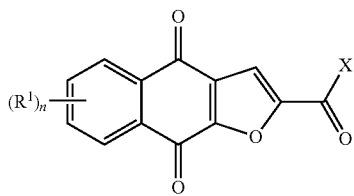

(2)

or a salt thereof, wherein X is halogen, and $R^1$ is as defined for $R^2$ in said formula (Ia), in inert solvent in the presence of a base and a compound represented by the formula (3):

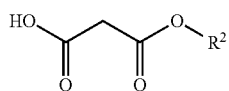

(3)

or a salt thereof, wherein $R^2$ is as defined for $R^2$ in said formula (Ia).

2. The production method according to claim 1, wherein the base comprises magnesium chloride or trimethylamine.

3. The production method according to claim 1, further comprising
a step of producing a compound represented by the formula (2):

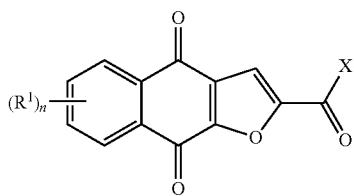

(2)

or a salt thereof, wherein X and n are as defined above, from a compound represented by the formula (1):

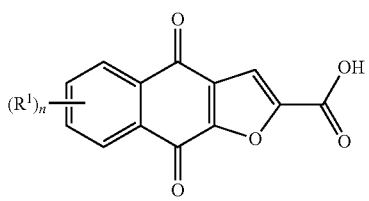

(1)

or a salt thereof, wherein $R^1$ and n are as defined above, before the step of reacting a compound represented by the formula (2) or a salt thereof.

4. The production method according to claim 1, wherein $R^1$ is hydrogen or halogen.

5. The production method according to claim 1, wherein the substituent group α consists of
halogen,
hydroxy,
optionally substituted amino,
carboxy,
$C_{1-6}$ alkoxycarbonyl,
sulfo group,
phosphoric acid group,
di $C_{1-6}$ alkyl phosphoric acid group,
cyano,
$C_{1-6}$ alkyl,
$C_{3-7}$ cycloalkyl,
$C_{1-6}$ alkoxy,
optionally substituted aryl,
optionally substituted aryloxy,
aryl $C_{1-6}$ alkoxy,
optionally substituted heterocyclyl group,
optionally substituted $C_{1-6}$ alkylcarbonyl,
heterocyclylcarbonyl,
optionally substituted $C_{1-6}$ alkylcarbonyloxy,
optionally substituted $C_{3-7}$ cycloalkylcarbonyloxy,
monocyclic heterocyclylcarbonyloxy,
optionally substituted $C_{1-6}$ alkoxycarbonyloxy,
optionally substituted heterocyclyl $C_{1-6}$ alkoxycarbonyloxy,
$C_{3-7}$ cycloalkyloxycarbonyloxy,
heterocyclyloxycarbonyloxy,
optionally substituted heterocyclyloxy and
tri $C_{1-6}$ alkylammonio.

6. The production method according to claim 1, wherein $R^2$ is $C_{1-6}$ alkyl optionally substituted by substituent(s) selected from substituent group α, $C_{2-6}$ alkenyl optionally substituted by substituent(s) selected from substituent group α, $C_{3-7}$ cycloalkyl optionally substituted by substituent(s) selected from substituent group α, aryl optionally substituted by substituent(s) selected from substituent group α, aryl $C_{1-6}$ alkyl optionally substituted by substituent(s) selected from substituent group α, or heterocyclyl optionally substituted by substituent(s) selected from substituent group α, and
the substituent group α consists of halogen, hydroxy, optionally substituted amino, carboxy, sulfo group, phosphoric acid group, cyano, $C_{1-6}$ alkyl, $C_{3-7}$ cycloalkyl, $C_{1-6}$ alkoxy, aryl and heterocyclyl group.

7. The production method according to claim 1, wherein $R^2$ is
(1) $C_{1-6}$ alkyl optionally substituted by substituent(s) selected from hydroxy, optionally substituted amino, carboxy, sulfo group, phosphoric acid group, di $C_{1-6}$ alkyl phosphoric acid group, heterocyclyl, optionally substituted $C_{1-6}$ alkoxy, optionally substituted $C_{1-6}$ alkylcarbonyloxy, monocyclic heterocyclylcarbonyloxy, $C_{3-7}$ cycloalkyloxycarbonyloxy and heterocyclyloxycarbonyloxy;
(2) $C_{2-6}$ alkynyl optionally substituted by substituent(s) selected from hydroxy, optionally substituted amino, carboxy, sulfo group, phosphoric acid group and heterocyclyl;
(3) heterocyclyl group optionally substituted by substituent(s) selected from hydroxy and optionally substituted $C_{1-6}$ alkyl; or
(4) aryl $C_{1-6}$ alkyl substituted by substituent(s) selected from hydroxy, optionally substituted amino, carboxy, sulfo group, phosphoric acid group and heterocyclyl, or a pharmaceutically acceptable salt thereof.

8. The production method according to claim 1, wherein $R^2$ is
(1) $C_{1-6}$ alkyl optionally substituted by substituent(s) selected from hydroxy, optionally substituted $C_{1-6}$ alkoxy, optionally substituted $C_{1-6}$ alkylcarbonyloxy and monocyclic heterocyclylcarbonyloxy; or
(2) $C_{2-6}$ alkynyl optionally substituted by substituent(s) selected from optionally substituted amino and heterocyclyl; or (3) heterocyclyl optionally substituted by optionally substituted $C_{1-6}$ alkyl, or a pharmaceutically acceptable salt thereof.

9. The production method according to claim 1, wherein $R^1$ is hydrogen, or a pharmaceutically acceptable salt thereof.

* * * * *